US008969034B2

(12) United States Patent
Koutsioulis et al.

(10) Patent No.: US 8,969,034 B2
(45) Date of Patent: Mar. 3, 2015

(54) ENDOGLYCOSIDASES THAT CLEAVE O-LINKED GLYCANS

(75) Inventors: Dimitris Koutsioulis, Hrakleio (GR); Ellen Guthrie, Andover, MA (US)

(73) Assignee: New England Biolabs, Inc., Ipswich, MA (US)

( * ) Notice: Subject to any disclaimer, the term of this patent is extended or adjusted under 35 U.S.C. 154(b) by 424 days.

(21) Appl. No.: 12/988,344

(22) PCT Filed: Apr. 7, 2009

(86) PCT No.: PCT/US2009/039735
§ 371 (c)(1),
(2), (4) Date: Nov. 8, 2010

(87) PCT Pub. No.: WO2009/129086
PCT Pub. Date: Oct. 22, 2009

(65) Prior Publication Data
US 2011/0053215 A1     Mar. 3, 2011

Related U.S. Application Data

(60) Provisional application No. 61/046,129, filed on Apr. 18, 2008.

(51) Int. Cl.
| C12P 21/06 | (2006.01) |
| C12N 9/24 | (2006.01) |
| C07H 21/04 | (2006.01) |
| C07K 1/00 | (2006.01) |

(52) U.S. Cl.
CPC ....... *C12Y 302/01097* (2013.01); *C12N 9/2402* (2013.01)
USPC ........ 435/68.1; 435/69.1; 435/200; 536/23.1; 536/23.2; 530/350

(58) Field of Classification Search
CPC ..................... C12N 9/2402; C12Y 302/01097
USPC .............. 435/68.1, 69.1, 200; 536/23.1, 23.2; 530/350
See application file for complete search history.

(56) References Cited

U.S. PATENT DOCUMENTS

| 5,718,895 | A * | 2/1998 | Asgharian et al. ........... 424/94.1 |
| 6,740,509 | B2 * | 5/2004 | Karakasa et al. ................ 435/74 |
| 7,351,562 | B2 | 4/2008 | Chatterjee et al. |
| 7,354,753 | B2 | 4/2008 | Nielsen et al. |
| 7,358,071 | B2 | 4/2008 | Payne et al. |
| 7,358,074 | B2 | 4/2008 | Jackson et al. |
| 7,364,892 | B2 | 4/2008 | Klotz et al. |
| 7,445,921 | B2 * | 11/2008 | Oura et al. .................... 435/193 |
| 2006/0223140 | A1 | 10/2006 | Oura et al. |

FOREIGN PATENT DOCUMENTS

| EP | 1767645 A1 | 3/2007 |
| WO | 2004/106367 A2 | 12/2004 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Bruggemann et al., The complete genome sequence of *Propionibacterium acnes*, a commensal of human skin. Science, 2004, vol. 305: 671-673.*
Guo et al., Protein tolerance to random amino acid change. PNAS., 2004, vol. 101 (25): 9205-9210.*
Brooks et al., The substrate specificity of the enzyme Endo-a-N-acetyl-D-galactosaminidase from *Diplococcus pneumonia*. Glycoconjugate Journal, 1997, vol. 14: 183-190.*
Mongodin et al., Secrets of soil survival revealed by the genome sequence of *Arthobacter aurescens*. PLoS Genetics, 2006, vol. 2 (12) e214: 2094-2106.*
Iwai et al., Core 3 synthase is down-regulated in colon carcinoma and profoundly suppresses the metastatic potential of carcinoma cells. PNAS., 2005, vol. 102 (12): 4572-4577.*
Podolsky DK., Oligosaccharide structures of human colonic mucin. The J. Biol. Chem., 1985, vol. 260 (14): 8262-8271.*
Wang et al., Glycerol production by microbial fermentation: A review. Biotechnol. Adv., 2001, vol. 19: 201-223.*
International Sea, EP, Jul. 9, 2009, New England Biolabs.
Ohtsubo and Marth Cell 126:855-867 (2006).
Varki Glycobiology 3:97-130 (1993).
Tarentino and Plummer Methods Enzymol. 230:44-57 (1994).
Kakehi et al. J Chromatogr A. 680:209-215 (1994).
Royle et al. Anal Biochem. 304:70-90 (2002).
Huang and Aminoff J Biol Chem. 247:6737-6742 (1972).
Umemoto et al. J Biol Chem. 252:8609-8614 (1977).
Glasgow et al. J Biol Chem. 252:8615-8623 (1977).
Brooks and Savage Glycoconj J. 14:183-190 (1997).

(Continued)

*Primary Examiner* — Ganapathirama Raghu
(74) *Attorney, Agent, or Firm* — New England Biolabs, Inc; Harriet M. Strimpel

(57) ABSTRACT

Methods and compositions have been described that relate to a newly identified polypeptide family wherein each member has O-glycosidase activity and specified sequence characteristics. This family of enzymes can be used for example for cleaving O-linked glycans and for synthesis of neoglycopeptides or neoglycoproteins.

9 Claims, 22 Drawing Sheets

(56) References Cited

OTHER PUBLICATIONS

Fan et al. Agric Biol Chem. 54:233-234 (1990).
Ashida et al. Arch Biochem Biophys. 373:394-400 (2000).
Fujita et al. J Biol Chem. 280:37415-37422 (2005).
Ishii-Karakasa et al. Biochem J. 288:475-482 (1992).
Ishii-Karakasa et al. Eur J Biochem. 247:709-715 (1997).
Finn et al. Nucleic Acid Research 34:D247-D251 (2006).
Altschul et al. Nucleic Acids Res. 25:3389-3402 (1997).
Koutsioulis et al, Glycobiology, 18, 10, 799-805, 2008.
Goda et al, Biochem and Biophys Res Comm, 375, 441-446, 2008.
Katayama et al, J Biosci and Bioengin, 99, 5, 457-465, 2005.

* cited by examiner

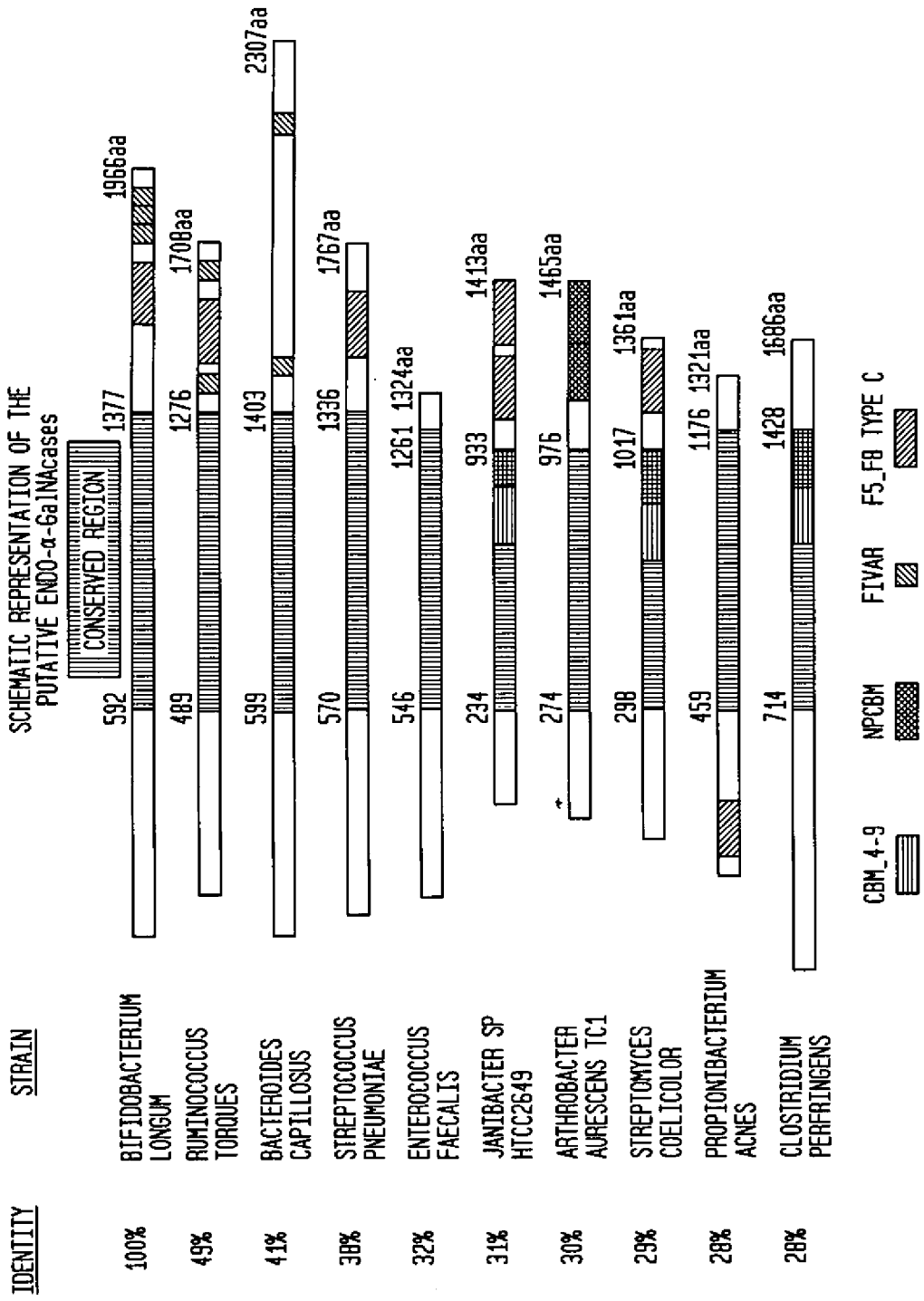

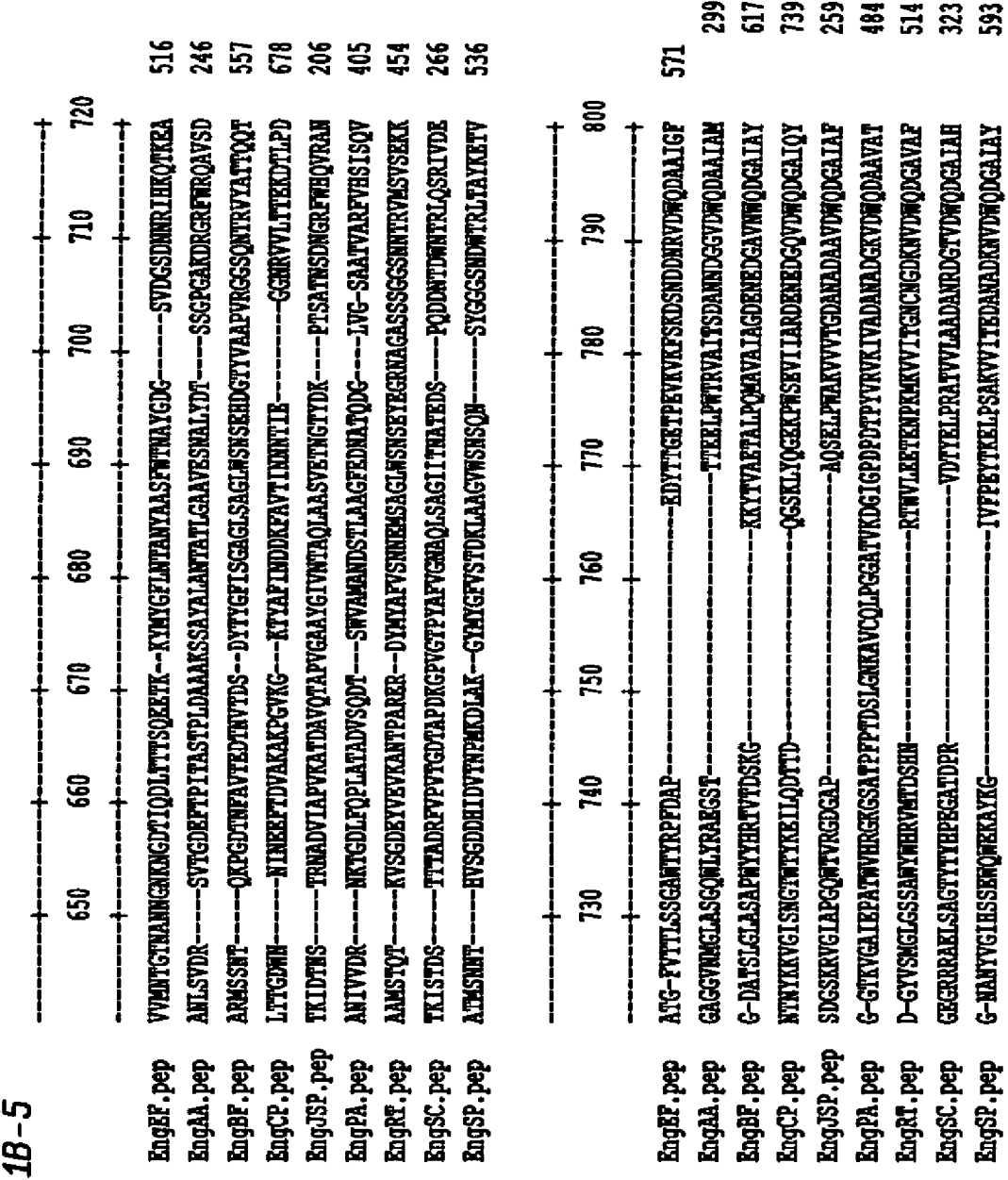

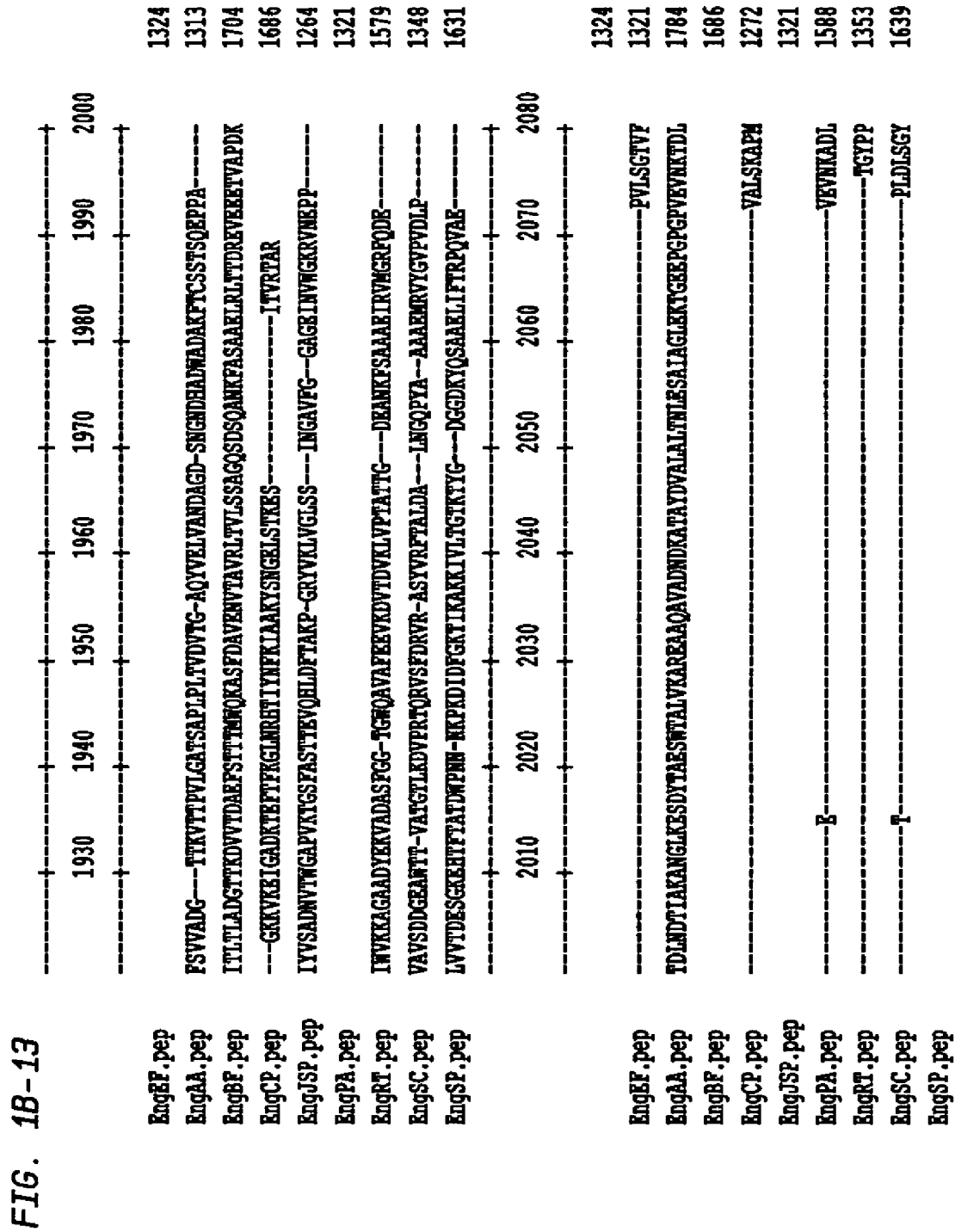

EngRF.pep
EngAA.pep        NGDDAGDDWGDWADAKFSCA                    [SEQ ID NO: 4]    1324
EngBF.pep        SDVATIALAGLLLAGAGAALAYRNNREQL           [SEQ ID NO: 5]    1465
EngCP.pep                                                                  1966
EngJSP.pep       N-SINGAAFAATAELQFVAPATP                 [SEQ ID NO: 7]    1686
EngPA.pep                                                                  1413
EngRT.pep        TSFFGWGAAGIFGLFAAAAAFFERKRRRQ           [SEQ ID NO: 8]    1321
EngSC.pep                                                                  1708
EngSP.pep        BSQSDTALILASVSLALSALFVVKTKKD            [SEQ ID NO: 10]   1361
                                                                           1767
```

FIG. 5-1

```
                  10        20        30        40        50        60        70        80
                  |         |         |         |         |         |         |         |
EngEF.pep  MKHGKIKRFSTLTLLASATILVPLSTSAEETTHSSTETSSSMVEPTATEEKLWQSDFPGGKTGEWQDVIGKTHRELAGES  80
EngPA.pep  MSRTPRGRSIGALAVSAGTMLALIAPTAPAHAETRYRQINQAAITAVAADSATATDPISNTLDGHPDTIWHTTWQNGKDP  80
EngAA.pep  --------------------------------------------------------------------------------  0

90       100       110       120       130       140       150       160
                  |         |         |         |         |         |         |         |
EngEF.pep  LAISRDAAAGNNAVSLNLDSPKLADGEVETKFKYTAGSGRTGVIIRGNTKDSWVPVGYNANGKWLVESPNSWHDSISGPT  160
EngPA.pep  LPHWIVFKLGDEAVNL---------------------GKVEITPRSSSNGSGRMHDYELY--------------------  119
EngAA.pep  ----------------------------------------MPRLSSPG-------------------------------  8

170       180       190       200       210       220       230       240
                  |         |         |         |         |         |         |         |
EngEF.pep  LNEDTNYLLKVRYVGEKITIWLNTTLIYEGEPVLANGDKIPTEAGHVGVRLWYDKKIVNYDYFKNGPVDSIPEIVPEVTQ  240
EngPA.pep  -------------------------TANTKTCNMAAFSSAKPVATGSYGA---------------SDTSIRKITP  154
EngAA.pep  -------------------------RLASLSLACVVASSSLG------------------------  25

250       260       270       280       290       300       310       320
                  |         |         |         |         |         |         |         |
EngEF.pep  IAPVKVFTKIGVAPKLPKQVKVTYNTGKEANEAVRWNEIDPDAYKEPGTPEVDGTLENTNIKAKASIVVAKDNEAEKGDK  320
EngPA.pep  AATKATCVKVKVNSSWGGDGSDEEVSSMAEFNAFTVDGSDPSPDPTP--------------SEPPTPEVPKDAIS-----  215
EngAA.pep  -------------------------LLAIPPAAAAPS--------------TQPADIVSAADTAT-----  51

330       340       350       360       370       380       390       400
                  |         |         |         |         |         |         |         |
EngEF.pep  ISSADLTAVVDPQFPRIIRYEDPQSHQVIFNGQHEKIDQVMIDGKAYKATAEKQKSEAHQAVYNVAVPEIG-LRFTTTLT  399
EngPA.pep  LSDGTVTVRARRDFPQVIDYTVGHAHMAGR--IGSPLTKVRINGADHVATVSAPTTTGSSASWKLTFRDLPGVELTADIK  293
EngAA.pep  ITSGDLRVDVGTTFPQVLGYTDAASKARLDG-TTTRLSTITLNGTEYTVSGTSAASGKDARDYVLTLPDFGNTVIKARLS  130

410       420       430       440       450       460       470       480
                  |         |         |         |         |         |         |         |
EngEF.pep  VSEGQELAMKLSDIRE-EGTKIHTISIPNQGLISVNSTDEGATFAGVVMNTGTHANNGNKNGDTIQDLTTT--SQEETKK  476
EngPA.pep  VSDG-VMTWSIPHIVDTPDHRVNTVSVPGLTLASVTSTDPKAQLS-----SANIVVDRNKTGDLFQPLAT---ADVSQDT  364
EngAA.pep  VKKN-VVSFNITEIKDSAEHQVRTLQLPRLNLVTVGSTQPGSQVS-----TANLSVDRSVTGDEFTPITASTPLDAAAKS  204
```

FIG. 5-2

```
                   490       500       510       520       530       540       550       560
                    |         |         |         |         |         |         |         |
EngEF.pep  YMYGFLNTANYAASFWTNAYGDGSVDGSDWNR---IHKQTKEAATGFVTTLSSGANTYRPFDAPEDYT------------ 541
EngPA.pep  SWVANANDSTLAAGPEDNATQDGLVGSAATVAR--FVESISQVGGTKVGAIEPATWVHRGKGSATPFPTDSLGNKAVCQL 442
EngAA.pep  SAYALANTATLGAAVESNALYDTSSGPGAKDRGRFWRQAVSDGAGGVNMGLASGQWLYRAEGSTT--------------- 269

570       580       590       600       610       620       630       640
                    |         |         |         |         |         |         |         |
EngEF.pep  ------------TGETPEVKVKFSKDSNDDNR VDWQDAA IGFRSINNNPMGAEKVPELVNQRIPFNFASQATHPFLVTLD 609
EngPA.pep  PGGATVKDGIGPDPDTPYVRVKIVADANADGK VDWQDAA VATRDVTMKPTGSGDVANKVITHIPFNIVSQATHPFLRTLD 522
EngAA.pep  ------------TEELPWTRVAITSDANNDGG VDWQDAA IAMRSIQVSPNKGEQTPDNVITHIPFNFASQATHPFLRTLD 337

650       660       670       680       690       700       710       720
                    |         |         |         |         |         |         |         |
EngEF.pep  ESKRIYNLTDGLGQMNLLKGYQNEGHDSAHPDYG-AIGQRPGGEQALNQLIDEGHKLHAVPGVHINDTESYPEAKGFNEE 688
EngPA.pep  DVKRISLATDGLGQQALLKGYQAEGHDSAHPDYGGNVSHRAGGMKDLEKLTESGRQWNTDFGIHVNLVESYPEANHFGDN 602
EngAA.pep  DVKRISLATDGLGQVAMLKGYTSEGHDSANTDYGNNNFNTRAGGLEDLNTLVKEGKEWNASPGVHINATEIYPEAKSFSED 417

730       740       750       760       770       780       790       800
                    |         |         |         |         |         |         |         |
EngEF.pep  LVDP-TKRGWDWLDPSYFIKQRPDTLSGRRYERFKELKQKAP---NLDYIYVDVWGNQGESGWASRQLSKEINSLGWFTT 764
EngPA.pep  ILVKPYQKAWDWMEQSYRMDYAKDLGSGQLFARLNQLRKELGAKSHLDWLYFDTN---YPAGWQNDRIANALNAEGWRIG 679
EngAA.pep  LLRADKGLGWNWLDQSYYMNQREDINSGKIAQRIKELREST--NKNLDFVYVDVY---YEFGWLAERLQQELVKNGPRVG 492

810       820       830       840       850       860       870       880
                    |         |         |         |         |         |         |         |
EngEF.pep  NEFPNALEYDSVWNHWSAEKDYGGTTTKGFNSTIVRFIRNEQKDTWIISDNPLLGGAEFEAYEGWVGKTNFNTYRQKTFA 844
EngPA.pep  SEWSSTYPRYNQWSHWANDENYG-TGNKGYSSRIIRFIDNSRRDTWNP--DPILGNSNVVEYEGWTSHNDYNAFIANVWQ 756
EngAA.pep  SEWADHLSRNNTWSHWANDEKYGGSTNKGINSQILRFINNTQSDVWNP--DPKLGVSHIVEFEGWTGQNDFNAFSENVWT 570

890       900       910       920       930       940       950       960
                    |         |         |         |         |         |         |         |
EngEF.pep  INVPTKFLQHYQITNWETTTAADGQIYGTIKLANGAEKVTVT----QADANSPRSITLNETEVLKGD-AYLLPWN---VN 916
EngPA.pep  RNLPTKFLQRSDIMSWQD---------GRIAFANGAVATSSKKSISGHEIPTARTITFDGATVFKEGGSYLLPWS---NG 824
EngAA.pep  ANVPAKFLQHHFITKWTA---------ERIELADGVAVTGN---------TAEGRNITVGGTSVLQGG-TYLLPWSSKENG 632
```

FIG. 5-3

```
                      970       980       990      1000      1010      1020      1030      1040
                       |         |         |         |         |         |         |         |
EngEF.pep  GQDKLYHWNPKGGTSTWSLDKKMQGKTHLHLYELTDQGRIDKGAIATTHNQVTIQAEAHTPYVIAEPDS----IEPMTFG  992
EngPA.pep  GSDRLYYWNPGHGSATWKLTHSWAAQKSVSLFHLTDTGRVKVAEIPVTNRSIRIPATKARTAYVLYPTSKVPAAKTPHWG  904
EngAA.pep  KVDKLYHYNPTGGASTWTLTQEFAKSSSLEQFKLTDNGRVKVADVPVVHGQVTVTADAKQPYILAPKNNKAELPKKADFG  712

1050      1060      1070      1080      1090      1100      1110      1120
                       |         |         |         |         |         |         |         |
EngEF.pep  TGTPFKDPGFHEANTLKHNWKVFRGDGEVKKDAHGDYVFSSEKERTEIKQDIHLPK--PGKYSLYLHTETHDRKATVTVK  1070
EngPA.pep  EGSHFANPGFYSGDTAG---WNARGHVSVKHNDRGHFHLEPGKAQSQISQVLHLPAGDHSLWAHVQIDPTKTRPVGLAVD  981
EngAA.pep  EGTAFHDPGFHGTDLSP---WHPAGPVTQVRDDKGRRFAEHGATPSSISQDVQLDAGTQSVSAHIEIQPGKTRPTTLSVD  789

1130      1140      1150      1160      1170      1180      1190      1200
                       |         |         |         |         |         |         |         |
EngEF.pep  IGGKK----------YTRTVMHSVAQHYIQADIHHTSRKHPQYHQHMRIDFEIPDNAKKGSVTLAVDKGHSVTKFDDLR  1139
EngPA.pep  GTGVTPIDHQKGCGGHAESVITSTTAIHATASDEYFG-----TYHQRLRVAFHS--DGRPVTVTLKALAGHAIVSADDFR  1054
EngAA.pep  IDGKT----------ESVTIDSSHAEHYVAGDEKHG-----TAPQRIRVLVDVPRHNTKATVTVQAADGDATVRVDDFR  853

1210      1220      1230      1240      1250      1260      1270      1280
                       |         |         |         |         |         |         |         |
EngEF.pep  IVERQTDIMH-PDKQTVIKQDFEDTQAVGLYPFVKGSAGGVEDPRIELSERHEPYTQYGWHGHLVSDVLEGHWSLKAHKQ  1218
EngPA.pep  VVDAAVPSDPHVTPATVLFQNFEDVDTG-YWPFVTGSAGMEGDARTQLSRRHEPYTQKGWHSGRAHDSVLSGDHSLKMHEE  1133
EngAA.pep  AVKTTR-----VPTTGVLSEDFKNVDQG-WGPFVKGDAGGSTDPRTEITERHEPFTQKGWDANVIDEVLDGTHSLIAHDE  927

1290      1300      1310      1320      1330      1340      1350      1360
                       |         |         |         |         |         |         |         |
EngEF.pep  G------AGIMLQTIPQHIKFEPH-KKYTVQFDYQTDGEHVFTAGTIHGELKHNHNDFKPVGELTSTAADGQTKEHYEAEII  1291
EngPA.pep  R------NGIVLRTTTASAPLTGGGTRYRISFDYQADKP-GYSFVTGHDKVSGKSVKEVITESEAMGVATSTTHFSTDIV  1206
EngAA.pep  HRAPNGGPGMVYRTTEASVPFQAG-HKYKVSFDYQNSKRAGQYAWVSGYDSQAGPAVTGSQAIEAKTSTTRFEQILDTGFC  1006

1370      1380      1390      1400      1410      1420      1430      1440
                       |         |         |         |         |         |         |         |
EngEF.pep  GDASGHTTFGIFTTGADKDFIMDHFTVTVESKK    [SEQ ID NO: 2]                               1324
EngPA.pep  VKDQ--PAHIGFTHQGEGDMSIDHLRIEKLDPRPISVTSTQAAVFPD-------------------------------  1251
EngAA.pep  GDYP--VGLQRTGSSHGSDFTLDHFLVEDLGASEAVPACAQLSAELQGDVVQQGKAQDFVTTFVSDEPAAISGLAVALEL  1084
```

FIG. 5-4

```
              1450      1460      1470      1480      1490      1500      1510      1520
              |         |         |         |         |         |         |         |
EngEF.pep                                                                                    1324
EngPA.pep   ----ACKPTPEPIQPAQPSASAPTTSGSPQAPGTGN------RPNRYALPRTGADGAG--------------------    1299
EngAA.pep   PEGWTATPSTPATAPTLPAGGTLTTTWKITAPASADGDYPITAKASYTVSSSGIDPAGSRTISTTTTVRTLPKPPQATVP    1164

1530      1540      1550      1560      1570      1580      1590      1600
              |         |         |         |         |         |         |         |
EngEF.pep                                                                                    1324
EngPA.pep   ----------------------------------------LG--------------------FSSSEAASATAA        1313
EngAA.pep   ASDHPWVSATNGWGPVEKDQSNGGTGAGDGTPLTLNGTVYAKGLGAHANGTVRYYLGGYCTAPTATVGIDDAQPTRGSVK    1244

1610      1620      1630      1640      1650      1660      1670      1680
              |         |         |         |         |         |         |         |
EngEF.pep                                                                                    1324
EngPA.pep   VGVSRQGR    [SEQ ID NO: 3]                                                       1321
EngAA.pep   FSVVADGTTKVTTPVLGATSAPLPLTVDVTGAQYVELVANDAGDSNGNDHADWADAKFTCSSTSQEPPAPVLSGTVFASD    1324

1690      1770      1710      1720      1730      1740      1750      1760
              |         |         |         |         |         |         |         |
EngEF.pep                                                                                    1324
EngPA.pep                                                                                    1321
EngAA.pep   LPWIGSTNGWGPAERDRANGEQNAGDGPALRLDGVVYSKGIGVHADSKISIATEAKCTAPTAVAGVDDAKLNKGLHGSVV    1404

1770      1780      1790      1800      1810      1820
              |         |         |         |         |         |
EngEF.pep                                                                                    1324
EngPA.pep                                                                                    1321
EngAA.pep   FIVKGGGRELLRTPVLSADSAALPLNVDITGVQNVELIADKNGDDAGDDWGDWADAKFSCA    [SEQ ID NO: 4]    1465
```

ENDOGLYCOSIDASES THAT CLEAVE O-LINKED GLYCANS

BACKGROUND

Glycosylation is a common post-translational modification of proteins. Glycans are implicated in a wide range of biological events such as cell-cell interactions and recognition, inflammation, and autoimmune diseases (Ohtsubo and Marth Cell 126:855-867 (2006); Varki Glycobiology 3:97-130 (1993)). Detailed knowledge of glycan structures would facilitate structure-function correlations. This can be achieved by developing tools for highly sensitive analysis of glycan chains. For example, structural analysis of asparagine-linked carbohydrates (N-linked glycans) can be performed by releasing sugars from the protein backbone using enzymes such as PNGase F (Tarentino and Plummer Methods Enzymol. 230:44-57 (1994)). The O-linked glycans are most commonly attached to serine or threonine residues through the GalNAc residue at the reducing end. So far there is no enzymatic way of releasing of O-glycans intact. Consequently, this is achieved by chemical methods, typically by β-elimination with mild alkali (Kakehi et al. J Chromatogr A. 680: 209-215 (1994)) or mild hydrazinolysis (Royle et al. Anal Biochem. 304:70-90 (2002)). O-linked disaccharides (Core 1 type O-glycan) are among the most abundant core structures found in mucin glycoproteins, for example, the Thomsen-Freidenreich antigen (T antigen) immunodeterminant group and is used as a specific marker of carcinoma (Ohtsubo and Marth Cell 126:855-867 (2006); Varki Glycobiology 3:97-130 (1993)).

To date, endo-α-GalNAcases have been purified from Clostridium perfringens (Huang and Aminoff J Biol Chem. 247:6737-6742 (1972)); Streptococcus pneumoniae (Umemoto et al. J Biol Chem. 252:8609-8614 (1977), Glasgow et al. J Biol Chem. 252:8615-8623 (1977) and Brooks and Savage Glycoconj J. 14:183-190 (1997)); Alcaligenes sp. (Fan et al. Agric Biol Chem. 54:233-234 (1990)); Bacillus sp. (Ashida et al. Arch Biochem Biophys. 373:394-400 (2000)); Bifidobacterium longum (Fujita et al. J Biol Chem. 280: 37415-37422 (2005) and U.S. Publication No. 2006/0223140); and Streptomyces (Ishii-Karakasa et al. Biochem J. 288:475-482 (1992) and Ishii-Karakasa et al. Eur J Biochem. 247:709-715 (1997)). All of the enzymes have a narrow substrate specificity, acting only on the α-linked disaccharide, Galβ1,3GalNAc.

SUMMARY

In an embodiment of the invention, a polypeptide family is described for the first time in which each member is defined by: endo-α-N-acetylgalactosaminidase (endo-α-GalNAcase), also called O-glycosidase activity; an amino acid sequence homology with EngBF measured by an expectation value of less than $e^{-10}$ in a BLAST search; an amino acid sequence comprising SEQ ID NO:1; and an FDY amino acid sequence in a central conserved domain wherein the number of amino acids between the FDY and a C-terminal end of the polypeptide member is no more than 200 amino acids. In particular, the O-glycosidase activity may result in cleavage of a Core 1 and a Core 3 glycan. Another feature of the polypeptide family may include that each polypeptide has a sequence containing less than 1400 amino acids. Another feature of the polypeptide family may include an absence of a carbohydrate-binding domain at the C-terminal end.

In another embodiment of the invention, the polypeptide member is a purified recombinant endo-α-glycosidase, the glycosidase being capable of cleaving a glycosidic bond in GlcNAcβ1,3GalNAcαIpNP.

In another embodiment of the invention, an isolated nucleic acid is provided that encodes a polypeptide member having at least 35% amino acid sequence identity with SEQ ID NO:2 wherein the polypeptide is capable of cleaving GlcNAcβ1, 3GalNAcαIpNP.

In another embodiment of the invention, a method is provided that includes the steps of cleaving an O-linked glycan consisting of either Galβ1,3GalNAc or GlcNAcβ1,3GalNAc linked α1 to serine or threonine from a glycoprotein or glycopeptide with a polypeptide member characterized above, resulting in release of a disaccharide.

In other embodiments, a method is provided for synthesis of a neoglycopeptide or neoglycoprotein using a polypeptide member in the polypeptide family. A method is also provided for (a) performing a BLAST search using a glycosidase in the family of glycosidases described in claim 1 to identify homologs with an expectation value of less than $e^{-10}$; (b) determining the presence of SEQ ID NO:1 or a sequence having at least 90% identity with SEQ ID NO:1; (c) determining the presence of FDY and its location within 200 amino acids from the C-terminal end such that if (a), (b) and (c) are positive, verifying Core 1 and Core 3 glycosidase activity; and (d) preparing by synthesis or cloning, a polypeptide member of a polypeptide family as described above.

The protein accession numbers are: B. longum (AAX4493.1) (EngBF), R. torques (ZP_01966813) (EngRT), B. capillosus (ZP_02035456), S. pneumoniae (YP_873926.1) (EngSP), E. faecalis (NP_815498.1) (EngEF), Janibacter sp. (ZP_00993766.1) (EngJSP), A. aurescens (YP_947239.1) (EngAA), S. coelicolor (NP_630440.1) (EngSC), P. acnes (YP_056270.1) (EngPA), C. perfrigens (YP_695137.1) (EngCP).

Figures 1, 1B:
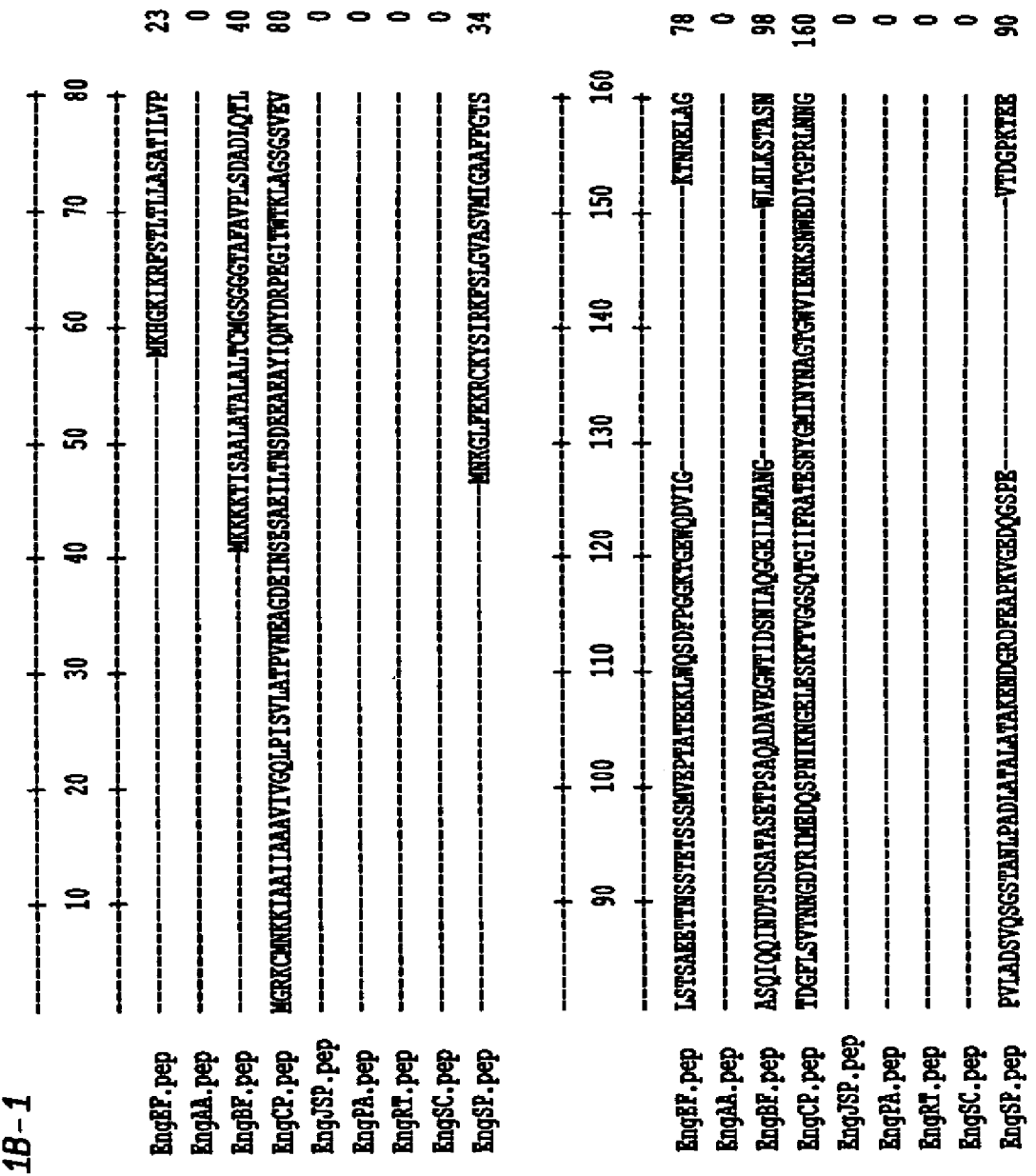
FIG. 1A shows a schematic representation of the putative endo-α-GalNAcases. Alignment of the putative endo-α-GalNAcases that were revealed by BLAST search against the protein sequence of EngBF and the identity results are shown. The grey shaded boxes correspond to the center-located conserved region, while the black and patterned boxes indicate different types of sugar-binding domains (SBD also referred to as CBD). CBM_4_9: carbohydrate binding module (Pfam 02018), NPCBM:novel putative carbohydrate binding module (Pfam 08305), FIVAR: uncharacterized SBD (Pfam 07554) and F5-F8 type C: member of the galactose-binding domain-like superfamily (Pfam 00754). (The Pfam database is a database offered by the Wellcome Trust (London, UK) and is accessible on the Web at pfam.sanger.ac.uk. See also Finn et al. Nucleic Acid Research 34:D247-D251(2006).

FIGS. 1B-1 to 1B-15 show a ClustalW alignment of amino acid sequences of the proteins of FIG. 1A: EngEF.pep (SEQ ID NO:2), EngAA.pep (SEQ ID NO:4), EngBF.pep (SEQ ID NO:5), EngCP.pep (SEQ ID NO:6), EngJSP.pep (SEQ ID NO:7), EngPA.pep (SEQ ID NO:3), EngRT.pep (SEQ ID NO:8), EngSC.pep (SEQ ID NO:9), EngSP.pep (SEQ ID NO:10).

Figures 1, 1B, 2:
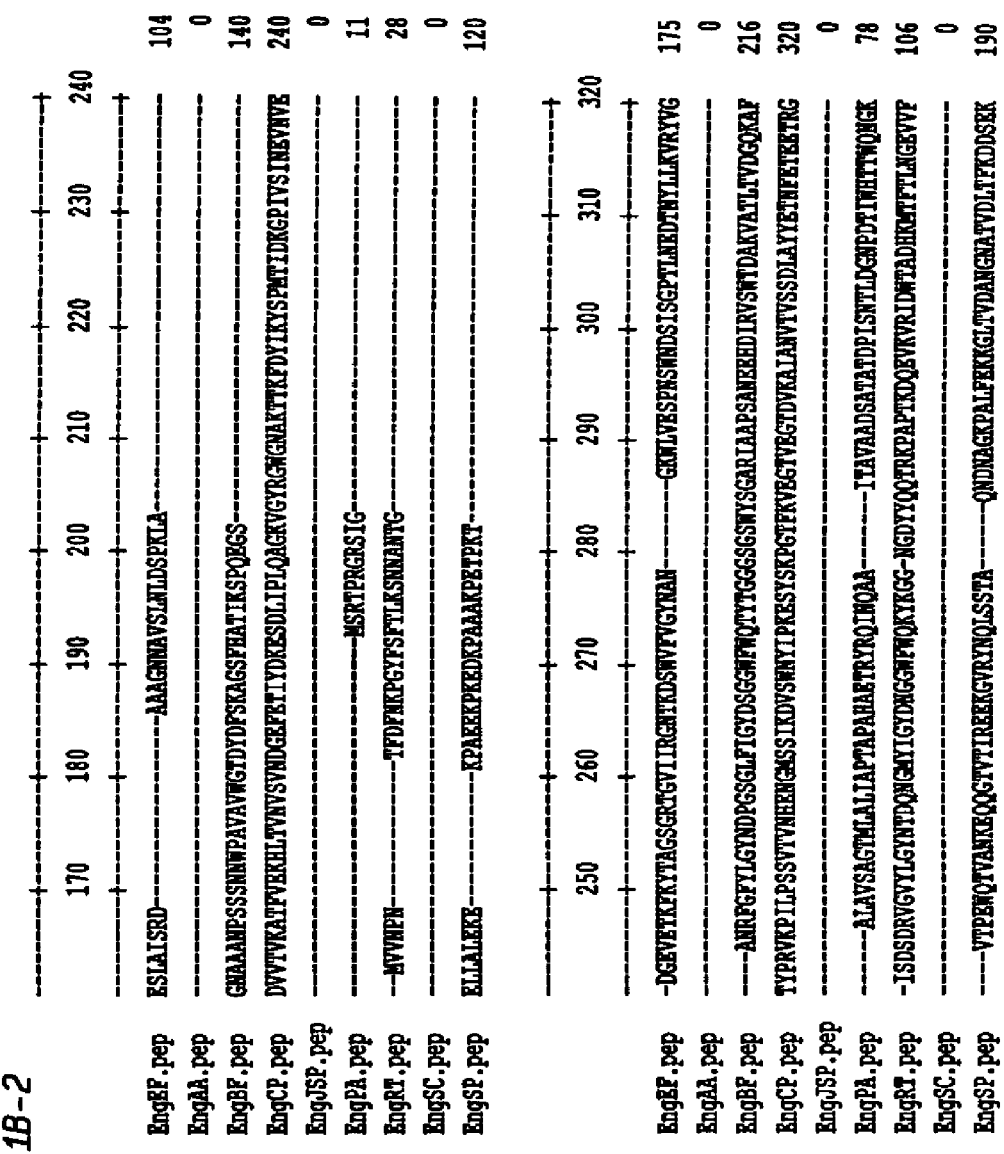

FIG. 2 shows a purified endo-α-GalNAcases. SDS-PAGE analysis using 10-20% polyacrylamide gel, stained by Coomassie Brilliant Blue R-250. Lane M: molecular mass standards, lane 1: EngCP, lane 2: EngEF and lane 3: EngPA.

Figures 1, 1B, 2, 3:
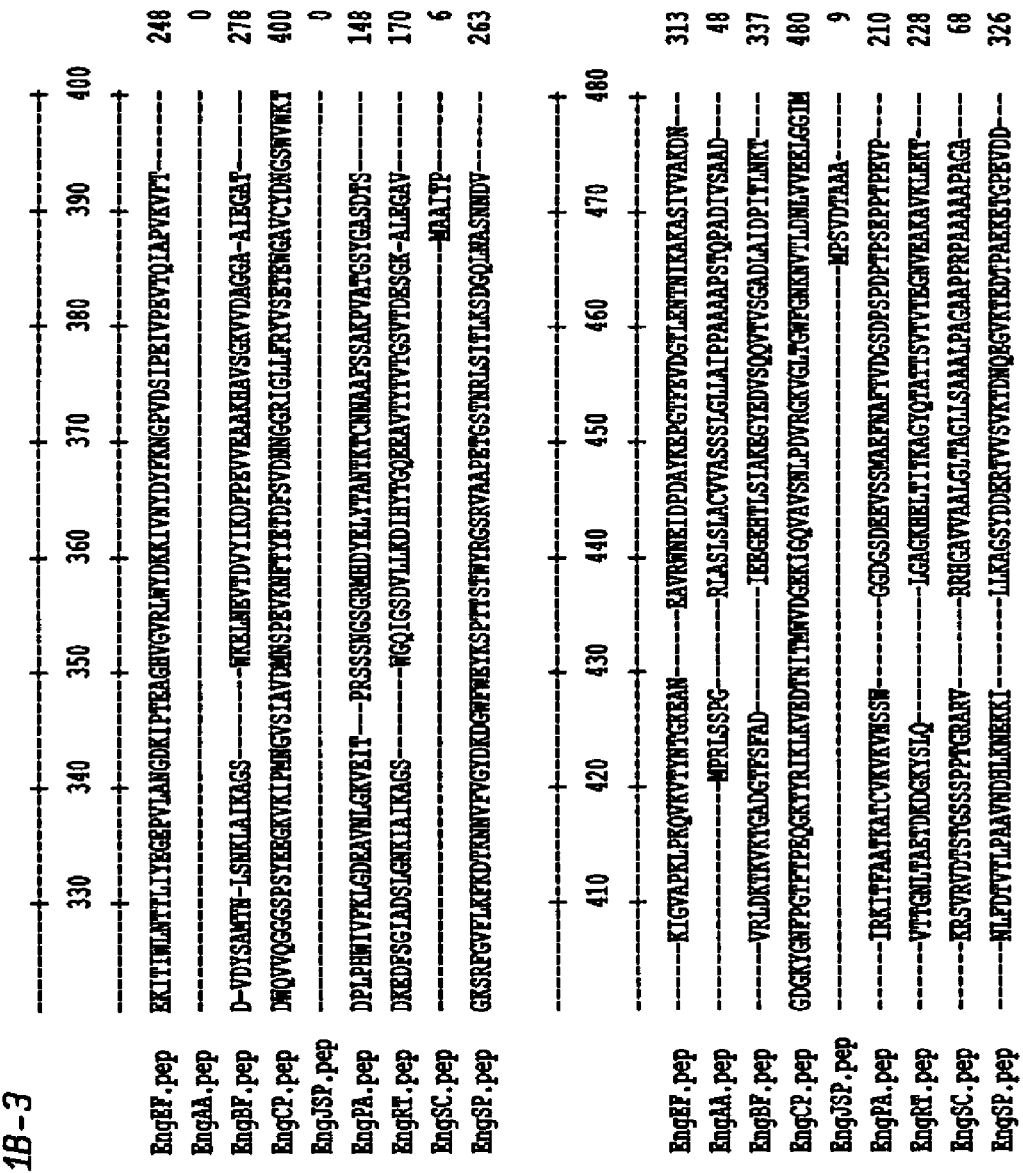

FIG. 3 shows TLC analysis of the reaction products using pNP substrates and natural glycoproteins. Reaction mixtures were incubated with (lane+) and without (lane−) EngEF at 25° C. for 16 h. Lane 1: Core 2 trisaccharide Galβ1,3 (GlcNAcβ1,6)GalNAcα1pNP, lane 2: Core 3 disaccharide GlcNAcβ1,3GalNAcα1pNP, lane 3: Galβ1,3GlcNAcα1pNP disaccharide, lane 4: GalNAcα1pNP, monosaccharide, lane 5: Core 1 disaccharide Gaβ1,3GalNAcα1pNP, lane 6: Fetuin, lane 7: Fetuin+Neuraminidase, lane 8: Asialofetuin, lane 9: k-casein glycopeptides, lane 10: k-casein glycopeptides+Neuraminidase, lane 11: Glycophorin A, lane 12: Glycophorin A+Neuraminidase, lane 13: Mucin glycopeptides, lane 14: Mucin glycopeptides+Neuraminidase.

Figures 1, 1B, 2, 3, 4:
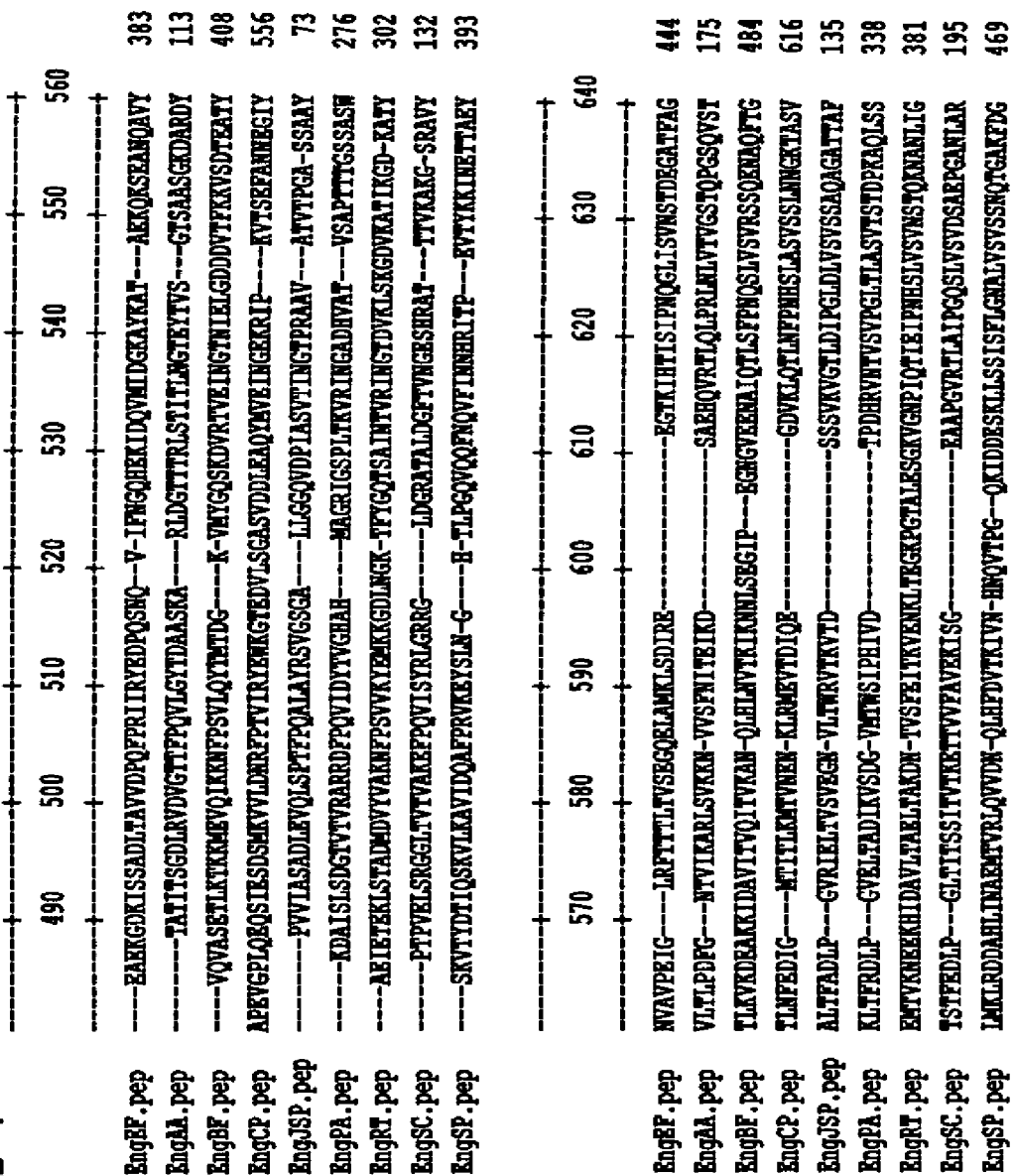

FIG. 4 shows a TLC analysis of the transglycosylation reactions of five different endo-α-GalNAcases EngCP, EngEF, EngPA, EngSP and EngAL. Transglycosylation of disaccharide Gaβ1,3GalNAcα1pNP (A, B) or GlcNAcβ1, 3GalNAcα1pNP (C) to various 1-alkanols by endo-α-GalNAcases. Lane 1: methanol, lane 2: ethanol, lane 3: 1-propanol, lane 4: 1-butanol, lane 5: 1-pentanol, lane 6: 1-hexanol, lane 7: 1-heptanol, lane 8: 1-octanol, lane 9: 1-nonalol and lane S: Galβ1,3GalNAcα1pNP.

Figures 1, 1B, 2, 3, 4, 5, 6:
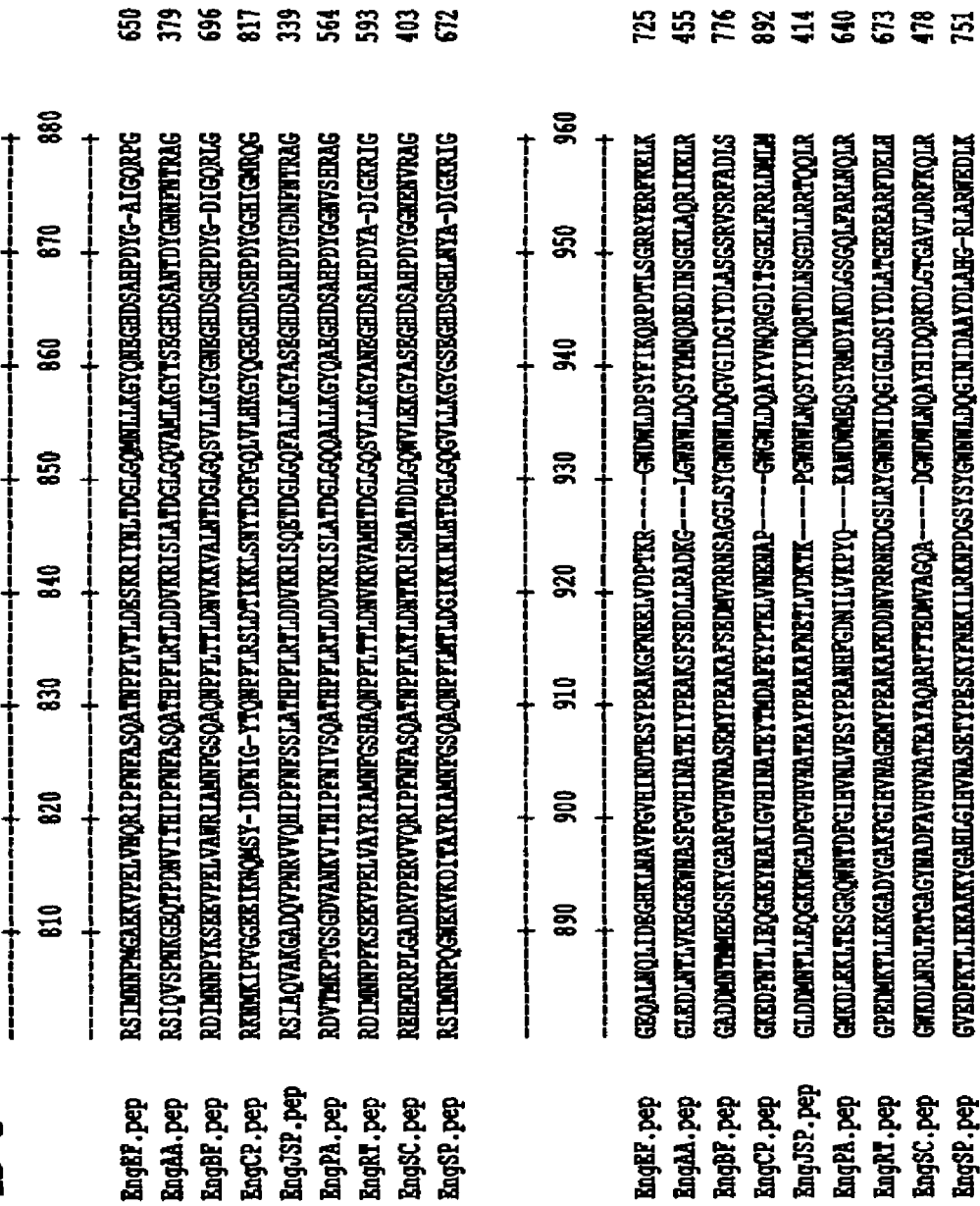
Figures 1, 1B, 2, 3, 4, 5, 6, 7:
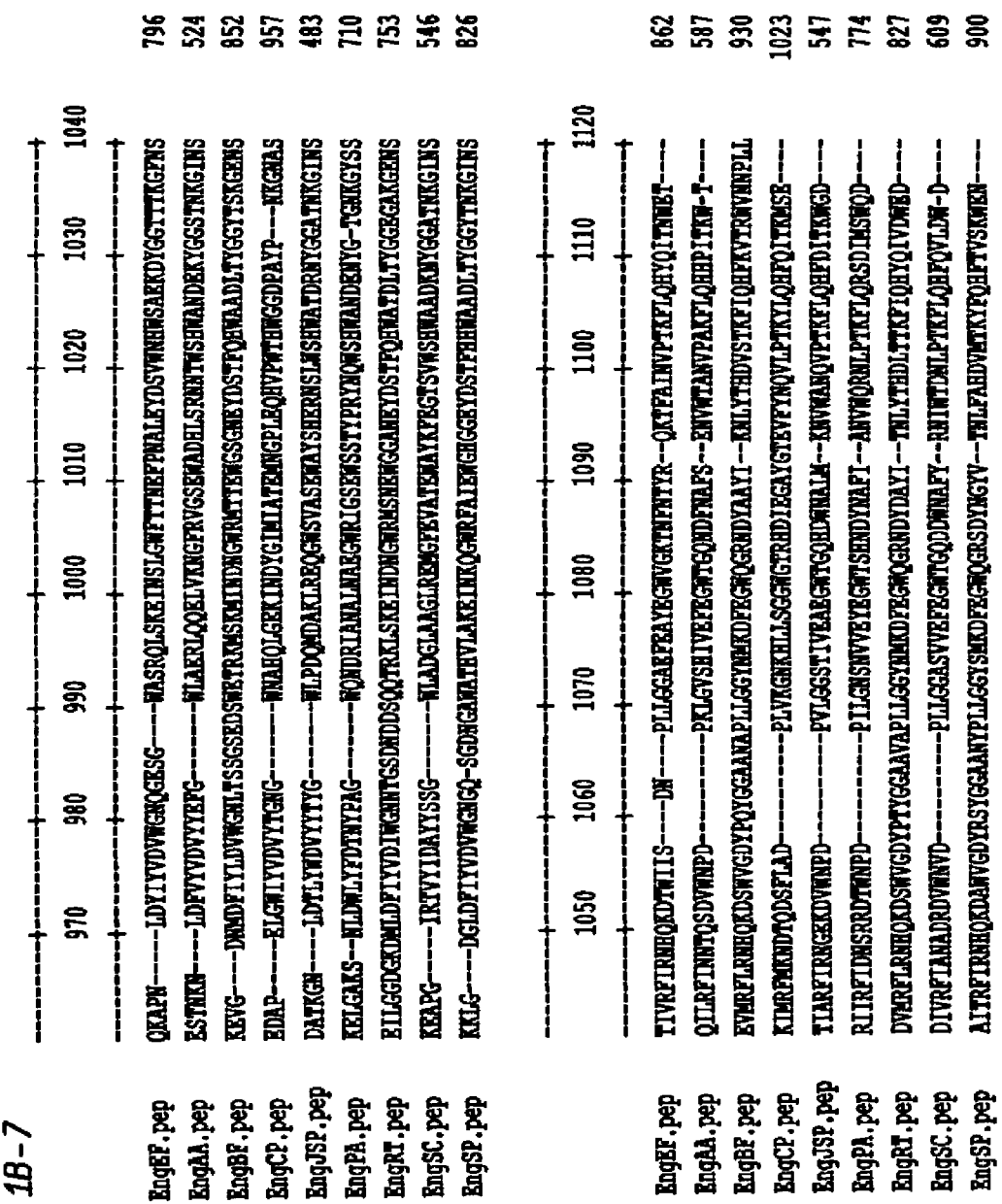
Figures 1, 1B, 2, 3, 4, 5, 6, 7, 8:
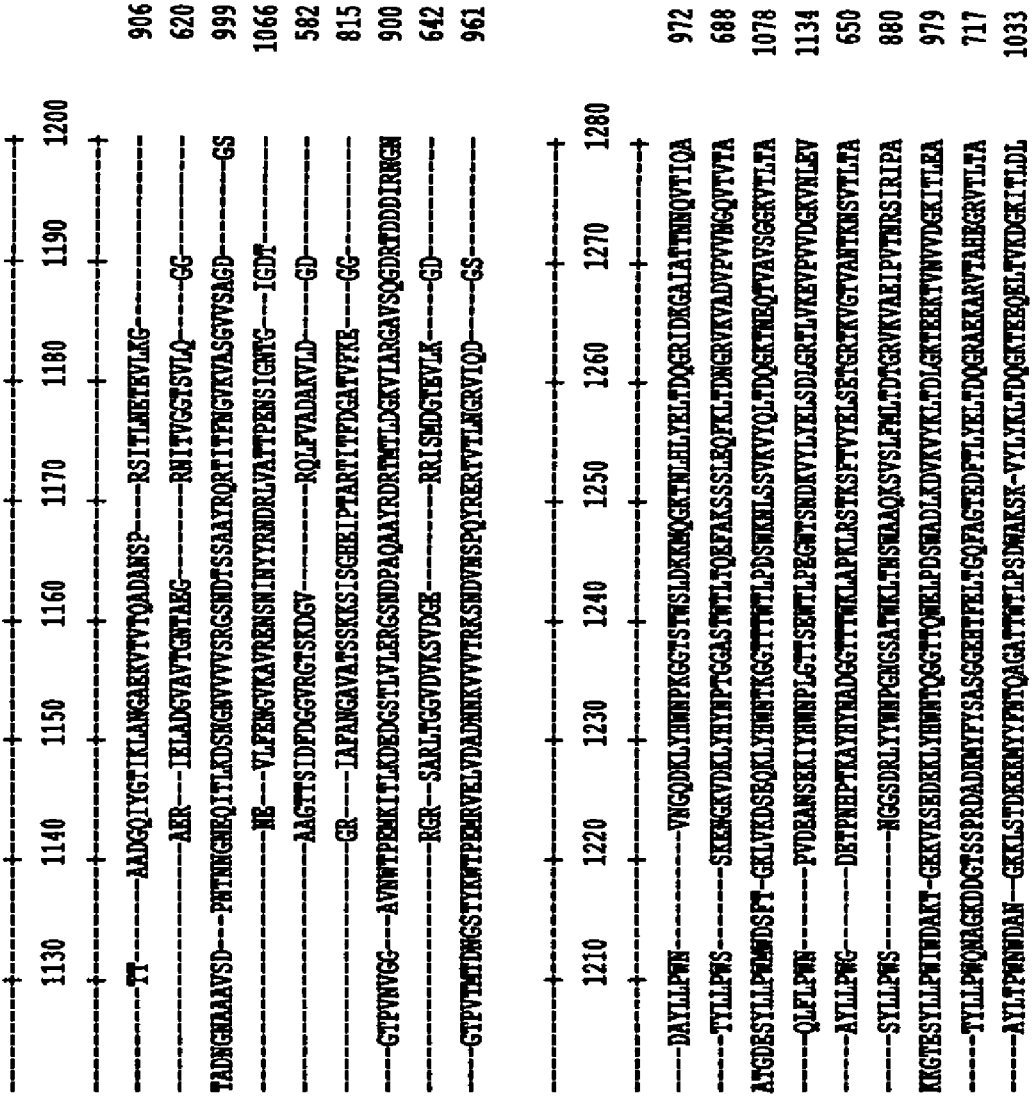
Figures 1, 1B, 2, 3, 4, 5, 6, 7, 8, 9:
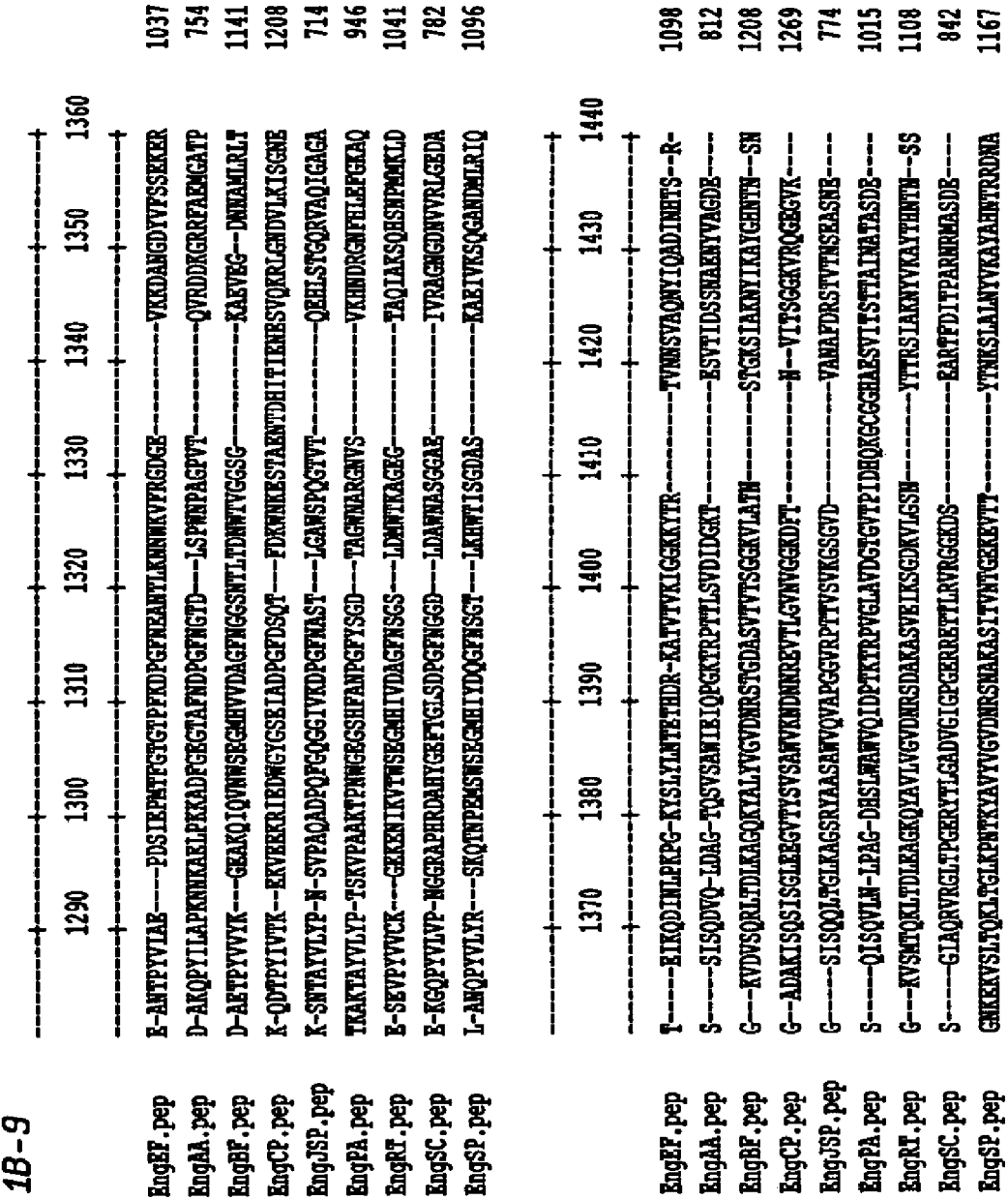
Figures 1, 1B, 2, 3, 4, 5, 6, 7, 8, 9, 10:
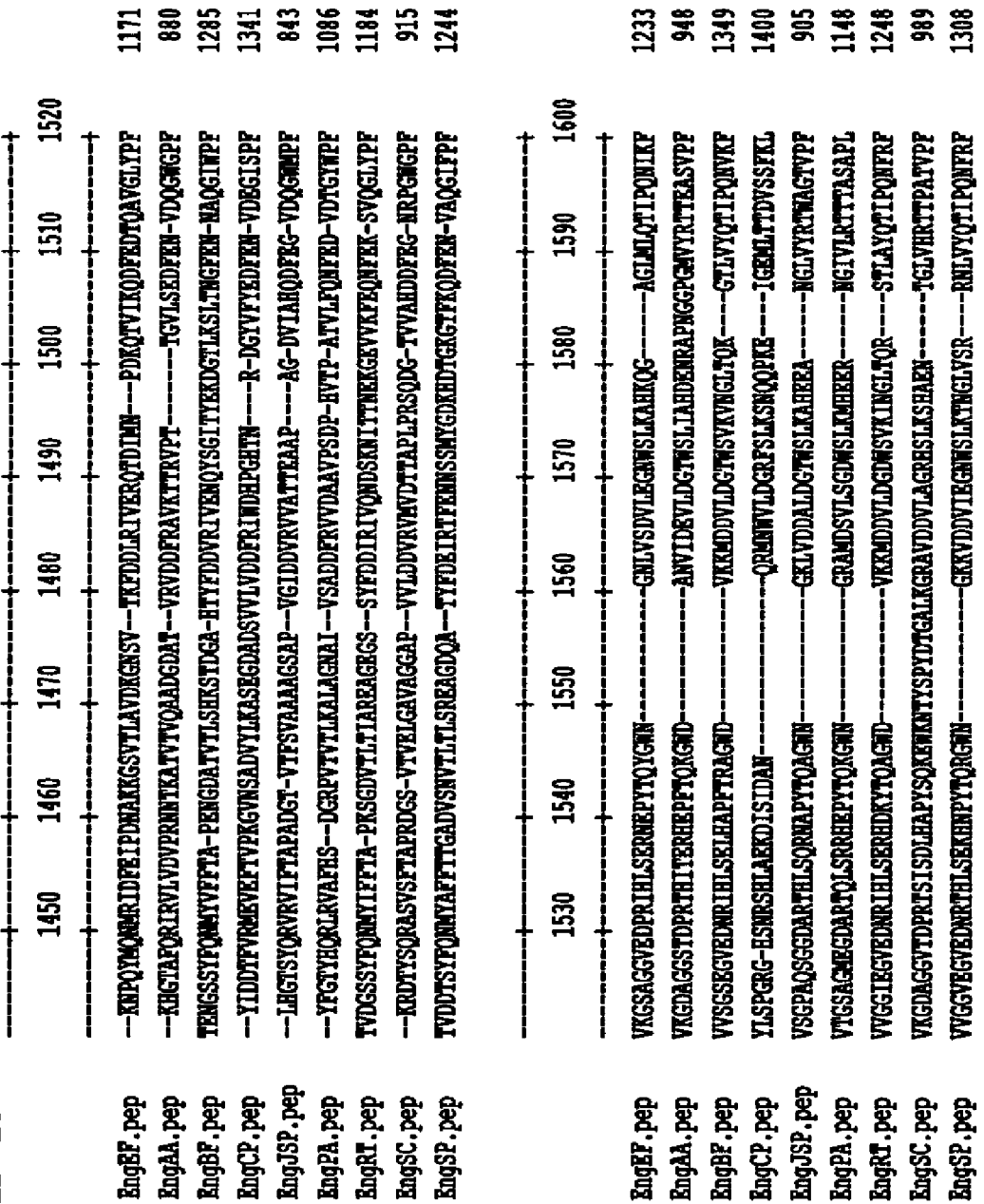
Figures 1, 1B, 2, 3, 4, 5, 6, 7, 8, 9, 10, 11:
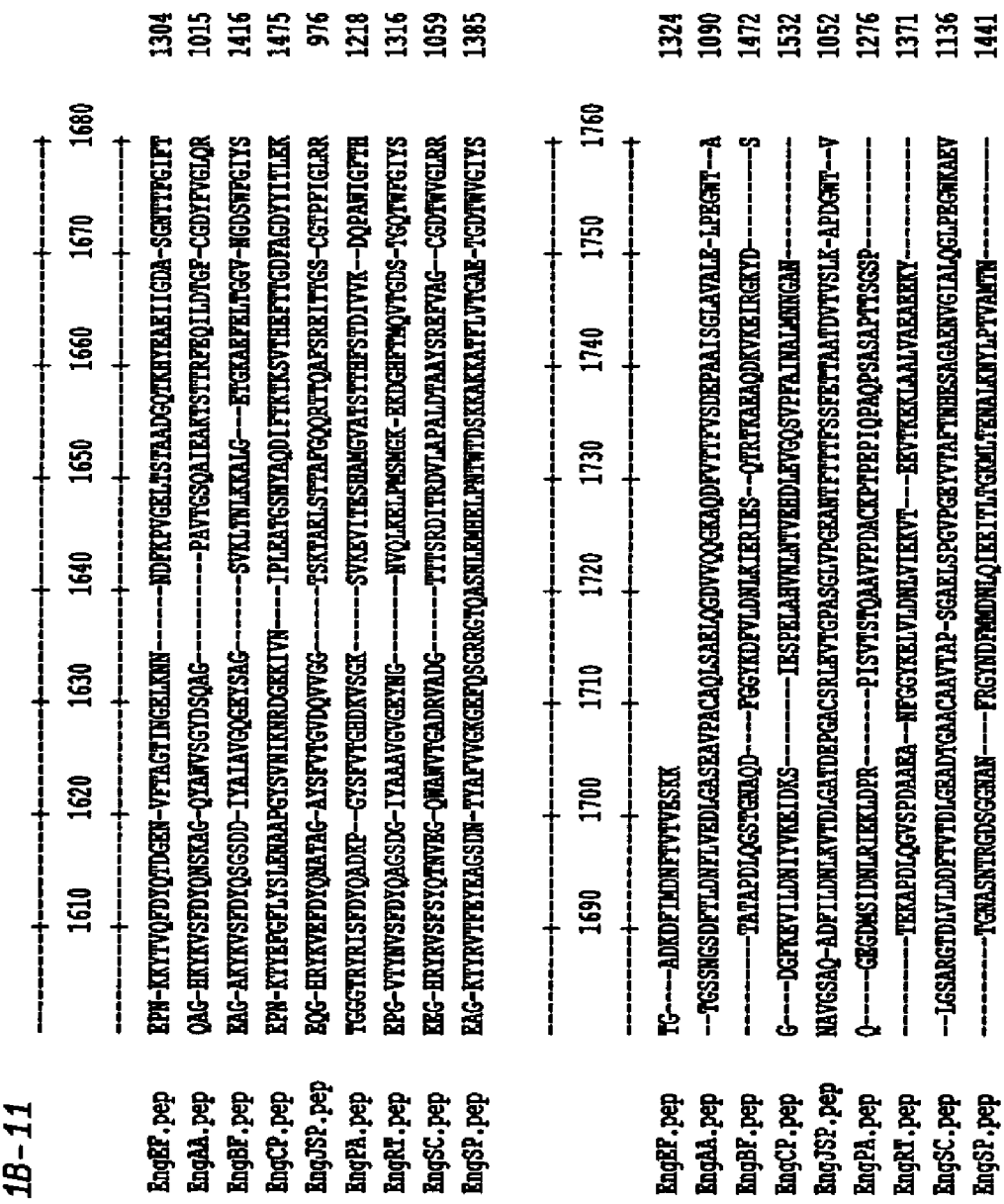
Figures 1, 1B, 2, 3, 4, 5, 6, 7, 8, 9, 10, 11, 12:
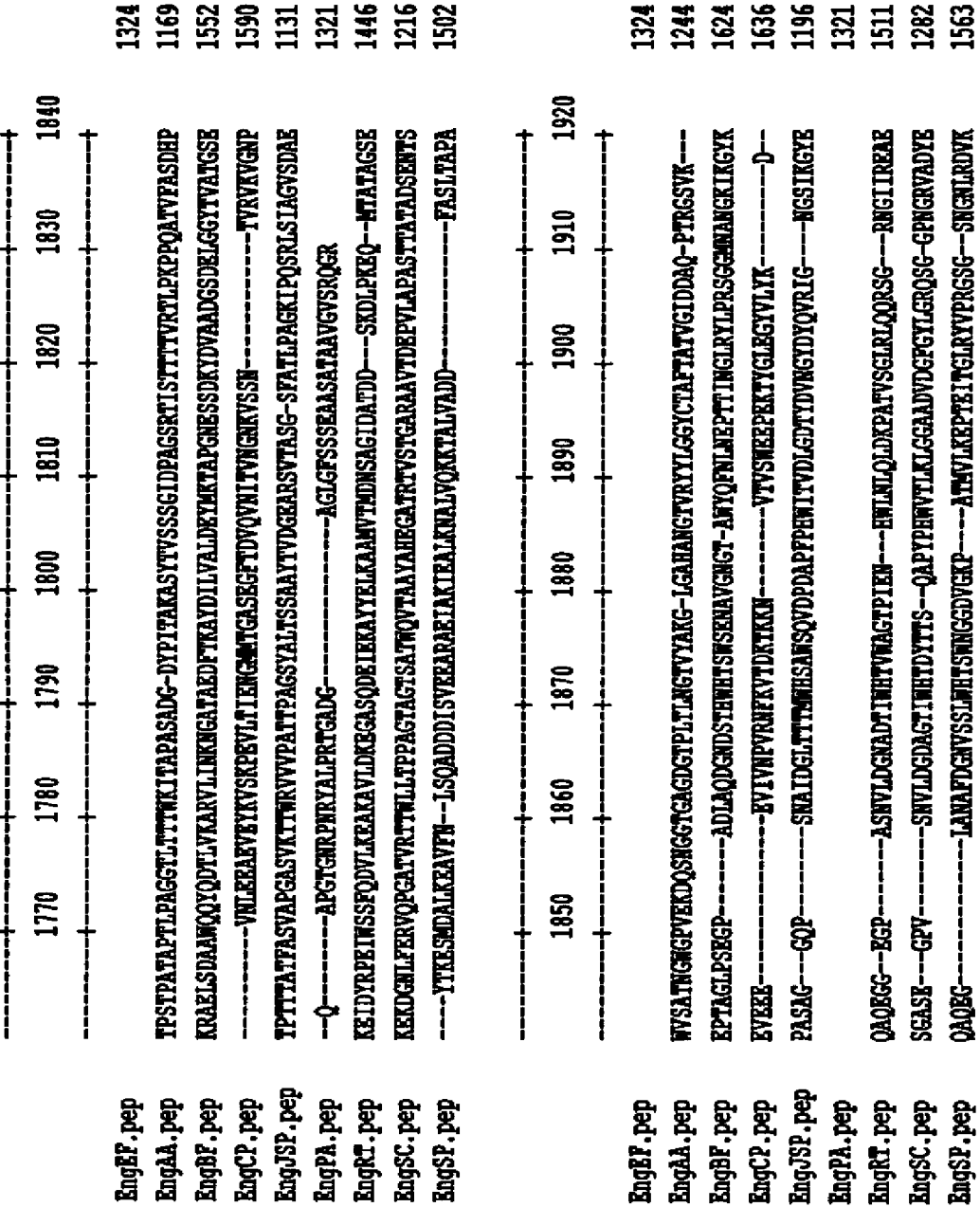
Figures 1, 1B, 2, 3, 4, 5, 6, 7, 8, 9, 10, 11, 12, 13, 14:
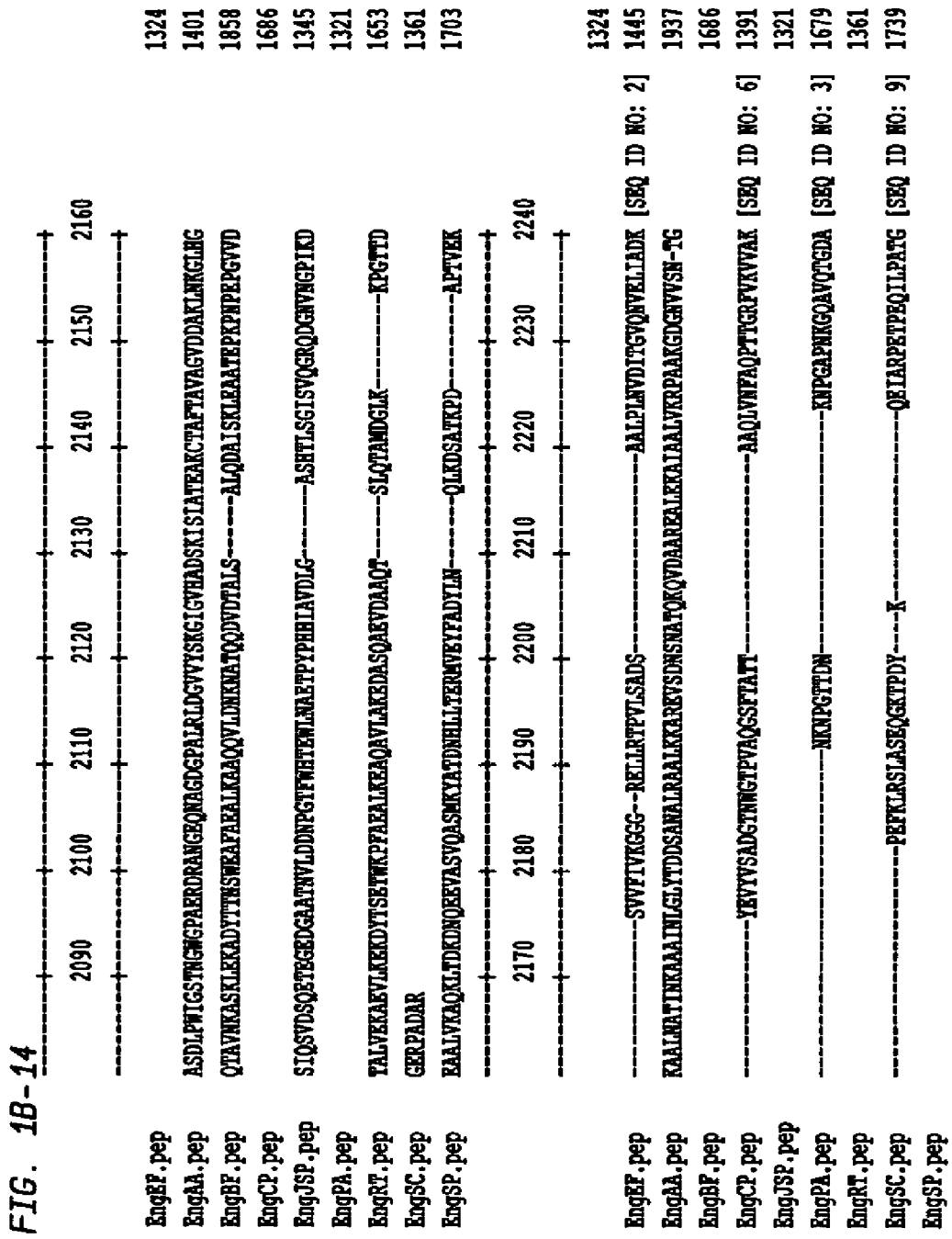
Figure 2:
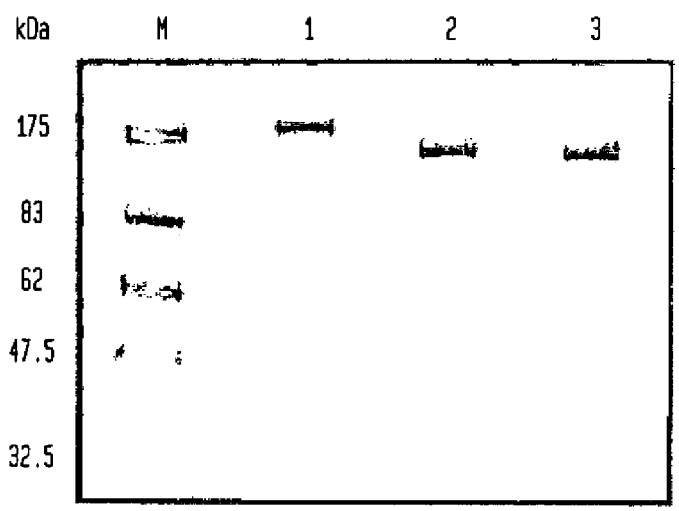
Figure 3:
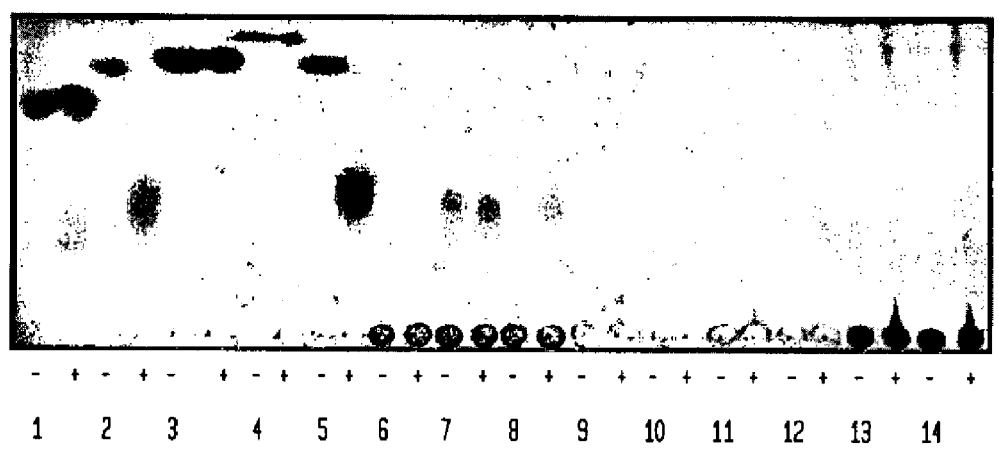

FIGS. 5-1 to 5-4 show a ClaustalW sequence comparison of EngEF (SEQ ID NO:2), EngPA (SEQ ID NO:3)and EngAA (SEQ ID NO:4), in which the conserved amino acid sequences that characterize the family of proteins of which the sequences are members, are highlighted. The grey box denotes the portion of the sequence that has been deleted in EngAA*.

DETAILED DESCRIPTION OF EMBODIMENTS

A family of novel O-linked glycosidases, which have broad enzyme specificity against Core 1 and Core 3 O-linked glycans, are described here. One or more of the following features can characterize these enzymes:

(a) A sequence homology with EngBF as determined by a BLAST search in which the Expectation value is less than $e^{-10}$ more specifically less than $e^{-20}$;

(b) VDWQDAA (SEQ ID NO: 1);

(c) a C-terminal domain of no more than 200 amino acids measured from FDY in the central conserved region (see the grey shaded boxes in FIG. 1); and (d) a length of no more than 1400 amino acids in length. In addition to the above features, the family of glycosidases generally lacking any carbohydrate-binding domain (CBD).

A novel family of glycosidases have been cloned, purified and tested here. These enzymes possess both Core 3 and Core 1 O-glycan cleavage activity as demonstrated (see Tables I and II), for example, using Galβ1,3GalNAcα1pNP and GlcNAcβ1,3GalNAcα1pNP substrates as well as natural glycoproteins containing O-linked glycans that had been pretreated with a neuraminidase. O-glycosidase activity generally refers to endo-α-N-acetyl galactosaminidase activity (endo-α-GalNAcase). Additional members of the family may be identified by means of a BLAST (Altschul et al. *Nucleic Acids Res*. 25:3389-3402 (1997)) search using the open reading frame for EngEF or EngPA as described in Example 1.

Examples of this family of O-glycosidases include EngEF, EngPA and a truncated EngAA (after removal of the two terminal CBDs). The amino acid sequences for these glycosidases are provided in FIG. 5 and in FIG. 1B, which also provides sequences for glycosidases with specificity for Core 1 O-linked glycans, demonstrated by cleavage with Galβ1, 3GalNAcα1pNP. FIG. 1A shows a cartoon describing the relative positions of the central conserved domains and the CBDs.

The glycosidases within the newly characterized family share a larger conserved region beyond required specific sequences as shown in FIG. 1A. The central conserved domain is characterized by an overall % sequence identity of at least 4% greater than that observed for total protein (see Table III).

The glycosidic activity profile of the newly described O-glycosidases makes these enzymes a powerful tool for the release of O-glycan sugars from glycoproteins.

In addition to glycosidic activity, the glycosidases were also tested for transglycosylation activity. Transglycosylation can be achieved using a glycosidase to attach a monosaccharide or disaccharide to a substrate. This can be achieved by driving the glycosidic reaction backwards in the presence of an excess of end product more particularly an excess of a disaccharide containing Core 1 or Core 3 glycans. When incubated in the presence of Galβ1,3GalNAcα1pNP and several 1-alkanols, transglycosylation products could be detected up to 1-pentanol (FIGS. 4A and 4B) using the novel family of Endo-α-GalNAcases with a broad substrate specificity described here. A similar activity profile was observed using GlcNAcβ1,3GalNAcα1pNP as a donor and 1-alkanols as acceptors.

The references cited herein, as well as U.S. Provisional Application No. 61/046,129 filed Apr. 18, 2008, are incorporated by reference.

EXAMPLES

Abbreviations

Endo-α-GalNAcase: endo-α-N-acetylgalactosaminidase or O-glycosidase; pNP: p-nitrophenol; TLC: thin layer chromatography; CBD: carbohydrade-binding domain; SBD: sugar-binding domain; Galβ1,3GalNAc: galactopyranosyl-β1,3-N-acetyl-D-galactosamine pyranoside; GlcNAcβ1, 3GalNAc: N-acetyl-D-glucosaminepyranosyl-β1,3N-acetyl-D-galactosamine pyranoside; ORF: open reading frame; PCR: polymerase chain reaction.

Example 1

Endo-α-GalNAcases with a Broad Substrate Specificity

A BLAST search (Altschul et al. *Nucleic Acids Res*. 25:3389-3402(1997)) was performed using the EngBF protein sequence as a template. In this search, four potential glycosidases were selected from the BLAST results at a cut off expectation value of less than $e^{-10}$ (and as low as $2e^{-96}$) and were cloned, purified and characterized. Two of these glycosidases were found to release Core 1 and Core 3 type O-glycans and a third was found to be a candidate for this activity if the sugar-binding domains were removed.

The structural and functional features of 4 endo-α-GalNAcases were compared (FIG. 1A). These were (1) NP_815498.1 of *Enterococcus faecalis* (EngEF) (2) YP_056270.1 of *Propionibacterium acnes* (EngPA) that has an F5_F8 type C domain (member of the galactose-binding domain-like superfamily) close to the N-terminus, (3) YP_947239.1 of *Arthobacter aurescens* (EngAA) that has two NPCBM domains (novel putative carbohydrate-binding module) at the C-terminus and (4) YP_695137.1 of *Clostridium perfringens* (EngCP) that has a CBM4_9 domain.

Example 2

Cloning and Expression of the E. faecalis Endo-α-GalNAcase Gene (engEF)

Based on the DNA sequence NP_815498.1 of *Enterococcus faecalis*, an oligonucleotide primer pair EFfor-NdeI (5'-CCCATATGAAACATGGAAAAATAAAAC-GATTTAGTAC-3' (SEQ ID NO:11), NdeI restriction site underlined) and EFrev-XhoI (5'-CCCTC-GAGTTTTTTTGATTCCA CTGTGACCGTAAAG-3' (SEQ ID NO:12), XhoI restriction site underlined) was designed. The putative endo-α-GalNAcase gene was amplified by PCR using these primers and genomic DNA of *E. faecalis* ATCC 700802 as the template. The PCR reaction mixture was incubated in an Applied Biosystems (Foster City, Calif.) thermal cycler (model 2720) for 30 cycles of 98° C. for 10 sec, 56° C. for 30 sec and 72° C. for 2 min. The amplified product was isolated by agarose gel electrophoresis, gel purified using QIAEX (Qiagen, Valencia, Calif.) and digested with NdeI and XhoI (New England Biolabs, Inc., Ipswich, Mass.). The resulting NdeI/XhoI fragment was inserted into an appropriate vector, in this case the pET-21a vector (Novagen, EMD Chemicals, Inc., Gibbstown, N.Y.) previously digested with these enzymes. The ligation mixture was used to transform competent bacterial cells resulting in plasmid pET21a-engEF. Plasmid pET21a-engEF was introduced into T7 Express lysY *E. coli* strain (New England Biolabs, Inc., Ipswich, Mass.). The transformed cells were grown overnight at 30° C. with agitation in 20 ml LB medium (10 g/l tryptone, 5 g/l yeast extract, 10 g/l NaCl, 1 g/l dextrose, 1 g/l MgCl$_2$) containing 100 µg/ml ampicillin. This culture was used to inoculate 1000 ml of fresh medium and antibiotics. The incubation temperature was shifted at 25° C. and when the cultures reached an A600 of 0.6-0.7, isopropyl thio-β-D-galactopyranoside at 0.3 mM was added. Incubation continued for 12-14 h at 20° C. The cells were harvested by centrifugation (5.000 g for 20 min) and stored frozen at −70° C.

Example 3

Cloning and Expression of the C. perfringens Endo-α-GalNAcase Gene (engCP)

Based on DNA sequence of YP_695137.1 of *C. perfringens*, an oligonucleotide primer pair CPfor-NdeI (5'-CC CATATGGGTAGAAAATGCATGAATAAGAAGATTG-3' (SEQ ID NO:13), NdeI restriction site underlined) and CPrev-XhoI (5'-CC CTCGAGTCTAGCAGTTCTAACAGTTATTGATTCCT TAG-3' (SEQ ID NO:14), XhoI restriction site underlined) was designed. The putative endo-α-GalNAcase gene was amplified by PCR using these primers and genomic DNA of *C. perfringens* ATCC 13124 as the template and the amplification conditions described in Example 2. The amplified gene was cloned and expressed as described in Example 2.

Example 4

Cloning and Expression of the P. acnes Endo-α-GalNAcase Gene (engPA)

Based on DNA sequence of YP_056270.1 of *P. acnes*, the putative endo-α-GalNAcase gene was chemically synthesized. The codons were optimized for gene expression in *E. coli* using DNAWorks software (Hoover and Lubkowski *Nucleic Acids Res*, 30, e43 (2002)). The optimized sequence was divided into six building blocks and synthesized (Hoover and Lubkowski *Nucleic Acids Res*, 30, e43 (2002)). After the sequence of each block was verified, the full sized gene was assembled using the USER method (Bitinaite et al. *Nucleic Acids Res*. 35:1992-2002 (2007)). Once assembled the synthesized engPA gene was amplified by PCR using the primer pair PA for (5'-GGAGACAUCCATATGAGTCGCACCC-3') (SEQ ID NO:15) and PArev (5'-GGGAAAGUTTAACGAC-CTTGACGTGAAAC-3') (SEQ ID NO: 16) and inserted into the corresponding sites of pNEB206A using the USER™ Friendly Cloning Kit (New England Biolabs, Inc., Ipswich, Mass.). The resulting plasmid pNEB206A-engPA was transformed and expressed as previously described in Example 2.

Example 5

Cloning and Expression of the Truncated A. aurescens Endo-α-GalNAcase Gene (EngAA*)

Based on DNA sequence of YP_947239.1 of *A. aurescens*, an oligonucleotide primer pair AAUR-noNPCBM-NdeI (5'-CCCCCCCATATGCCCCGCTTGTCATCCC-3' (SEQ ID NO:17), NdeI restriction site underlined) and AAUR-noN-PCBM-HindIII (5'-CCCCCC AAGCTTCAGCGTCCGCACGGTG-3' (SEQ ID NO:18), HindIII restriction site underlined) was designed to remove the signal sequence from the N-terminus of the protein and the two NPCBM domains at the C-terminus. The truncated endo-α-GalNAcase gene (EngAA*) was amplified by PCR using these primers and genomic DNA of *A. aurescens* TC1 as the template. The PCR reaction mixture was incubated in an Applied Biosystems thermal cycler (model 2720) (Foster City, Calif.) for 30 cycles at 98° C. for 10 sec, and 72° C. for 1 min 40 sec. The amplified product was isolated by agarose gel electrophoresis, gel purified using QIAEX (Qiagen, Valencia, Calif.) and digested with NdeI and HindIII (New England Biolabs, Inc., Ipswich, MA). The resulting NdeI/HindIII fragment was inserted into an appropriate vector, in this case the pET-21a vector (Novagen, EMD Chemicals, Inc., Gibbstown, N.Y.) previously digested with these enzymes. The ligation mixture was used to transform competent bacterial cells resulting in plasmid pETAAUR_1465. The plasmid pETAAUR_1465 was introduced into SHuffle™ T7 Express LysY Competent *E. coli* (New England Biolabs, Inc., Ipswich, Mass.). The transformed cells were grown overnight at 30° C. with agitation in 2 ml LB medium (10 g/l tryptone, 5 g/l yeast extract, 10 g/l NaCl, 1 g/l dextrose, 1 g/l MgCl2) containing 100 µg/ml ampicillin. This culture was used to inoculate 100 ml of fresh medium and antibiotics. When the cultures reached an A600 of 0.5-0.6, isopropyl thio-β-D-galactopyranoside at 0.8 mM was added. Incubation continued for 4 h at 30° C. The cells were harvested by centrifugation (5.000 g for 20 min) and stored frozen at −20° C.

Example 6

Method for Purification of the Expressed Endo-α-GalNAcase EngEF

All procedures were performed either on ice or at 4° C. Ten grams of frozen cells obtained above were thawed in 30 ml of 20 mM Tris-HCl pH 7.6, 200 mM NaCl, 1 mM dithiothreitol and were sonicated (6×20 sec with 30 sec intervals) using a Sonicator Ultrasonic processor model-375 (Misonix, Inc., Farmingdale, N.Y.). Sample was subsequently centrifuged at 10,000 g for 15 min and the supernatant was collected for further purification.

The cell extract was diluted 3 fold with a buffer containing 20 mM Tris-HCl pH 7.6 (buffer A), applied onto a HisTrap™ Q HP column (GE Healthcare Bio-Sciences Corp., Piscataway, N.J.) previously equilibrated in Buffer A and eluted with a linear gradient of 0-1 M NaCl in Buffer A. Fractions containing the enzyme were eluted in ~0.2-0.75 M NaCl from the column. These fractions were applied to a HisTrap™ HP column (GE Healthcare Bio-Sciences Corp., Piscataway, N.J.) previously equilibrated with Buffer B (20 mM Tris-HCl pH 7.6, 500 mM NaCl), followed by elution with a linear gradient of 0-0.5 M imidazole in Buffer B. The enzyme was eluted at the concentration range of 0.06-0.27 M imidazole. These fractions were combined, dialyzed overnight against Buffer A and subsequently applied onto a Source 15Q column (GE Healthcare Bio-Sciences Corp., Piscataway, N.J.) previously equilibrated in Buffer A. Proteins were eluted with a linear gradient of 0.1-0.23 M NaCl in Buffer A. Active EngEF were eluted in 0.14-0.18 M NaCl fractions, which were then combined and concentrated with a Amicon Centricon Concentrator 10 (Millipore, Billerica, Mass.) to about 5 ml. Concentrated samples were loaded onto a Superdex 75 column previously equilibrated with Buffer C (20 mM Tris-HCl pH 7.6, 200 mM NaCl), and washed with Buffer C; and fractions with EngEF activity were pooled and concentrated. After the addition of glycerol at 50%, the purified enzyme preparation was stored at −20° C. Enzyme purity was judged by gradient polyacrylamide gel electrophoresis under denaturing conditions (Laemmli *Nature* 227:680-685 (1970)). Protein concentration was determined using Bradford's dye binding assay (Bio-Rad Laboratories, Hercules, Calif.) (Bradford *Anal Biochem.* 72:248-254 (1976)) with bovine serum albumin as the protein standard.

Example 7

Method for Purification of the Expressed Endo-α-GalNAcase EngCP

All procedures were performed either on ice or at 4° C. Ten grams of frozen cells obtained above were thawed in 30 ml of 20 mM Tris-HCl pH 7.6, 200 mM NaCl, 1 mM dithiothreitol and were sonicated (6×20 sec with 30 sec intervals) using a Sonicator Ultrasonic processor model-375 (Misonix, Farmingdale, N.Y.). Sample was subsequently centrifuged at 10,000 g for 15 min and the supernatant was collected for further purification.

The cell extract was diluted 3 fold with Buffer A, applied onto a (GE Healthcare Bio-Sciences Corp., Piscataway, N.J.) 15Q column previously equilibrated in the same buffer and eluted with a linear gradient of 0-1 M NaCl in Buffer A. Fractions in ~0.3-0.45 M NaCl containing the enzyme were eluted from the column and applied onto a HisTrap™ HP column (GE Healthcare Bio-Sciences Corp., Piscataway, N.J.) previously equilibrated with buffer B, followed by elution with a linear gradient of 0-0.5 M imidazole in buffer B. The enzyme was eluted in a concentration range of 0.12-0.19 M imidazole. These fractions were combined, dialyzed overnight against Buffer D (20 mM Sodium acetate pH 6.0) and subsequently applied onto a Source 15S column (GE Healthcare Bio-Sciences Corp., Piscataway, N.J.) previously equilibrated in Buffer D. Proteins were eluted with a linear gradient of 0-1 M NaCl in Buffer D. Active EngCP (corresponding to 0.45-0.60 M NaCl) fractions were combined and concentrated with a Amicon Centricon Concentrator 10 (Millipore, Billerica, Mass.) to about 5 ml. Concentrated samples were loaded onto a Superdex 75 column previously equilibrated with Buffer E (20 mM Sodium acetate pH 6.0, 200 mM NaCl), and washed with Buffer E; and fractions with EngCP activity were pooled and concentrated. After the addition of glycerol at 50%, the purified enzyme preparation was stored at -20° C.

Example 8

Method for Purification of the Expressed Endo-α-GalNAcase EngPA

All procedures were performed either on ice or at 4° C. Ten grams of frozen cells obtained above were thawed in 30 ml of 20 mM Tris-HCl pH 7.6, 200 mM NaCl, 1 mM dithiothreitol and were sonicated (6×20 sec with 30 sec intervals) using a Sonicator Ultrasonic processor model-375 (Misonix, Inc., Farmingdale, N.Y.) he supernatant was collected for further purification.

The cell extract was diluted 3 fold with Buffer A, applied to a Source 15Q column (GE Healthcare Bio-Sciences Corp., Piscataway, N.J.) previously equilibrated in the same buffer and collected in the flow through where most EngPA was detected. The fractions were dialyzed against Buffer D. The dialyzed sample was applied onto a Source 15S column (GE Healthcare Bio-Sciences Corp., Piscataway, N.J.) previously equilibrated in Buffer D, followed by elution with a linear gradient of 0-1 M NaCl in Buffer D. Active EngPA (corresponded to 0.31-0.36 M NaCl) fractions were combined, concentrated (5 ml) and loaded onto a Superdex 75 column previously equilibrated with Buffer E. Column was washed with Buffer E and fractions with EngPA activity were pooled and concentrated. After the addition of glycerol at 50%, the purified enzyme preparation was stored at −20° C.

Example 9

Method for Purification of the Expressed Truncated Endo-α-GalNAcase EngAA*

All procedures were performed either on ice or at 4° C. 1 gram of frozen cells obtained above were thawed in 10 ml of 50 mM Tris-HCl pH 7.5, 50 mM NaCl, 1 mM EDTA, 0.2 mM PMSF and were sonicated (5×20 sec with 30 sec intervals) using a Sonicator Ultrasonic processor model-375 (Misonix, Inc., Farmingdale, N.Y.). Sample was subsequently centrifuged at 20,000 g for 20 min and the supernatant was discarded.

The pellet containing the inclusion bodies was washed two times by resuspending the pellet in 50 mM Tris-HCl pH 8.0, 200 mM NaCl, 1% Triton-X100 by vortexing and centrifuged at 20.000 g for 20 min. The resulting pellet was resuspended in 5 ml Buffer B +PMSF (100 mM $NaPO_4$, 10 mM Tris-HCl, 8 M Urea, 0.2 mM PMSF, pH 8.0). This suspension was incubated slowly rotating at 25° C. to solubilze the protein pellet for 1.5 hr. After incubation the protein suspension was diluted with 10 ml of Buffer B. The sample was dialyzed overnight at 4° C. against 2 liters of 100 mM $NaH_2PO_4$, 10 mM Tris-HCl pH 8.0. The next day any insoluble material was removed by centrifugation at 20,000 g for 20 min. The buffer of the solubilzed protein (the supernatant) was exchanged and concentrated to 2 ml using a 5 KD Amicon filter (Millipore, Billerica, Mass.) with two washes of 50 mM $NaPO_4$, 5 mM $MgCl_2$, pH7.5. After the addition of glycerol at 50%, the partially purified enzyme preparation was stored at −20° C.

Example 10

Characterization of Endo-α-GalNAcase Activity a) Substrate specificity on pNP substrates The hydrolytic activity of the the purified enzymes EngCP, EngEF, EngPA and the commercially available EngSP and EngAL were assayed using Galβ1,3GalNAcα1pNP (Core 1), GlcNAcβ1,3GalNAcα1pNP (Core 3), Galβ1,3(GlcNAcβ1,3)GalNAcα1pNP (Core 2), Galβ1, 3GlcNAcα1pNP and GalNAcα1pNP as substrates and the released sugars were detected by colorimetric assay (Table I). Partially purified EngAA* was assayed using Galβ1, 3GalNAcα1pNP (Core 1), GlcNAcβ1,3GalNAcα1pNP (Core 3), Galβ1,3(GlcNAcβ1,3)GalNAcα1pNP (Core 2) (Table I). The standard reaction mixture contained in a total volume of 100 μl, 50 mM sodium phosphate buffer pH 7.5, 5 mM $MgCl_2$ and 0.25 mM substrate. The released p-nitrophenol (pNP) was monitored by a 96-well plate reader (SpectraMax M5, Molecular Devices, Inc., Sunnyvale, Calif.) at 405 nm at room temperature. Galβ1,3GalNAcα1pNP was hydrolyzed at the most rapid rate by all enzymes tested. After a 16 h incubation, EngEF, EngPA and EngAA* were the only enzymes capable of fully hydrolyzing the Core 3 disaccharide (GlcNAcβ1,3GalNAcα1pNP). EngAL could partially hydrolyze it (27%) (Table I). EngAL could also partially release GalNAc while the rest of the enzymes released only traces of the monosaccharide (Table I). None of the enzymes tested could act on Galβ1,3GalNAcα1pNP and only EngAA* had significant activity that was detected when Core 2 trisaccharide was used as substrate (Galβ1,3(GlcNAcβ1,6)GalNAcα1pNP) (Table I).

b) Substrate specificity on pNP and glycoproteins using TLC

The substrate specificity was also determined for EngEF on TLC using various pNP glycosides and natural glycoproteins. Galβ1,3GalNAcα1pNP, GlcNAcβ1, 3GalNAcα1pNP, Galβ1,3GalNAcα1pNP, GalNAcα1pNP, calf k-casein, human glycophorin A, porcine mucin, calf fetuin, and calf asialofetuin were purchased from Sigma Alrich (St. Louis, Mo.). Galβ1,3(GlcNAcβ1,6)GalNAcα1pNP was from Toronto Research Chemicals Inc. (North York, Ontario, Canada). For thin layer chromatography (TLC) analysis, a Silica Gel 60 plate (Merck, Whitehouse Station, N.J.) was developed in a solvent system of chloroform/methanol/water, 3/3/1 (v/v/v), and the sugars were visualized by spraying diphenylamine/aniline/phosphate reagent (Bailey and Bourne *J Chromatogr.* 4:206-213 (1960)).

Calf K-casein, human glycophorin A, porcine mucin, calf fetuin, and calf asialofetuin were incubated with EngEF. Based on the TLC analysis, sugars were only released when asialofetuin and mucin were used as substrates (FIG. 3). Co-incubating the substrates with neuraminidase increased the ability of the enzyme to release sugars. The released sugars migrated at the same height on the TLC plate as the Core 1 and 3 disaccharides (FIG. 3).

c) Optimum pH

The pH dependence of enzyme activity was determined for EngEf, EngCP and EngPA in pH range 2.0-9.0 using the following buffers (50 mM): glycine-HCl (2.0-4.0), sodium acetate (3.5-6.0), sodium phosphate (5.5-8.0), and Tris-HCl (7.0-9.0). The pH dependence can be similarly determined for EngAA*.

d) Steady-state enzyme kinetics

Glycosidases purified as described above were used for the kinetics measurements for EngEF, EngCP and EngPA. Endo-α-GalNAcases from *Streptococcus pneumoniae* (EngSP) and *Alcaligenes* sp. (EngAL) were purchased from Roche (Basel, Switzerland) and Seikagaku Corporation (Tokyo, Japan), respectively. Steady-state enzyme kinetics were performed at 25° C. The program HYPER v 1.01 was used to determine $V_{max}$ and $K_m$ values. The $k_{cat}$ values were calculated from $V_{max}$ using a molecular mass of 188000 Da for EngCP, 147000 Da for EngEF, 142000 Da for EngPA, 190000 Da for EngSP and 160000 Da for EngAL. Reported values were the average of three measurements. The standard deviations did not exceed 5%.

The enzyme kinetics of EngCP, EngEF, EngPA, EngSP and EngAL was measured using Galβ1,3GalNAcα1pNP and GlcNAcβ1,3GalNAcα1pNP (Table II). When Galβ1, 3GalNAcα1pNP was used, EngEF exhibited the highest $k_{cat}$ and EngPA had the lowest, about 25 times lower than EngEF activity. In the case of GlcNAcβ1,3GalNAcα1pNP, the kinetic parameters could be measured only for EngPA and EngEF. EngPA was more active than EngEF and had 3 times higher $k_{cat}$. The enzyme kinetics can be similarly determined for EngAA*.

e) Transglycosylation activity

The transglycosylation reaction mixture contained in a total volume of 15 μl, 50 mM sodium phosphate buffer pH 7.5, 5 mM $MgCl_2$, 0.8 mM GlcNAcβ1,3GalNAcα1pNP or 1.6 mM Galβ1,3GalNAcα1pNP as substrates, 0.8 μg of endo-α-GalNAcase, and various 1-alcanols as acceptors (13%, v/v) at room temperature for 16 h. Methanol, ethanol, 1-propanol, 1-butanol, 1-pentanol, 1-hexanol, 1-heptanol, 1-octanol and 1-nonalol were purchased from Sigma Aldrich (St. Louis, Mo.). The transglycosylation reaction mixtures were analyzed on a Silica Gel 60 TLC plate using chloroform/methanol/water 65/35/8 as the developing solvent and the sugars were visualized by spraying diphenylamine/aniline/phosphate reagent.

Figure 4A:
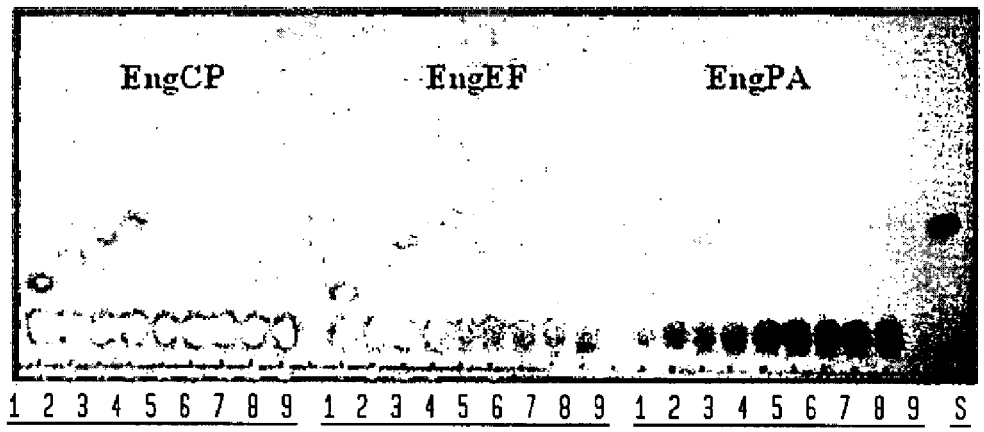
Figure 4B:
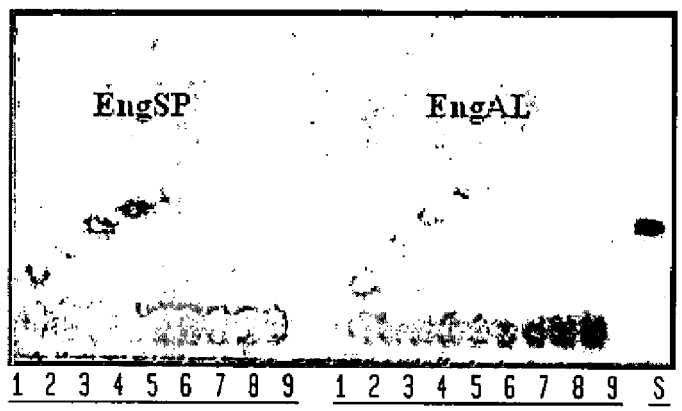
Figure 4C:
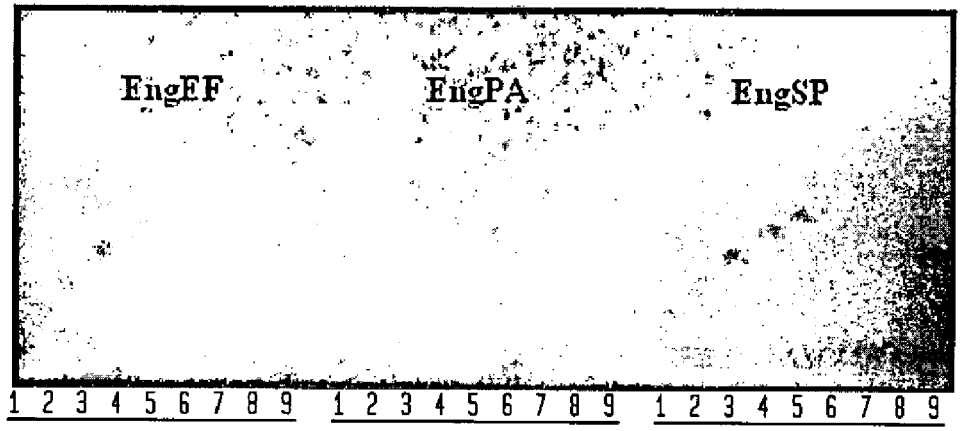

EngCP, EngEF, EngPA, EngSP and EngAL all exhibited similar transglycosylation activity. The transglycosylation products could be detected up to 1-pentanol (FIGS. 4A and 4B). While EngEF and EngPA which were capable of fully hydrolyzing GlcNAcβ1,3GalNAcα1pNP compared to the quite low activity of the rest of the endo-α-GalNAcases (Table I), no significant difference was observed in the transglycosylation products using EngEF, EngPA and EngSP with GlcNAcβ1, 3GalNAcα1pNP as donor and 1-alkanols as acceptors (FIG. 4C). The transglycosylation activity can be similarly determined for EngAA*.

TABLE I

Substrate specificity using pNP substrates

|  | Eng CP | Eng EF | Eng PA | Eng SP | Eng AL | Eng AA* |
|---|---|---|---|---|---|---|
|  | % product released | | | | | |
| Galβ1,3GalNAcα1pNP Core 1 | 100 | 100 | 100 | 100 | 100 | 100 |
| Galβ1,3(GlcNAcβ1,6)GalNAcα1pNP Core 2 | 2.5 | 2 | 0 | 0.6 | 0 | 24 |
| GlcNAcβ1,3GalNAcα1pNP Core 3 | 6 | 100 | 100 | 3 | 27 | 100 |
| Galβ1,3GlcNAcα1pNP | 0 | 0 | 0 | 0 | 0 | NT |
| GalNAcα1pNP | 4.4 | 2.2 | 1.8 | 1.2 | 30 | NT |

Reaction mixtures were incubated with the different endo-α-GalNAcases at 25° C. for 16 h. Product release was measured at 405 nm. NT=not tested.

*Data from Fujita et al. *J Biol Chem.* 280:37415-37422 (2005).

TABLE II

Kinetic parameters of endo-α-GalNAcases using Galβ1,3GalNAcα1pNP (Core 1) and GlcNAcβ1,3GalNAcα1pNP (Core 3) as substrates

| Core 1 | $k_{cat}$ (1/sec) | $K_m$ (μM) |
|---|---|---|
| EngCP | 19.9 | 70.93 |
| EngEF | 51.17 | 47.85 |
| EngPA | 2.009 | 3.781 |
| EngSP | 10.51 | 40.37 |
| EngAL | 25.89 | 33.87 |
| EngBF # | 17.8 | 21.8 |

| Core 3 | $k_{cat}$ (1/sec) | $K_m$ (mM) |
|---|---|---|
| EngEF | 9.434 | 20.03 |
| EngPA | 28.9 | 11.15 |

TABLE III

BESTFIT Analysis of endo-α-GalNAcases- % Identity and % Similarity

|  | Total Protein | | Conserved Region | |
|---|---|---|---|---|
| Proteins Compared | % Identity | % Similarity | % Identity | % Similarity |
| EngEF to EngPA | 35.2 | 43.8 | 39.2 | 47.6 |
| EngAA to EngEF | 38.7 | 47.0 | 44.1 | 52.4 |
| EngPA to EngAA | 44.9 | 51.8 | 50.2 | 56.8 |

SEQUENCE LISTING

<160> NUMBER OF SEQ ID NOS: 16

<210> SEQ ID NO 1
<211> LENGTH: 7
<212> TYPE: PRT
<213> ORGANISM: artificial
<220> FEATURE:
<223> OTHER INFORMATION: conserved sequence

<400> SEQUENCE: 1

Val Asp Trp Gln Asp Ala Ala
1               5

<210> SEQ ID NO 2
<211> LENGTH: 1324
<212> TYPE: PRT
<213> ORGANISM: Enterococcus faecalis

<400> SEQUENCE: 2

Met Lys His Gly Lys Ile Lys Arg Phe Ser Thr Leu Thr Leu Leu Ala
1               5                   10                  15

Ser Ala Thr Ile Leu Val Pro Leu Ser Ser Ala Glu Glu Thr Thr
            20                  25                  30

Asn Ser Ser Thr Glu Thr Ser Ser Ser Met Val Glu Pro Thr Ala Thr
            35                  40                  45

Glu Glu Lys Leu Trp Gln Ser Asp Phe Pro Gly Gly Lys Thr Gly Glu

-continued

```
                50                  55                  60
Trp Gln Asp Val Ile Gly Lys Thr Asn Arg Glu Leu Ala Gly Glu Ser
 65                  70                  75                  80
Leu Ala Ile Ser Arg Asp Ala Ala Gly Asn Asn Ala Val Ser Leu
                 85                  90                  95
Asn Leu Asp Ser Pro Lys Leu Ala Asp Gly Glu Val Glu Thr Lys Phe
                100                 105                 110
Lys Tyr Thr Ala Gly Ser Gly Arg Thr Gly Val Ile Ile Arg Gly Asn
                115                 120                 125
Thr Lys Asp Ser Trp Val Phe Val Gly Tyr Asn Ala Asn Gly Lys Trp
                130                 135                 140
Leu Val Glu Ser Pro Asn Ser Trp Asn Asp Ser Ile Ser Gly Pro Thr
145                 150                 155                 160
Leu Asn Glu Asp Thr Asn Tyr Leu Leu Lys Val Arg Tyr Val Gly Glu
                165                 170                 175
Lys Ile Thr Ile Trp Leu Asn Thr Thr Leu Ile Tyr Glu Gly Glu Pro
                180                 185                 190
Val Leu Ala Asn Gly Asp Lys Ile Pro Thr Glu Ala Gly His Val Gly
                195                 200                 205
Val Arg Leu Trp Tyr Asp Lys Lys Ile Val Asn Tyr Asp Tyr Phe Lys
                210                 215                 220
Asn Gly Pro Val Asp Ser Ile Pro Glu Ile Val Pro Glu Val Thr Gln
225                 230                 235                 240
Ile Ala Pro Val Lys Val Phe Thr Lys Ile Gly Val Ala Pro Lys Leu
                245                 250                 255
Pro Lys Gln Val Lys Val Thr Tyr Asn Thr Gly Lys Glu Ala Asn Glu
                260                 265                 270
Ala Val Arg Trp Asn Glu Ile Asp Pro Asp Ala Tyr Lys Glu Pro Gly
                275                 280                 285
Thr Phe Glu Val Asp Gly Thr Leu Glu Asn Thr Asn Ile Lys Ala Lys
                290                 295                 300
Ala Ser Ile Val Val Ala Lys Asp Asn Glu Ala Glu Lys Gly Asp Lys
305                 310                 315                 320
Ile Ser Ser Ala Asp Leu Thr Ala Val Val Asp Pro Gln Phe Pro Arg
                325                 330                 335
Ile Ile Arg Tyr Glu Asp Pro Gln Ser Asn Gln Val Ile Phe Asn Gly
                340                 345                 350
Gln His Glu Lys Ile Asp Gln Val Met Ile Asp Gly Lys Ala Tyr Lys
                355                 360                 365
Ala Thr Ala Glu Lys Gln Lys Ser Glu Ala Asn Gln Ala Val Tyr Asn
                370                 375                 380
Val Ala Val Pro Glu Ile Gly Leu Arg Phe Thr Thr Thr Leu Thr Val
385                 390                 395                 400
Ser Glu Gly Gln Glu Leu Ala Met Lys Leu Ser Asp Ile Arg Glu Glu
                405                 410                 415
Gly Thr Lys Ile His Thr Ile Ser Ile Pro Asn Gln Gly Leu Ile Ser
                420                 425                 430
Val Asn Ser Thr Asp Glu Gly Ala Thr Phe Ala Gly Val Val Met Asn
                435                 440                 445
Thr Gly Thr Asn Ala Asn Asn Gly Asn Lys Asn Gly Asp Thr Ile Gln
                450                 455                 460
Asp Leu Thr Thr Thr Ser Gln Glu Glu Thr Lys Lys Tyr Met Tyr Gly
465                 470                 475                 480
```

-continued

Phe Leu Asn Thr Ala Asn Tyr Ala Ala Ser Phe Trp Thr Asn Ala Tyr
            485                 490                 495

Gly Asp Gly Ser Val Asp Gly Ser Asp Asn Asn Arg Ile His Lys Gln
            500                 505                 510

Thr Lys Glu Ala Ala Thr Gly Phe Val Thr Thr Leu Ser Ser Gly Ala
            515                 520                 525

Trp Thr Tyr Arg Pro Phe Asp Ala Pro Glu Asp Tyr Thr Thr Gly Glu
            530                 535                 540

Thr Pro Glu Val Lys Val Lys Phe Ser Lys Asp Ser Asn Asp Asp Asn
545                 550                 555                 560

Arg Val Asp Trp Gln Asp Ala Ala Ile Gly Phe Arg Ser Ile Met Asn
            565                 570                 575

Asn Pro Met Gly Ala Glu Lys Val Pro Glu Leu Val Asn Gln Arg Ile
            580                 585                 590

Pro Phe Asn Phe Ala Ser Gln Ala Thr Asn Pro Phe Leu Val Thr Leu
            595                 600                 605

Asp Glu Ser Lys Arg Ile Tyr Asn Leu Thr Asp Gly Leu Gly Gln Met
            610                 615                 620

Asn Leu Leu Lys Gly Tyr Gln Asn Glu Gly His Asp Ser Ala His Pro
625                 630                 635                 640

Asp Tyr Gly Ala Ile Gly Gln Arg Pro Gly Gly Glu Gln Ala Leu Asn
            645                 650                 655

Gln Leu Ile Asp Glu Gly His Lys Leu Asn Ala Val Phe Gly Val His
            660                 665                 670

Ile Asn Asp Thr Glu Ser Tyr Pro Glu Ala Lys Gly Phe Asn Glu Glu
            675                 680                 685

Leu Val Asp Pro Thr Lys Arg Gly Trp Asp Trp Leu Asp Pro Ser Tyr
            690                 695                 700

Phe Ile Lys Gln Arg Pro Asp Thr Leu Ser Gly Arg Arg Tyr Glu Arg
705                 710                 715                 720

Phe Lys Glu Leu Lys Gln Lys Ala Pro Asn Leu Asp Tyr Ile Tyr Val
            725                 730                 735

Asp Val Trp Gly Asn Gly Glu Ser Gly Trp Ala Ser Arg Gln Leu
            740                 745                 750

Ser Lys Glu Ile Asn Ser Leu Gly Trp Phe Thr Thr Asn Glu Phe Pro
            755                 760                 765

Asn Ala Leu Glu Tyr Asp Ser Val Trp Asn His Trp Ser Ala Glu Lys
            770                 775                 780

Asp Tyr Gly Gly Thr Thr Lys Gly Phe Asn Ser Thr Ile Val Arg
785                 790                 795                 800

Phe Ile Arg Asn His Gln Lys Asp Thr Trp Ile Ile Ser Asp Asn Pro
            805                 810                 815

Leu Leu Gly Gly Ala Glu Phe Glu Ala Tyr Glu Gly Trp Val Gly Lys
            820                 825                 830

Thr Asn Phe Asn Thr Tyr Arg Gln Lys Thr Phe Ala Ile Asn Val Pro
            835                 840                 845

Thr Lys Phe Leu Gln His Tyr Gln Ile Thr Asn Trp Glu Thr Thr
            850                 855                 860

Ala Ala Asp Gly Gln Ile Tyr Gly Thr Ile Lys Leu Ala Asn Gly Ala
865                 870                 875                 880

Glu Lys Val Thr Val Thr Gln Ala Asp Ala Asn Ser Pro Arg Ser Ile
            885                 890                 895

```
Thr Leu Asn Glu Thr Glu Val Leu Lys Gly Asp Ala Tyr Leu Leu Pro
            900                 905                 910

Trp Asn Val Asn Gly Gln Asp Lys Leu Tyr His Trp Asn Pro Lys Gly
        915                 920                 925

Gly Thr Ser Thr Trp Ser Leu Asp Lys Lys Met Gln Gly Lys Thr Asn
        930                 935                 940

Leu His Leu Tyr Glu Leu Thr Asp Gln Gly Arg Ile Asp Lys Gly Ala
945                 950                 955                 960

Ile Ala Thr Thr Asn Asn Gln Val Thr Ile Gln Ala Glu Ala Asn Thr
                965                 970                 975

Pro Tyr Val Ile Ala Glu Pro Asp Ser Ile Glu Pro Met Thr Phe Gly
            980                 985                 990

Thr Gly Thr Pro Phe Lys Asp Pro Gly Phe Asn Glu Ala Asn Thr Leu
        995                 1000                1005

Lys Asn Asn Trp Lys Val Phe Arg Gly Asp Gly Glu Val Lys Lys
        1010                1015                1020

Asp Ala Asn Gly Asp Tyr Val Phe Ser Ser Glu Lys Glu Arg Thr
        1025                1030                1035

Glu Ile Lys Gln Asp Ile Asn Leu Pro Lys Pro Gly Lys Tyr Ser
        1040                1045                1050

Leu Tyr Leu Asn Thr Glu Thr His Asp Arg Lys Ala Thr Val Thr
        1055                1060                1065

Val Lys Ile Gly Gly Lys Lys Tyr Thr Arg Thr Val Asn Asn Ser
        1070                1075                1080

Val Ala Gln Asn Tyr Ile Gln Ala Asp Ile Asn His Thr Ser Arg
        1085                1090                1095

Lys Asn Pro Gln Tyr Met Gln Asn Met Arg Ile Asp Phe Glu Ile
        1100                1105                1110

Pro Asp Asn Ala Lys Lys Gly Ser Val Thr Leu Ala Val Asp Lys
        1115                1120                1125

Gly Asn Ser Val Thr Lys Phe Asp Asp Leu Arg Ile Val Glu Arg
        1130                1135                1140

Gln Thr Asp Ile Met Asn Pro Asp Lys Gln Thr Val Ile Lys Gln
        1145                1150                1155

Asp Phe Glu Asp Thr Gln Ala Val Gly Leu Tyr Pro Phe Val Lys
        1160                1165                1170

Gly Ser Ala Gly Gly Val Glu Asp Pro Arg Ile His Leu Ser Glu
        1175                1180                1185

Arg Asn Glu Pro Tyr Thr Gln Tyr Gly Trp Asn Gly Asn Leu Val
        1190                1195                1200

Ser Asp Val Leu Glu Gly Asn Trp Ser Leu Lys Ala His Lys Gln
        1205                1210                1215

Gly Ala Gly Leu Met Leu Gln Thr Ile Pro Gln Asn Ile Lys Phe
        1220                1225                1230

Glu Pro Asn Lys Lys Tyr Thr Val Gln Phe Asp Tyr Gln Thr Asp
        1235                1240                1245

Gly Glu Asn Val Phe Thr Ala Gly Thr Ile Asn Gly Glu Leu Lys
        1250                1255                1260

Asn Asn Asn Asp Phe Lys Pro Val Gly Glu Leu Thr Ser Thr Ala
        1265                1270                1275

Ala Asp Gly Gln Thr Lys His Tyr Glu Ala Glu Ile Ile Gly Asp
        1280                1285                1290

Ala Ser Gly Asn Thr Thr Phe Gly Ile Phe Thr Thr Gly Ala Asp
```

```
                1295                1300                1305
Lys Asp Phe Ile Met Asp Asn Phe Thr Val Thr Val Glu Ser Lys
    1310                1315                1320

Lys

<210> SEQ ID NO 3
<211> LENGTH: 1321
<212> TYPE: PRT
<213> ORGANISM: Propionibacterium acnes

<400> SEQUENCE: 3

Met Ser Arg Thr Pro Arg Gly Arg Ser Ile Gly Ala Leu Ala Val Ser
1               5                   10                  15

Ala Gly Thr Met Leu Ala Leu Ile Ala Pro Thr Ala Pro Ala His Ala
            20                  25                  30

Glu Thr Arg Tyr Arg Gln Ile Asn Gln Ala Ala Ile Thr Ala Val Ala
        35                  40                  45

Ala Asp Ser Ala Thr Ala Thr Asp Pro Ile Ser Asn Thr Leu Asp Gly
    50                  55                  60

Asn Pro Asp Thr Ile Trp His Thr Thr Trp Gln Asn Gly Lys Asp Pro
65                  70                  75                  80

Leu Pro His Trp Ile Val Phe Lys Leu Gly Asp Glu Ala Val Asn Leu
                85                  90                  95

Gly Lys Val Glu Ile Thr Pro Arg Ser Ser Asn Gly Ser Gly Arg
            100                 105                 110

Met His Asp Tyr Glu Leu Tyr Thr Ala Asn Thr Lys Thr Cys Asn Asn
        115                 120                 125

Ala Ala Phe Ser Ser Ala Lys Pro Val Ala Thr Gly Ser Tyr Gly Ala
    130                 135                 140

Ser Asp Thr Ser Ile Arg Lys Ile Thr Phe Ala Ala Thr Lys Ala Thr
145                 150                 155                 160

Cys Val Lys Val Lys Val Asn Ser Ser Trp Gly Gly Asp Gly Ser Asp
                165                 170                 175

Glu Glu Val Ser Ser Met Ala Glu Phe Asn Ala Phe Thr Val Asp Gly
            180                 185                 190

Ser Asp Pro Ser Pro Asp Pro Thr Pro Ser Glu Pro Pro Thr Pro Glu
        195                 200                 205

Val Pro Lys Asp Ala Ile Ser Leu Ser Asp Gly Thr Val Thr Val Arg
    210                 215                 220

Ala Arg Arg Asp Phe Pro Gln Val Ile Asp Tyr Thr Val Gly His Ala
225                 230                 235                 240

His Met Ala Gly Arg Ile Gly Ser Pro Leu Thr Lys Val Arg Ile Asn
                245                 250                 255

Gly Ala Asp His Val Ala Thr Val Ser Ala Pro Thr Thr Thr Gly Ser
            260                 265                 270

Ser Ala Ser Trp Lys Leu Thr Phe Arg Asp Leu Pro Gly Val Glu Leu
        275                 280                 285

Thr Ala Asp Ile Lys Val Ser Asp Gly Val Met Thr Trp Ser Ile Pro
    290                 295                 300

His Ile Val Asp Thr Pro Asp His Arg Val Asn Thr Val Ser Val Pro
305                 310                 315                 320

Gly Leu Thr Leu Ala Ser Val Thr Ser Thr Asp Pro Lys Ala Gln Leu
                325                 330                 335

Ser Ser Ala Asn Ile Val Val Asp Arg Asn Lys Thr Gly Asp Leu Phe
```

-continued

```
                340                 345                 350
Gln Pro Leu Ala Thr Ala Asp Val Ser Gln Asp Thr Ser Trp Val Ala
            355                 360                 365
Met Ala Asn Asp Ser Thr Leu Ala Ala Gly Phe Glu Asp Asn Ala Thr
        370                 375                 380
Gln Asp Gly Leu Val Gly Ser Ala Ala Thr Val Ala Arg Phe Val His
385                 390                 395                 400
Ser Ile Ser Gln Val Gly Gly Thr Lys Val Gly Ala Ile Glu Pro Ala
                405                 410                 415
Thr Trp Val His Arg Gly Lys Gly Ser Ala Thr Pro Phe Pro Thr Asp
            420                 425                 430
Ser Leu Gly Asn Lys Ala Val Cys Gln Leu Pro Gly Gly Ala Thr Val
        435                 440                 445
Lys Asp Gly Ile Gly Pro Asp Pro Asp Thr Pro Tyr Val Arg Val Lys
450                 455                 460
Ile Val Ala Asp Ala Asn Ala Asp Gly Lys Val Asp Trp Gln Asp Ala
465                 470                 475                 480
Ala Val Ala Thr Arg Asp Val Thr Met Lys Pro Thr Gly Ser Gly Asp
                485                 490                 495
Val Ala Asn Lys Val Ile Thr His Ile Pro Phe Asn Ile Val Ser Gln
            500                 505                 510
Ala Thr His Pro Phe Leu Arg Thr Leu Asp Asp Val Lys Arg Ile Ser
        515                 520                 525
Leu Ala Thr Asp Gly Leu Gly Gln Gln Ala Leu Leu Lys Gly Tyr Gln
        530                 535                 540
Ala Glu Gly His Asp Ser Ala His Pro Asp Tyr Gly Gly Asn Val Ser
545                 550                 555                 560
His Arg Ala Gly Gly Met Lys Asp Leu Glu Lys Leu Thr Glu Ser Gly
                565                 570                 575
Arg Gln Trp Asn Thr Asp Phe Gly Ile His Val Asn Leu Val Glu Ser
            580                 585                 590
Tyr Pro Glu Ala Asn His Phe Gly Asp Asn Ile Leu Val Lys Pro Tyr
        595                 600                 605
Gln Lys Ala Trp Asp Trp Met Glu Gln Ser Tyr Arg Met Asp Tyr Ala
    610                 615                 620
Lys Asp Leu Gly Ser Gly Gln Leu Phe Ala Arg Leu Asn Gln Leu Arg
625                 630                 635                 640
Lys Glu Leu Gly Ala Lys Ser Asn Leu Asp Trp Leu Tyr Phe Asp Thr
                645                 650                 655
Asn Tyr Pro Ala Gly Trp Gln Asn Asp Arg Ile Ala Asn Ala Leu Asn
            660                 665                 670
Ala Glu Gly Trp Arg Ile Gly Ser Glu Trp Ser Ser Thr Tyr Pro Arg
        675                 680                 685
Tyr Asn Gln Trp Ser His Trp Ala Asn Asp Glu Asn Tyr Gly Thr Gly
        690                 695                 700
Asn Lys Gly Tyr Ser Ser Arg Ile Ile Arg Phe Ile Asp Asn Ser Arg
705                 710                 715                 720
Arg Asp Thr Trp Asn Pro Asp Pro Ile Leu Gly Asn Ser Asn Val Val
                725                 730                 735
Glu Tyr Glu Gly Trp Thr Ser His Asn Asp Tyr Asn Ala Phe Ile Ala
            740                 745                 750
Asn Val Trp Gln Arg Asn Leu Pro Thr Lys Phe Leu Gln Arg Ser Asp
        755                 760                 765
```

```
Ile Met Ser Trp Gln Asp Gly Arg Ile Ala Phe Ala Asn Gly Ala Val
    770                 775                 780

Ala Thr Ser Ser Lys Lys Ser Ile Ser Gly His Glu Ile Pro Thr Ala
785                 790                 795                 800

Arg Thr Ile Thr Phe Asp Gly Ala Thr Val Phe Lys Glu Gly Gly Ser
            805                 810                 815

Tyr Leu Leu Pro Trp Ser Asn Gly Gly Ser Asp Arg Leu Tyr Tyr Trp
                820                 825                 830

Asn Pro Gly Asn Gly Ser Ala Thr Trp Lys Leu Thr Asn Ser Trp Ala
        835                 840                 845

Ala Gln Lys Ser Val Ser Leu Phe Met Leu Thr Asp Thr Gly Arg Val
850                 855                 860

Lys Val Ala Glu Ile Pro Val Thr Asn Arg Ser Ile Arg Ile Pro Ala
865                 870                 875                 880

Thr Lys Ala Lys Thr Ala Tyr Val Leu Tyr Pro Thr Ser Lys Val Pro
            885                 890                 895

Ala Ala Lys Thr Pro Asn Trp Gly Glu Gly Ser His Phe Ala Asn Pro
                900                 905                 910

Gly Phe Tyr Ser Gly Asp Thr Ala Gly Trp Asn Ala Arg Gly Asn Val
        915                 920                 925

Ser Val Lys His Asn Asp Arg Gly Asn Phe His Leu Glu Phe Gly Lys
930                 935                 940

Ala Gln Ser Gln Ile Ser Gln Val Leu Asn Leu Pro Ala Gly Asp His
945                 950                 955                 960

Ser Leu Trp Ala Trp Val Gln Ile Asp Pro Thr Lys Thr Arg Pro Val
            965                 970                 975

Gly Leu Ala Val Asp Gly Thr Gly Val Thr Pro Ile Asp His Gln Lys
                980                 985                 990

Gly Cys Gly Gly His Ala Glu Ser Val Ile Thr Ser Thr Thr Ala Ile
        995                 1000                1005

Asn Ala Thr Ala Ser Asp Glu Tyr Phe Gly Thr Tyr His Gln Arg
    1010                1015                1020

Leu Arg Val Ala Phe His Ser Asp Gly Arg Pro Val Thr Val Thr
    1025                1030                1035

Leu Lys Ala Leu Ala Gly Asn Ala Ile Val Ser Ala Asp Asp Phe
    1040                1045                1050

Arg Val Val Asp Ala Ala Val Pro Ser Asp Pro His Val Thr Pro
    1055                1060                1065

Ala Thr Val Leu Phe Gln Asn Phe Glu Asp Val Asp Thr Gly Tyr
    1070                1075                1080

Trp Pro Phe Val Thr Gly Ser Ala Gly Met Glu Gly Asp Ala Arg
    1085                1090                1095

Thr Gln Leu Ser Arg Arg His Glu Pro Tyr Thr Gln Lys Gly Trp
    1100                1105                1110

Asn Gly Arg Ala Met Asp Ser Val Leu Ser Gly Asp Trp Ser Leu
    1115                1120                1125

Lys Met His Glu Glu Arg Asn Gly Ile Val Leu Arg Thr Thr Thr
    1130                1135                1140

Ala Ser Ala Pro Leu Thr Gly Gly Gly Thr Arg Tyr Arg Ile Ser
    1145                1150                1155

Phe Asp Tyr Gln Ala Asp Lys Pro Gly Tyr Ser Phe Val Thr Gly
    1160                1165                1170
```

```
His Asp Lys Val Ser Gly Lys Ser Val Lys Glu Val Ile Thr Glu
    1175                1180                1185

Ser His Ala Met Gly Val Ala Thr Ser Thr Thr His Phe Ser Thr
    1190                1195                1200

Asp Ile Val Val Lys Asp Gln Pro Ala Trp Ile Gly Phe Thr His
    1205                1210                1215

Gln Gly Glu Gly Asp Met Ser Ile Asp Asn Leu Arg Ile Glu Lys
    1220                1225                1230

Leu Asp Pro Arg Pro Ile Ser Val Thr Ser Thr Gln Ala Ala Val
    1235                1240                1245

Phe Pro Asp Ala Cys Lys Pro Thr Pro Glu Pro Ile Gln Pro Ala
    1250                1255                1260

Gln Pro Ser Ala Ser Ala Pro Thr Thr Ser Gly Ser Pro Gln Ala
    1265                1270                1275

Pro Gly Thr Gly Asn Arg Pro Asn Arg Tyr Ala Leu Pro Arg Thr
    1280                1285                1290

Gly Ala Asp Gly Ala Gly Leu Gly Phe Ser Ser Glu Ala Ala
    1295                1300                1305

Ser Ala Thr Ala Ala Val Gly Val Ser Arg Gln Gly Arg
    1310                1315                1320

<210> SEQ ID NO 4
<211> LENGTH: 1465
<212> TYPE: PRT
<213> ORGANISM: Arthrobacter aurescens
<220> FEATURE:
<221> NAME/KEY: MISC_FEATURE
<222> LOCATION: (1156)..(1465)
<223> OTHER INFORMATION: N-terminal signal sequence and C-terminal
      duplicate chitin-binding domains, which are deleted in EngAA*

<400> SEQUENCE: 4

Met Pro Arg Leu Ser Ser Pro Gly Arg Leu Ala Ser Leu Ser Leu Ala
1               5                   10                  15

Cys Val Val Ala Ser Ser Ser Leu Gly Leu Leu Ala Ile Pro Pro Ala
                20                  25                  30

Ala Ala Ala Pro Ser Thr Gln Pro Ala Asp Ile Val Ser Ala Ala Asp
            35                  40                  45

Thr Ala Thr Ile Thr Ser Gly Asp Leu Arg Val Asp Val Gly Thr Thr
    50                  55                  60

Phe Pro Gln Val Leu Gly Tyr Thr Asp Ala Ala Ser Lys Ala Arg Leu
65                  70                  75                  80

Asp Gly Thr Thr Thr Arg Leu Ser Thr Ile Thr Leu Asn Gly Thr Glu
                85                  90                  95

Tyr Thr Val Ser Gly Thr Ser Ala Ala Ser Gly Lys Asp Ala Arg Asp
                100                 105                 110

Tyr Val Leu Thr Leu Pro Asp Phe Gly Asn Thr Val Ile Lys Ala Arg
            115                 120                 125

Leu Ser Val Lys Lys Asn Val Val Ser Phe Asn Ile Thr Glu Ile Lys
    130                 135                 140

Asp Ser Ala Glu His Gln Val Arg Thr Leu Gln Leu Pro Arg Leu Asn
145                 150                 155                 160

Leu Val Thr Val Gly Ser Thr Gln Pro Gly Ser Gln Val Ser Thr Ala
                165                 170                 175

Asn Leu Ser Val Asp Arg Ser Val Thr Gly Asp Glu Phe Thr Pro Ile
            180                 185                 190
```

-continued

```
Thr Ala Ser Thr Pro Leu Asp Ala Ala Lys Ser Ser Ala Tyr Ala
            195                 200                 205
Leu Ala Asn Thr Ala Thr Leu Gly Ala Ala Val Glu Ser Asn Ala Leu
210                 215                 220
Tyr Asp Thr Ser Ser Gly Pro Gly Ala Lys Asp Arg Gly Arg Phe Trp
225                 230                 235                 240
Arg Gln Ala Val Ser Asp Gly Ala Gly Gly Val Asn Met Gly Leu Ala
                245                 250                 255
Ser Gly Gln Trp Leu Tyr Arg Ala Glu Gly Ser Thr Thr Glu Glu
            260                 265                 270
Leu Pro Trp Thr Arg Val Ala Ile Thr Ser Asp Ala Asn Asn Asp Gly
            275                 280                 285
Gly Val Asp Trp Gln Asp Ala Ala Ile Ala Met Arg Ser Ile Gln Val
        290                 295                 300
Ser Pro Asn Lys Gly Glu Gln Thr Pro Asp Asn Val Ile Thr His Ile
305                 310                 315                 320
Pro Phe Asn Phe Ala Ser Gln Ala Thr His Pro Phe Leu Arg Thr Leu
                325                 330                 335
Asp Asp Val Lys Arg Ile Ser Leu Ala Thr Asp Gly Leu Gly Gln Val
            340                 345                 350
Ala Met Leu Lys Gly Tyr Thr Ser Glu Gly His Asp Ser Ala Asn Thr
        355                 360                 365
Asp Tyr Gly Asn Asn Phe Asn Thr Arg Ala Gly Gly Leu Glu Asp Leu
    370                 375                 380
Asn Thr Leu Val Lys Glu Gly Lys Glu Trp Asn Ala Ser Phe Gly Val
385                 390                 395                 400
His Ile Asn Ala Thr Glu Ile Tyr Pro Glu Ala Lys Ser Phe Ser Glu
                405                 410                 415
Asp Leu Leu Arg Ala Asp Lys Gly Leu Gly Trp Asn Trp Leu Asp Gln
            420                 425                 430
Ser Tyr Tyr Met Asn Gln Arg Glu Asp Ile Asn Ser Gly Lys Leu Ala
        435                 440                 445
Gln Arg Ile Lys Glu Leu Arg Glu Ser Thr Asn Lys Asn Leu Asp Phe
    450                 455                 460
Val Tyr Val Asp Val Tyr Tyr Glu Phe Gly Trp Leu Ala Glu Arg Leu
465                 470                 475                 480
Gln Gln Glu Leu Val Lys Asn Gly Phe Arg Val Gly Ser Glu Trp Ala
                485                 490                 495
Asp His Leu Ser Arg Asn Asn Thr Trp Ser His Trp Ala Asn Asp Glu
            500                 505                 510
Lys Tyr Gly Gly Ser Thr Asn Lys Gly Ile Asn Ser Gln Ile Leu Arg
        515                 520                 525
Phe Ile Asn Asn Thr Gln Ser Asp Val Trp Asn Pro Asp Pro Lys Leu
    530                 535                 540
Gly Val Ser His Ile Val Glu Phe Glu Gly Trp Thr Gly Gln Asn Asp
545                 550                 555                 560
Phe Asn Ala Phe Ser Glu Asn Val Trp Thr Ala Asn Val Pro Ala Lys
                565                 570                 575
Phe Leu Gln His His Pro Ile Thr Lys Trp Thr Ala Glu Arg Ile Glu
            580                 585                 590
Leu Ala Asp Gly Val Ala Val Thr Gly Asn Thr Ala Glu Gly Arg Asn
        595                 600                 605
Ile Thr Val Gly Gly Thr Ser Val Leu Gln Gly Gly Thr Tyr Leu Leu
```

```
                        610             615                 620
Pro Trp Ser Ser Lys Glu Asn Gly Lys Val Asp Lys Leu Tyr His Tyr
625                     630                 635                 640

Asn Pro Thr Gly Gly Ala Ser Thr Trp Thr Leu Thr Gln Glu Phe Ala
                    645                 650                 655

Lys Ser Ser Ser Leu Glu Gln Phe Lys Leu Thr Asp Asn Gly Arg Val
                660                 665                 670

Lys Val Ala Asp Val Pro Val Val Asn Gly Gln Val Thr Val Thr Ala
            675                 680                 685

Asp Ala Lys Gln Pro Tyr Ile Leu Ala Pro Lys Asn Asn Lys Ala Glu
        690                 695                 700

Leu Pro Lys Lys Ala Asp Phe Gly Glu Gly Thr Ala Phe Asn Asp Pro
705                 710                 715                 720

Gly Phe Asn Gly Thr Asp Leu Ser Pro Trp Asn Pro Ala Gly Pro Val
                725                 730                 735

Thr Gln Val Arg Asp Asp Lys Gly Arg Arg Phe Ala Glu Met Gly Ala
            740                 745                 750

Thr Pro Ser Ser Ile Ser Gln Asp Val Gln Leu Asp Ala Gly Thr Gln
        755                 760                 765

Ser Val Ser Ala Trp Ile Glu Ile Gln Pro Gly Lys Thr Arg Pro Thr
    770                 775                 780

Thr Leu Ser Val Asp Ile Asp Gly Lys Thr Glu Ser Val Thr Ile Asp
785                 790                 795                 800

Ser Ser Asn Ala Glu Asn Tyr Val Ala Gly Asp Glu Lys His Gly Thr
                805                 810                 815

Ala Phe Gln Arg Ile Arg Val Leu Val Asp Val Pro Arg Asn Asn Thr
            820                 825                 830

Lys Ala Thr Val Thr Val Gln Ala Ala Asp Gly Asp Ala Thr Val Arg
        835                 840                 845

Val Asp Asp Phe Arg Ala Val Lys Thr Thr Arg Val Pro Thr Thr Gly
    850                 855                 860

Val Leu Ser Glu Asp Phe Glu Asn Val Asp Gln Gly Trp Gly Pro Phe
865                 870                 875                 880

Val Lys Gly Asp Ala Gly Gly Ser Thr Asp Pro Arg Thr His Ile Thr
                885                 890                 895

Glu Arg His Glu Pro Phe Thr Gln Lys Gly Trp Asp Ala Asn Val Ile
            900                 905                 910

Asp Glu Val Leu Asp Gly Thr Trp Ser Leu Ile Ala His Asp Glu Asn
        915                 920                 925

Arg Ala Pro Asn Gly Gly Pro Gly Met Val Tyr Arg Thr Thr Glu Ala
    930                 935                 940

Ser Val Pro Phe Gln Ala Gly His Lys Tyr Lys Val Ser Phe Asp Tyr
945                 950                 955                 960

Gln Asn Ser Lys Ala Gly Gln Tyr Ala Trp Val Ser Gly Tyr Asp Ser
                965                 970                 975

Gln Ala Gly Pro Ala Val Thr Gly Ser Gln Ala Ile Glu Ala Lys Thr
            980                 985                 990

Ser Thr Thr Arg Phe Glu Gln Ile Leu Asp Thr Gly Phe Cys Gly Asp
        995                 1000                1005

Tyr Phe Val Gly Leu Gln Arg Thr Gly Ser Ser Asn Gly Ser Asp
        1010                1015                1020

Phe Thr Leu Asp Asn Phe Leu Val Glu Asp Leu Gly Ala Ser Glu
        1025                1030                1035
```

```
Ala Val Pro Ala Cys Ala Gln Leu Ser Ala Glu Leu Gln Gly Asp
    1040            1045                1050
Val Val Gln Gln Gly Lys Ala Gln Asp Phe Val Thr Thr Phe Val
    1055            1060                1065
Ser Asp Glu Pro Ala Ala Ile Ser Gly Leu Ala Val Ala Leu Glu
    1070            1075                1080
Leu Pro Glu Gly Trp Thr Ala Thr Pro Ser Thr Pro Ala Thr Ala
    1085            1090                1095
Pro Thr Leu Pro Ala Gly Gly Thr Leu Thr Thr Trp Lys Ile
    1100            1105                1110
Thr Ala Pro Ala Ser Ala Asp Gly Asp Tyr Pro Ile Thr Ala Lys
    1115            1120                1125
Ala Ser Tyr Thr Val Ser Ser Gly Ile Asp Pro Ala Gly Ser
    1130            1135                1140
Arg Thr Ile Ser Thr Thr Thr Val Arg Thr Leu Pro Lys Pro
    1145            1150                1155
Pro Gln Ala Thr Val Phe Ala Ser Asp His Pro Trp Val Ser Ala
    1160            1165                1170
Thr Asn Gly Trp Gly Pro Val Glu Lys Asp Gln Ser Asn Gly Gly
    1175            1180                1185
Thr Gly Ala Gly Asp Gly Thr Pro Leu Thr Leu Asn Gly Thr Val
    1190            1195                1200
Tyr Ala Lys Gly Leu Gly Ala His Ala Asn Gly Thr Val Arg Tyr
    1205            1210                1215
Tyr Leu Gly Gly Tyr Cys Thr Ala Phe Thr Ala Thr Val Gly Ile
    1220            1225                1230
Asp Asp Ala Gln Pro Thr Arg Gly Ser Val Lys Phe Ser Val Val
    1235            1240                1245
Ala Asp Gly Thr Thr Lys Val Thr Thr Pro Val Leu Gly Ala Thr
    1250            1255                1260
Ser Ala Pro Leu Pro Leu Thr Val Asp Val Thr Gly Ala Gln Tyr
    1265            1270                1275
Val Glu Leu Val Ala Asn Asp Ala Gly Asp Ser Asn Gly Asn Asp
    1280            1285                1290
His Ala Asp Trp Ala Asp Ala Lys Phe Thr Cys Ser Ser Thr Ser
    1295            1300                1305
Gln Glu Pro Pro Ala Pro Val Leu Ser Gly Thr Val Phe Ala Ser
    1310            1315                1320
Asp Leu Pro Trp Ile Gly Ser Thr Asn Gly Trp Gly Pro Ala Glu
    1325            1330                1335
Arg Asp Arg Ala Asn Gly Glu Gln Asn Ala Gly Asp Gly Pro Ala
    1340            1345                1350
Leu Arg Leu Asp Gly Val Val Tyr Ser Lys Gly Ile Gly Val His
    1355            1360                1365
Ala Asp Ser Lys Ile Ser Ile Ala Thr Glu Ala Lys Cys Thr Ala
    1370            1375                1380
Phe Thr Ala Val Ala Gly Val Asp Asp Ala Lys Leu Asn Lys Gly
    1385            1390                1395
Leu His Gly Ser Val Val Phe Ile Val Lys Gly Gly Arg Glu
    1400            1405                1410
Leu Leu Arg Thr Pro Val Leu Ser Ala Asp Ser Ala Ala Leu Pro
    1415            1420                1425
```

```
Leu Asn Val Asp Ile Thr Gly Val Gln Asn Val Glu Leu Ile Ala
    1430                1435                1440

Asp Lys Asn Gly Asp Asp Ala Gly Asp Asp Trp Gly Asp Trp Ala
    1445                1450                1455

Asp Ala Lys Phe Ser Cys Ala
    1460                1465

<210> SEQ ID NO 5
<211> LENGTH: 1966
<212> TYPE: PRT
<213> ORGANISM: Bifidobacterium longum

<400> SEQUENCE: 5

Met Lys Lys Lys Lys Thr Ile Ser Ala Ala Leu Ala Thr Ala Leu Ala
1               5                   10                  15

Leu Thr Cys Met Gly Ser Gly Gly Thr Ala Phe Ala Val Pro Leu
                20                  25                  30

Ser Asp Ala Asp Leu Gln Thr Leu Ala Ser Gln Ile Gln Gln Ile Asn
            35                  40                  45

Asp Thr Ser Asp Ser Ala Thr Ala Ser Glu Thr Pro Ser Ala Gln Ala
    50                  55                  60

Asp Ala Val Glu Gly Trp Thr Ile Asp Ser Asn Ile Ala Gln Gly Gly
65                  70                  75                  80

Glu Ile Leu Glu Met Ala Asn Gly Trp Leu His Leu Lys Ser Thr Ala
                85                  90                  95

Ser Asn Gly Asn Ala Ala Ala Asn Pro Ser Ser Ser Asn Asn Trp Pro
            100                 105                 110

Ala Val Ala Val Trp Gly Thr Asp Tyr Asp Phe Ser Lys Ala Gly Ser
        115                 120                 125

Phe His Ala Thr Ile Lys Ser Pro Gln Glu Gly Ser Ala Asn Arg Phe
    130                 135                 140

Gly Phe Tyr Leu Gly Tyr Asn Asp Pro Gly Ser Gly Leu Phe Ile Gly
145                 150                 155                 160

Tyr Asp Ser Gly Gly Trp Phe Trp Gln Thr Tyr Thr Gly Gly Gly Ser
                165                 170                 175

Gly Ser Trp Tyr Ser Gly Ala Arg Ile Ala Ala Pro Ser Ala Asn Glu
            180                 185                 190

Glu His Asp Ile Arg Val Ser Trp Thr Asp Ala Lys Val Ala Thr Leu
        195                 200                 205

Thr Val Asp Gly Gln Lys Ala Phe Asp Val Asp Tyr Ser Ala Met Thr
    210                 215                 220

Asn Leu Ser Asn Lys Leu Ala Ile Lys Ala Gly Ser Trp Lys Glu Leu
225                 230                 235                 240

Asn Glu Val Thr Asp Val Tyr Ile Lys Asp Phe Pro Glu Val Val Glu
                245                 250                 255

Ala Ala Lys His Ala Val Ser Gly Lys Val Val Asp Ala Gly Gly Ala
            260                 265                 270

Ala Ile Glu Gly Ala Thr Val Arg Leu Asp Lys Thr Lys Val Lys Thr
        275                 280                 285

Gly Ala Asp Gly Thr Phe Ser Phe Ala Asp Ile Glu Glu Gly Glu His
    290                 295                 300

Thr Leu Ser Ile Ala Lys Glu Gly Tyr Glu Asp Val Ser Gln Gln Val
305                 310                 315                 320

Thr Val Ser Gly Ala Asp Leu Ala Ile Asp Pro Ile Thr Leu Asn Lys
                325                 330                 335
```

```
Thr Val Gln Val Ala Ser Glu Thr Leu Lys Thr Lys Met Glu Val
            340                 345                 350
Gln Ile Lys Lys Asn Phe Pro Ser Val Leu Gln Tyr Thr Met Thr Asp
            355                 360                 365
Gly Lys Val Met Tyr Gly Gln Ser Lys Asp Val Arg Thr Val Glu Ile
            370                 375                 380
Asn Gly Thr Asn Ile Glu Leu Gly Asp Asp Val Thr Phe Lys Lys
385                 390                 395                 400
Val Ser Asp Thr Glu Ala Thr Tyr Thr Leu Lys Val Lys Asp Glu Ala
                405                 410                 415
Lys Lys Ile Asp Ala Val Ile Thr Val Gln Ile Thr Val Lys Ala Asn
                420                 425                 430
Gln Leu His Leu Asn Val Thr Lys Ile Lys Asn Asn Leu Ser Glu Gly
            435                 440                 445
Ile Pro Glu Gly Asn Gly Val Glu Glu Asn Ala Ile Gln Thr Leu Ser
450                 455                 460
Phe Pro Asn Gln Ser Leu Val Ser Val Arg Ser Ser Gln Glu Asn Ala
465                 470                 475                 480
Gln Phe Thr Gly Ala Arg Met Ser Ser Asn Thr Gln Lys Pro Gly Asp
                485                 490                 495
Thr Asn Phe Ala Val Thr Glu Asp Thr Asn Val Thr Asp Ser Asp Tyr
                500                 505                 510
Thr Tyr Gly Phe Ile Ser Gly Ala Gly Leu Ser Ala Gly Leu Trp Ser
            515                 520                 525
Asn Ser Glu His Asp Gly Thr Tyr Val Ala Ala Pro Val Arg Gly Gly
            530                 535                 540
Ser Gln Asn Thr Arg Val Tyr Ala Thr Thr Gln Gln Thr Gly Asp Ala
545                 550                 555                 560
Thr Ser Leu Gly Leu Ala Ser Ala Pro Trp Tyr Tyr His Arg Thr Val
                565                 570                 575
Thr Asp Ser Lys Gly Lys Lys Tyr Thr Val Ala Glu Thr Ala Leu Pro
                580                 585                 590
Gln Met Ala Val Ala Ile Ala Gly Asp Glu Asn Glu Asp Gly Ala Val
            595                 600                 605
Asn Trp Gln Asp Gly Ala Ile Ala Tyr Arg Asp Ile Met Asn Asn Pro
610                 615                 620
Tyr Lys Ser Glu Glu Val Pro Glu Leu Val Ala Trp Arg Ile Ala Met
625                 630                 635                 640
Asn Phe Gly Ser Gln Ala Gln Asn Pro Phe Leu Thr Thr Leu Asp Asn
                645                 650                 655
Val Lys Lys Val Ala Leu Asn Thr Asp Gly Leu Gly Gln Ser Val Leu
                660                 665                 670
Leu Lys Gly Tyr Gly Asn Glu Gly His Asp Ser Gly His Pro Asp Tyr
            675                 680                 685
Gly Asp Ile Gly Gln Arg Leu Gly Gly Ala Asp Asp Met Asn Thr Met
            690                 695                 700
Met Glu Glu Gly Ser Lys Tyr Gly Ala Arg Phe Gly Val His Val Asn
705                 710                 715                 720
Ala Ser Glu Met Tyr Pro Glu Ala Lys Ala Phe Ser Glu Asp Met Val
                725                 730                 735
Arg Arg Asn Ser Ala Gly Gly Leu Ser Tyr Gly Trp Asn Trp Leu Asp
                740                 745                 750
```

-continued

Gln Gly Val Gly Ile Asp Gly Ile Tyr Asp Leu Ala Ser Gly Ser Arg
            755                 760                 765
Val Ser Arg Phe Ala Asp Leu Ser Lys Glu Val Gly Asp Asn Met Asp
        770                 775                 780
Phe Ile Tyr Leu Asp Val Trp Gly Asn Leu Thr Ser Ser Gly Ser Glu
785                 790                 795                 800
Asp Ser Trp Glu Thr Arg Lys Met Ser Lys Met Ile Asn Asp Asn Gly
            805                 810                 815
Trp Arg Met Thr Thr Glu Trp Gly Ser Gly Asn Glu Tyr Asp Ser Thr
        820                 825                 830
Phe Gln His Trp Ala Ala Asp Leu Thr Tyr Gly Gly Tyr Thr Ser Lys
        835                 840                 845
Gly Glu Asn Ser Glu Val Met Arg Phe Leu Arg Asn His Gln Lys Asp
        850                 855                 860
Ser Trp Val Gly Asp Tyr Pro Gln Tyr Gly Gly Ala Ala Asn Ala Pro
865                 870                 875                 880
Leu Leu Gly Gly Tyr Asn Met Lys Asp Phe Glu Gly Trp Gln Gly Arg
            885                 890                 895
Asn Asp Tyr Ala Ala Tyr Ile Lys Asn Leu Tyr Thr His Asp Val Ser
        900                 905                 910
Thr Lys Phe Ile Gln His Phe Lys Val Thr Arg Trp Val Asn Asn Pro
        915                 920                 925
Leu Leu Thr Ala Asp Asn Gly Asn Ala Ala Ala Val Ser Asp Pro Asn
        930                 935                 940
Thr Asn Asn Gly Asn Glu Gln Ile Thr Leu Lys Asp Ser Asn Gly Asn
945                 950                 955                 960
Val Val Val Val Ser Arg Gly Ser Asn Asp Thr Ser Ser Ala Ala Tyr
            965                 970                 975
Arg Gln Arg Thr Ile Thr Phe Asn Gly Val Lys Val Ala Ser Gly Val
        980                 985                 990
Val Ser Ala Gly Asp Gly Ser Ala  Thr Gly Asp Glu Ser  Tyr Leu Leu
            995                 1000                1005
Pro Trp  Met Trp Asp Ser Phe  Thr Gly Lys Leu Val  Lys Asp Ser
    1010                1015                1020
Glu Gln  Lys Leu Tyr His Trp  Asn Thr Lys Gly  Thr Thr Thr
    1025                1030                1035
Trp Thr  Leu Pro Asp Ser Trp  Lys Asn Leu Ser  Val Lys Val
    1040                1045                1050
Tyr Gln  Leu Thr Asp Gln Gly  Lys Thr Asn Glu Gln  Thr Val Ala
    1055                1060                1065
Val Ser  Gly Gly Lys Val Thr  Leu Thr Ala Asp Ala  Glu Thr Pro
    1070                1075                1080
Tyr Val  Val Tyr Lys Gly Glu  Ala Lys Gln Ile Gln  Val Asn Trp
    1085                1090                1095
Ser Glu  Gly Met His Val Val  Asp Ala Gly Phe Asn  Gly Gly Ser
    1100                1105                1110
Asn Thr  Leu Thr Asp Asn Trp  Thr Val Gly Gly Ser  Gly Lys Ala
    1115                1120                1125
Glu Val  Glu Gly Asp Asn Asn  Ala Met Leu Arg Leu  Thr Gly Lys
    1130                1135                1140
Val Asp  Val Ser Gln Arg Leu  Thr Asp Leu Lys Ala  Gly Gln Lys
    1145                1150                1155
Tyr Ala  Leu Tyr Val Gly Val  Asp Asn Arg Ser Thr  Gly Asp Ala

-continued

|  |  |  | 1160 |  |  |  | 1165 |  |  |  | 1170 |  |  |  |
|---|---|---|---|---|---|---|---|---|---|---|---|---|---|---|
| Ser | Val | Thr | Val | Thr | Ser | Gly | Gly | Lys | Val | Leu | Ala | Thr | Asn | Ser |
|  | 1175 |  |  |  | 1180 |  |  |  | 1185 |  |  |  |  |  |
| Thr | Gly | Lys | Ser | Ile | Ala | Lys | Asn | Tyr | Ile | Lys | Ala | Tyr | Gly | His |
|  | 1190 |  |  |  | 1195 |  |  |  | 1200 |  |  |  |  |  |
| Asn | Thr | Asn | Ser | Asn | Thr | Glu | Asn | Gly | Ser | Ser | Tyr | Phe | Gln | Asn |
|  | 1205 |  |  |  | 1210 |  |  |  | 1215 |  |  |  |  |  |
| Met | Tyr | Val | Phe | Phe | Thr | Ala | Pro | Glu | Asn | Gly | Asp | Ala | Thr | Val |
|  | 1220 |  |  |  | 1225 |  |  |  | 1230 |  |  |  |  |  |
| Thr | Leu | Ser | His | Lys | Ser | Thr | Asp | Gly | Ala | His | Thr | Tyr | Phe | Asp |
|  | 1235 |  |  |  | 1240 |  |  |  | 1245 |  |  |  |  |  |
| Asp | Val | Arg | Ile | Val | Glu | Asn | Gln | Tyr | Ser | Gly | Ile | Thr | Tyr | Glu |
|  | 1250 |  |  |  | 1255 |  |  |  | 1260 |  |  |  |  |  |
| Lys | Asp | Gly | Thr | Leu | Lys | Ser | Leu | Thr | Asn | Gly | Phe | Glu | Asn | Asn |
|  | 1265 |  |  |  | 1270 |  |  |  | 1275 |  |  |  |  |  |
| Ala | Gln | Gly | Ile | Trp | Pro | Phe | Val | Val | Ser | Gly | Ser | Glu | Gly | Val |
|  | 1280 |  |  |  | 1285 |  |  |  | 1290 |  |  |  |  |  |
| Glu | Asp | Asn | Arg | Ile | His | Leu | Ser | Glu | Leu | His | Ala | Pro | Phe | Thr |
|  | 1295 |  |  |  | 1300 |  |  |  | 1305 |  |  |  |  |  |
| Arg | Ala | Gly | Trp | Asp | Val | Lys | Lys | Met | Asp | Asp | Val | Leu | Asp | Gly |
|  | 1310 |  |  |  | 1315 |  |  |  | 1320 |  |  |  |  |  |
| Thr | Trp | Ser | Val | Lys | Val | Asn | Gly | Leu | Thr | Gln | Lys | Gly | Thr | Leu |
|  | 1325 |  |  |  | 1330 |  |  |  | 1335 |  |  |  |  |  |
| Val | Tyr | Gln | Thr | Ile | Pro | Gln | Asn | Val | Lys | Phe | Glu | Ala | Gly | Ala |
|  | 1340 |  |  |  | 1345 |  |  |  | 1350 |  |  |  |  |  |
| Lys | Tyr | Lys | Val | Ser | Phe | Asp | Tyr | Gln | Ser | Gly | Ser | Asp | Asp | Ile |
|  | 1355 |  |  |  | 1360 |  |  |  | 1365 |  |  |  |  |  |
| Tyr | Ala | Ile | Ala | Val | Gly | Gln | Gly | Glu | Tyr | Ser | Ala | Gly | Ser | Val |
|  | 1370 |  |  |  | 1375 |  |  |  | 1380 |  |  |  |  |  |
| Lys | Leu | Thr | Asn | Leu | Lys | Lys | Ala | Leu | Gly | Glu | Thr | Gly | Lys | Ala |
|  | 1385 |  |  |  | 1390 |  |  |  | 1395 |  |  |  |  |  |
| Glu | Phe | Glu | Leu | Thr | Gly | Gly | Val | Asn | Gly | Asp | Ser | Trp | Phe | Gly |
|  | 1400 |  |  |  | 1405 |  |  |  | 1410 |  |  |  |  |  |
| Ile | Tyr | Ser | Thr | Ala | Thr | Ala | Pro | Asp | Leu | Gln | Gly | Ser | Thr | Gly |
|  | 1415 |  |  |  | 1420 |  |  |  | 1425 |  |  |  |  |  |
| Asn | Ala | Gln | Asp | Phe | Gly | Gly | Tyr | Lys | Asp | Phe | Val | Leu | Asp | Asn |
|  | 1430 |  |  |  | 1435 |  |  |  | 1440 |  |  |  |  |  |
| Leu | Lys | Ile | Glu | Arg | Ile | Glu | Ser | Gln | Thr | Arg | Thr | Lys | Ala | Glu |
|  | 1445 |  |  |  | 1450 |  |  |  | 1455 |  |  |  |  |  |
| Ala | Gln | Asp | Lys | Val | Lys | Glu | Ile | Arg | Gly | Lys | Tyr | Asp | Ser | Lys |
|  | 1460 |  |  |  | 1465 |  |  |  | 1470 |  |  |  |  |  |
| Arg | Ala | Glu | Leu | Ser | Asp | Ala | Ala | Trp | Gln | Gln | Tyr | Gln | Asp | Thr |
|  | 1475 |  |  |  | 1480 |  |  |  | 1485 |  |  |  |  |  |
| Leu | Val | Lys | Ala | Arg | Val | Leu | Ile | Asn | Lys | Asn | Gly | Ala | Thr | Ala |
|  | 1490 |  |  |  | 1495 |  |  |  | 1500 |  |  |  |  |  |
| Glu | Asp | Phe | Thr | Lys | Ala | Tyr | Asp | Ile | Leu | Val | Ala | Leu | Asp | Glu |
|  | 1505 |  |  |  | 1510 |  |  |  | 1515 |  |  |  |  |  |
| Tyr | Met | Lys | Thr | Ala | Pro | Gly | Asn | Glu | Ser | Ser | Asp | Lys | Tyr | Asp |
|  | 1520 |  |  |  | 1525 |  |  |  | 1530 |  |  |  |  |  |
| Val | Ala | Ala | Asp | Gly | Ser | Asp | Glu | Leu | Gly | Gly | Tyr | Thr | Val | Ala |
|  | 1535 |  |  |  | 1540 |  |  |  | 1545 |  |  |  |  |  |
| Thr | Gly | Ser | Glu | Glu | Pro | Thr | Ala | Gly | Leu | Pro | Ser | Glu | Gly | Pro |
|  | 1550 |  |  |  | 1555 |  |  |  | 1560 |  |  |  |  |  |

```
Ala Asp Leu Ala Gln Asp Gly Asn Asp Ser Thr His Trp His Thr
1565             1570                 1575

Ser Trp Ser Glu Asn Ala Val Gly Asn Gly Thr Ala Trp Tyr Gln
    1580             1585                 1590

Phe Asn Leu Asn Glu Pro Thr Thr Ile Asn Gly Leu Arg Tyr Leu
1595             1600                 1605

Pro Arg Ser Gly Gly Met Asn Ala Asn Gly Lys Ile Lys Gly Tyr
    1610             1615                 1620

Lys Ile Thr Leu Thr Leu Ala Asp Gly Thr Thr Lys Asp Val Val
1625             1630                 1635

Thr Asp Ala Glu Phe Ser Thr Thr Thr Met Trp Gln Lys Ala Ser
    1640             1645                 1650

Phe Asp Ala Val Glu Asn Val Thr Ala Val Arg Leu Thr Val Leu
1655             1660                 1665

Ser Ser Ala Gly Gln Ser Asp Ser Gln Ala Asn Lys Phe Ala Ser
    1670             1675                 1680

Ala Ala Glu Leu Arg Leu Thr Thr Asp Arg Glu Val Glu Glu Glu
1685             1690                 1695

Thr Val Ala Pro Asp Lys Thr Asp Leu Asn Asp Thr Ile Ala Lys
    1700             1705                 1710

Ala Asn Gly Leu Lys Glu Ser Asp Tyr Thr Ala Glu Ser Trp Thr
1715             1720                 1725

Ala Leu Val Lys Ala Arg Glu Ala Ala Gln Ala Val Ala Asp Asn
    1730             1735                 1740

Asp Lys Ala Thr Ala Tyr Asp Val Ala Leu Ala Leu Thr Asn Leu
1745             1750                 1755

Glu Ser Ala Ile Ala Gly Leu Glu Lys Thr Gly Glu Glu Pro Gly
    1760             1765                 1770

Pro Gly Pro Val Glu Val Asn Lys Thr Asp Leu Gln Thr Ala Val
1775             1780                 1785

Asn Lys Ala Ser Lys Leu Glu Lys Ala Asp Tyr Thr Thr Asn Ser
    1790             1795                 1800

Trp Glu Ala Phe Ala Glu Ala Leu Lys Ala Ala Gln Gln Val Leu
1805             1810                 1815

Asp Asn Lys Asn Ala Thr Gln Gln Asp Val Asp Thr Ala Leu Ser
    1820             1825                 1830

Ala Leu Gln Asp Ala Ile Ser Lys Leu Glu Ala Ala Thr Glu Pro
1835             1840                 1845

Lys Pro Asn Pro Glu Pro Gly Val Val Asp Lys Ala Ala Leu Asn
    1850             1855                 1860

Ala Thr Ile Asn Lys Ala Ala Ile Asn Leu Gly Leu Tyr Thr
1865             1870                 1875

Asp Asp Ser Ala Asn Ala Leu Arg Ala Ala Leu Lys Lys Ala Arg
    1880             1885                 1890

Glu Val Ser Asp Asn Ser Asn Ala Thr Gln Lys Gln Val Asp Ala
1895             1900                 1905

Ala Arg Glu Ala Leu Glu Lys Ala Ile Ala Ala Leu Val Lys Arg
    1910             1915                 1920

Pro Ala Ala Lys Gly Asp Gly Asn Val Val Ser Asn Thr Gly Ser
1925             1930                 1935

Asp Val Ala Thr Ile Ala Leu Ala Gly Leu Leu Leu Ala Gly Ala
    1940             1945                 1950
```

Gly Ala Ala Ile Ala Tyr Arg Arg Asn Arg Glu Gln Leu
    1955                1960                1965

<210> SEQ ID NO 6
<211> LENGTH: 1686
<212> TYPE: PRT
<213> ORGANISM: Clostridium perfringens

<400> SEQUENCE: 6

Met Gly Arg Lys Cys Met Asn Lys Lys Ile Ala Ala Ile Ala Ala
1               5                   10                  15

Ala Val Ile Val Gly Gln Leu Pro Ile Ser Val Leu Ala Thr Pro Val
            20                  25                  30

Asn Glu Ala Gly Asp Glu Ile Asn Ser Glu Ser Ala Glu Ile Leu Thr
            35                  40                  45

Asn Ser Asp Glu Glu Ala Glu Ala Tyr Ile Gln Asn Tyr Asp Arg Pro
    50                  55                  60

Glu Gly Ile Thr Trp Thr Lys Leu Ala Gly Ser Gly Ser Val Glu Val
65                  70                  75                  80

Thr Asp Gly Phe Leu Ser Val Thr Asn Asn Gly Asp Tyr Arg Ile Met
                85                  90                  95

Glu Asp Gln Ser Pro Asn Ile Lys Asn Gly Glu Leu Glu Ser Lys Phe
            100                 105                 110

Thr Val Gly Gly Ser Gln Thr Gly Ile Ile Phe Arg Ala Thr Glu Ser
            115                 120                 125

Asn Tyr Gly Met Ile Asn Tyr Asn Ala Gly Thr Gly Trp Val Ile Glu
            130                 135                 140

Asn Lys Ser Asn Trp Glu Asp Ile Thr Gly Pro Arg Leu Asn Asn Gly
145                 150                 155                 160

Asp Val Val Thr Val Lys Ala Thr Phe Val Glu Lys His Leu Thr Val
                165                 170                 175

Asn Val Ser Val Asn Asp Gly Glu Phe Glu Thr Ile Tyr Asp Lys Glu
            180                 185                 190

Ser Asp Leu Ile Pro Leu Gln Ala Gly Lys Val Gly Tyr Arg Gly Trp
            195                 200                 205

Gly Asn Ala Lys Thr Thr Lys Phe Asp Tyr Ile Lys Tyr Ser Pro Met
210                 215                 220

Thr Ile Asp Lys Gly Pro Ile Val Ser Ile Asn Glu Val Asn Val Glu
225                 230                 235                 240

Thr Tyr Pro Arg Val Lys Pro Ile Leu Pro Ser Ser Val Thr Val Asn
                245                 250                 255

His Glu Asn Gly Met Ser Ser Ile Lys Asp Val Ser Trp Asn Tyr Ile
            260                 265                 270

Pro Lys Glu Ser Tyr Ser Lys Pro Gly Thr Phe Lys Val Glu Gly Thr
            275                 280                 285

Val Glu Gly Thr Asp Val Lys Ala Ile Ala Asn Val Thr Val Ser Ser
            290                 295                 300

Asp Leu Ala Tyr Tyr Glu Thr Asn Phe Glu Thr Glu Thr Arg Gly
305                 310                 315                 320

Asp Trp Gln Val Val Gln Gly Gly Ser Pro Ser Tyr Glu Glu Gly
                325                 330                 335

Lys Val Lys Ile Pro Met Asn Gly Val Ser Ile Ala Val Asp Met Asn
            340                 345                 350

Ser Pro Glu Val Lys Asn Phe Thr Tyr Glu Thr Asp Phe Ser Val Asp
            355                 360                 365

```
Asn Asn Gly Gly Arg Ile Gly Leu Leu Phe Arg Tyr Val Ser Glu Thr
    370                 375                 380

Glu Trp Gly Ala Val Cys Tyr Asp Asn Gly Ser Trp Val Trp Lys Thr
385                 390                 395                 400

Gly Asp Gly Lys Tyr Gly Asn Phe Pro Gly Thr Phe Thr Pro Glu Gln
                405                 410                 415

Gly Lys Thr Tyr Arg Ile Lys Leu Lys Val Glu Asp Thr Asn Ile Thr
                420                 425                 430

Met Trp Val Asp Gly Glu Lys Ile Gly Gln Val Ala Val Ser Asn Leu
                435                 440                 445

Pro Asp Val Arg Gly Lys Val Gly Leu Thr Gly Trp Phe Gly Asn Lys
450                 455                 460

Asn Val Thr Leu Asp Asn Leu Val Val Glu Glu Leu Gly Gly Ile Met
465                 470                 475                 480

Ala Pro Glu Val Gly Pro Leu Gln Gln Ser Ile Glu Ser Asp Ser
                485                 490                 495

Met Lys Val Val Leu Asp Asn Arg Phe Pro Thr Val Ile Arg Tyr Glu
                500                 505                 510

Trp Lys Gly Thr Glu Asp Val Leu Ser Gly Ala Ser Val Asp Asp Leu
                515                 520                 525

Glu Ala Gln Tyr Met Val Glu Ile Asn Gly Glu Lys Arg Ile Pro Lys
530                 535                 540

Val Thr Ser Glu Phe Ala Asn Asn Glu Gly Ile Tyr Thr Leu Asn Phe
545                 550                 555                 560

Glu Asp Ile Gly Met Thr Ile Thr Leu Lys Met Thr Val Asn Glu Asn
                565                 570                 575

Lys Leu Arg Met Glu Val Thr Asp Ile Gln Glu Gly Asp Val Lys Leu
                580                 585                 590

Gln Thr Leu Asn Phe Pro Asn His Ser Leu Ala Ser Val Ser Ser Leu
                595                 600                 605

Asn Asn Gly Lys Thr Ala Ser Val Leu Thr Thr Gly Asp Trp Asn Asn
                610                 615                 620

Ile Asn Glu Glu Phe Thr Asp Val Ala Lys Ala Lys Pro Gly Val Lys
625                 630                 635                 640

Gly Lys Thr Tyr Ala Phe Ile Asn Asp Asp Lys Phe Ala Val Thr Ile
                645                 650                 655

Asn Asn Asn Thr Ile Glu Gly Gly Asn Arg Val Val Leu Thr Thr Glu
                660                 665                 670

Lys Asp Thr Leu Pro Asp Asn Thr Asn Tyr Lys Lys Val Gly Ile Ser
                675                 680                 685

Asn Gly Thr Trp Thr Tyr Lys Glu Ile Leu Gln Asp Thr Thr Asp Gln
                690                 695                 700

Gly Ser Lys Leu Tyr Gln Gly Glu Lys Pro Trp Ser Glu Val Ile Ile
705                 710                 715                 720

Ala Arg Asp Glu Asn Glu Asp Gly Gln Val Asp Trp Gln Asp Gly Ala
                725                 730                 735

Ile Gln Tyr Arg Lys Asn Met Lys Ile Pro Val Gly Gly Glu Glu Ile
                740                 745                 750

Lys Asn Gln Met Ser Tyr Ile Asp Phe Asn Ile Gly Tyr Thr Gln Asn
                755                 760                 765

Pro Phe Leu Arg Ser Leu Asp Thr Ile Lys Lys Leu Ser Asn Tyr Thr
770                 775                 780
```

-continued

Asp Gly Phe Gly Gln Leu Val Leu His Lys Gly Tyr Gln Gly Glu Gly
785                 790                 795                 800

His Asp Asp Ser His Pro Asp Tyr Gly Gly His Ile Gly Met Arg Gln
            805                 810                 815

Gly Gly Lys Glu Asp Phe Asn Thr Leu Ile Glu Gln Gly Lys Glu Tyr
            820                 825                 830

Asn Ala Lys Ile Gly Val His Ile Asn Ala Thr Glu Tyr Thr Met Asp
            835                 840                 845

Ala Phe Glu Tyr Pro Thr Glu Leu Val Asn Glu Asn Ala Pro Gly Trp
    850                 855                 860

Gly Trp Leu Asp Gln Ala Tyr Tyr Val Asn Gln Arg Gly Asp Ile Thr
865                 870                 875                 880

Ser Gly Glu Leu Phe Arg Arg Leu Asp Met Leu Met Glu Asp Ala Pro
                885                 890                 895

Glu Leu Gly Trp Ile Tyr Val Asp Val Tyr Thr Gly Asn Gly Trp Asn
                900                 905                 910

Ala His Gln Leu Gly Lys Ile Asn Asp Tyr Gly Ile Met Ile Ala
            915                 920                 925

Thr Glu Met Asn Gly Pro Leu Glu Gln His Val Pro Trp Thr His Trp
            930                 935                 940

Gly Gly Asp Pro Ala Tyr Pro Asn Lys Gly Asn Ala Ser Lys Ile Met
945                 950                 955                 960

Arg Phe Met Lys Asn Asp Thr Gln Asp Ser Phe Leu Ala Asp Pro Leu
                965                 970                 975

Val Lys Gly Asn Lys His Leu Leu Ser Gly Gly Trp Gly Thr Arg His
            980                 985                 990

Asp Ile Glu Gly Ala Tyr Gly Thr Glu Val Phe Tyr Asn Gln Val Leu
            995                 1000                1005

Pro Thr Lys Tyr Leu Gln His Phe Gln Ile Thr Lys Met Ser Glu
    1010                1015                1020

Asn Glu Val Leu Phe Glu Asn Gly Val Lys Ala Val Arg Glu Asn
    1025                1030                1035

Ser Asn Ile Asn Tyr Tyr Arg Asn Asp Arg Leu Val Ala Thr Thr
    1040                1045                1050

Pro Glu Asn Ser Ile Gly Asn Thr Gly Ile Gly Asp Thr Gln Leu
    1055                1060                1065

Phe Leu Pro Trp Asn Pro Val Asp Glu Ala Asn Ser Glu Lys Ile
    1070                1075                1080

Tyr His Trp Asn Pro Leu Gly Thr Thr Ser Glu Trp Thr Leu Pro
    1085                1090                1095

Glu Gly Trp Thr Ser Asn Asp Lys Val Tyr Leu Tyr Glu Leu Ser
    1100                1105                1110

Asp Leu Gly Arg Thr Leu Val Lys Glu Val Pro Val Val Asp Gly
    1115                1120                1125

Lys Val Asn Leu Glu Val Lys Gln Asp Thr Pro Tyr Ile Val Thr
    1130                1135                1140

Lys Glu Lys Val Glu Glu Lys Arg Ile Glu Asp Trp Gly Tyr Gly
    1145                1150                1155

Ser Glu Ile Ala Asp Pro Gly Phe Asp Ser Gln Thr Phe Asp Lys
    1160                1165                1170

Trp Asn Lys Glu Ser Thr Ala Glu Asn Thr Asp His Ile Thr Ile
    1175                1180                1185

Glu Asn Glu Ser Val Gln Lys Arg Leu Gly Asn Asp Val Leu Lys

```
                       1190                1195                1200
Ile Ser Gly Asn Glu Gly Ala Asp Ala Lys Ile Ser Gln Ser Ile
    1205                1210                1215
Ser Gly Leu Glu Glu Gly Val Thr Tyr Ser Val Ser Ala Trp Val
    1220                1225                1230
Lys Asn Asp Asn Arg Glu Val Thr Leu Gly Val Asn Val Gly
    1235                1240                1245
Gly Lys Asp Phe Thr Asn Val Ile Thr Ser Gly Lys Val Arg
    1250                1255                1260
Gln Gly Glu Gly Val Lys Tyr Ile Asp Asp Thr Phe Val Arg Met
    1265                1270                1275
Glu Val Glu Phe Thr Val Pro Lys Gly Val Asn Ser Ala Asp Val
    1280                1285                1290
Tyr Leu Lys Ala Ser Glu Gly Asp Ala Asp Ser Val Val Leu Val
    1295                1300                1305
Asp Asp Phe Arg Ile Trp Asp His Pro Gly His Thr Asn Arg Asp
    1310                1315                1320
Gly Tyr Val Phe Tyr Glu Asp Phe Glu Asn Val Asp Glu Gly Ile
    1325                1330                1335
Ser Pro Phe Tyr Leu Ser Pro Gly Arg Gly His Ser Asn Arg Ser
    1340                1345                1350
His Leu Ala Glu Lys Asp Ile Ser Ile Asp Ala Asn Gln Arg Met
    1355                1360                1365
Asn Trp Val Leu Asp Gly Arg Phe Ser Leu Lys Ser Asn Gln Gln
    1370                1375                1380
Pro Lys Glu Ile Gly Glu Met Leu Thr Thr Asp Val Ser Ser Phe
    1385                1390                1395
Lys Leu Glu Pro Asn Lys Thr Tyr Glu Phe Gly Phe Leu Tyr Ser
    1400                1405                1410
Leu Glu Asn Ala Ala Pro Gly Tyr Ser Val Asn Ile Lys Asn Arg
    1415                1420                1425
Asp Gly Glu Lys Ile Val Asn Ile Pro Leu Glu Ala Thr Gly Ser
    1430                1435                1440
Asn Tyr Ala Gln Asp Ile Phe Thr Lys Thr Lys Ser Val Thr His
    1445                1450                1455
Glu Phe Thr Thr Gly Asp Phe Ala Gly Asp Tyr Tyr Ile Thr Leu
    1460                1465                1470
Glu Lys Gly Asp Gly Phe Lys Glu Val Ile Leu Asp Asn Ile Tyr
    1475                1480                1485
Val Lys Glu Ile Asp Lys Ser Ile Glu Ser Pro Glu Leu Ala His
    1490                1495                1500
Val Asn Leu Asn Thr Val Glu His Asp Leu Glu Val Gly Gln Ser
    1505                1510                1515
Val Pro Phe Ala Ile Asn Ala Leu Met Asn Asn Gly Ala Asn Val
    1520                1525                1530
Asn Leu Glu Glu Ala Glu Val Glu Tyr Lys Val Ser Lys Pro Glu
    1535                1540                1545
Val Leu Thr Ile Glu Asn Gly Met Met Thr Gly Ala Ser Glu Gly
    1550                1555                1560
Phe Thr Asp Val Gln Val Asn Ile Thr Val Asn Gly Asn Lys Val
    1565                1570                1575
Ser Ser Asn Thr Val Arg Val Lys Val Gly Asn Pro Glu Val Glu
    1580                1585                1590
```

```
Glu Glu Glu Val Ile Val Asn Pro Val Arg Asn Phe Lys Val Thr
    1595                1600                1605

Asp Lys Thr Lys Lys Asn Val Thr Val Ser Trp Glu Glu Pro Glu
    1610                1615                1620

Lys Thr Tyr Gly Leu Glu Gly Tyr Val Leu Tyr Lys Asp Gly Lys
    1625                1630                1635

Lys Val Lys Glu Ile Gly Ala Asp Lys Thr Glu Phe Thr Phe Lys
    1640                1645                1650

Gly Leu Asn Arg His Thr Ile Tyr Asn Phe Lys Ile Ala Ala Lys
    1655                1660                1665

Tyr Ser Asn Gly Glu Leu Ser Thr Lys Glu Ser Ile Thr Val Arg
    1670                1675                1680

Thr Ala Arg
    1685

<210> SEQ ID NO 7
<211> LENGTH: 1413
<212> TYPE: PRT
<213> ORGANISM: Janibacter sp.

<400> SEQUENCE: 7

Met Pro Ser Val Asp Thr Ala Ala Pro Val Val Ile Ala Ser Ala
1               5                   10                  15

Asp Leu Glu Val Gln Leu Ser Pro Thr Phe Pro Gln Ala Leu Ala Tyr
                20                  25                  30

Arg Ser Val Gly Ser Gly Ala Leu Leu Gly Gly Gln Val Asp Pro Ile
                35                  40                  45

Ala Ser Val Thr Ile Asn Gly Thr Pro Arg Ala Ala Val Ala Thr Val
    50                  55                  60

Thr Pro Gly Ala Ser Ser Ala Ala Tyr Ala Leu Thr Phe Ala Asp Leu
65                  70                  75                  80

Pro Gly Val Arg Ile Glu Leu Thr Val Ser Val Glu Gly Asn Val Leu
                85                  90                  95

Thr Trp Arg Val Thr Lys Val Thr Asp Ser Ser Ser Val Lys Val Gly
                100                 105                 110

Thr Leu Asp Ile Pro Gly Leu Asp Leu Val Ser Val Ser Ser Ala Gln
                115                 120                 125

Ala Gly Ala Thr Thr Ala Phe Thr Lys Ile Asp Thr Asn Ser Thr Arg
    130                 135                 140

Asn Ala Asp Val Ile Ala Pro Val Lys Ala Thr Asp Ala Val Gln Thr
145                 150                 155                 160

Ala Pro Val Gly Ala Ala Tyr Gly Ile Val Asn Thr Ala Gln Leu Ala
                165                 170                 175

Ala Ser Val Glu Thr Asn Gly Thr Tyr Asp Lys Pro Thr Ser Ala Thr
                180                 185                 190

Asn Ser Asp Asn Gly Arg Phe Trp His Gln Val Arg Ala Asn Ser Asp
                195                 200                 205

Gly Ser Lys Arg Val Gly Ile Ala Pro Gly Gln Trp Thr Val Arg Gly
    210                 215                 220

Asp Gly Ala Pro Ala Gln Ser Glu Leu Pro Trp Ala Lys Val Val Val
225                 230                 235                 240

Thr Gly Asp Ala Asn Ala Asp Ala Ala Val Asp Trp Gln Asp Gly Ala
                245                 250                 255

Ile Ala Phe Arg Ser Ile Ala Gln Val Ala Lys Gly Ala Asp Gln Val
```

-continued

```
                260                 265                 270
Pro Asn Arg Val Val Gln His Ile Pro Phe Asn Phe Ser Ser Leu Ala
            275                 280                 285
Thr His Pro Phe Leu Arg Thr Leu Asp Asp Val Lys Arg Ile Ser Gln
            290                 295                 300
Glu Thr Asp Gly Leu Gly Gln Phe Ala Leu Leu Lys Gly Tyr Ala Ser
305                 310                 315                 320
Glu Gly His Asp Ser Ala His Pro Asp Tyr Gly Asp Asn Phe Asn Thr
                325                 330                 335
Arg Ala Gly Gly Leu Asp Asp Met Asn Thr Leu Leu Glu Gln Gly Lys
                340                 345                 350
Lys Trp Gly Ala Asp Phe Gly Val His Val Asn Ala Thr Glu Ala Tyr
            355                 360                 365
Pro Glu Ala Lys Ala Phe Asn Glu Thr Leu Val Asp Lys Thr Lys Pro
            370                 375                 380
Gly Trp Asn Trp Leu Asn Gln Ser Tyr Tyr Ile Asn Gln Arg Thr Asp
385                 390                 395                 400
Leu Asn Ser Gly Asp Leu Leu Arg Arg Thr Gln Gln Leu Arg Asp Ala
                405                 410                 415
Thr Lys Gly Asn Leu Asp Thr Leu Tyr Trp Asp Val Tyr Tyr Thr Tyr
                420                 425                 430
Gly Trp Leu Pro Asp Gln Met Asp Ala Lys Leu Arg Glu Gln Gly Trp
            435                 440                 445
Ser Val Ala Ser Glu Trp Ala Tyr Ser His Glu Arg Asn Ser Leu Trp
            450                 455                 460
Ser His Trp Ala Thr Asp Arg Asn Tyr Gly Gly Ala Thr Asn Lys Gly
465                 470                 475                 480
Ile Asn Ser Thr Ile Ala Arg Phe Ile Arg Asn Gly Glu Lys Asp Val
                485                 490                 495
Trp Asn Pro Asp Pro Val Leu Gly Gly Ser Thr Ile Val Glu Ala Glu
                500                 505                 510
Gly Trp Thr Gly Gln His Asp Trp Asn Ala Leu Met Lys Asn Val Trp
            515                 520                 525
Ala Asn Gln Val Pro Thr Lys Phe Leu Gln His Phe Asp Ile Thr Lys
            530                 535                 540
Trp Gly Asp Ala Ala Gly Thr Thr Ser Ile Asp Phe Asp Gly Gly Val
545                 550                 555                 560
Arg Gly Thr Ser Lys Asp Gly Val Arg Gln Leu Phe Val Ala Asp Ala
                565                 570                 575
Lys Val Leu Asp Gly Asp Ala Tyr Leu Leu Pro Trp Gly Asp Glu Thr
                580                 585                 590
Pro Asn His Pro Thr Lys Ala Tyr His Tyr Asn Ala Asp Gly Gly Thr
            595                 600                 605
Thr Thr Trp Lys Leu Ala Pro Lys Leu Arg Ser Thr Lys Ser Phe Thr
            610                 615                 620
Val Tyr Glu Leu Ser Glu Thr Gly Arg Thr Lys Val Gly Thr Val Ala
625                 630                 635                 640
Asn Thr Lys Asn Ser Val Thr Leu Thr Ala Lys Ser Asn Thr Ala Tyr
                645                 650                 655
Val Leu Tyr Pro Asn Ser Val Pro Ala Gln Ala Asp Pro Gln Phe Gly
                660                 665                 670
Gln Gly Gly Ile Val Lys Asp Pro Gly Phe Asn Ala Ser Thr Leu Gly
            675                 680                 685
```

```
Ala Trp Ser Pro Gln Gly Thr Val Thr Gln Glu His Leu Ser Thr Gly
690                 695                 700

Gln Arg Val Ala Gln Ile Gly Ala Gly Ala Gly Ser Ile Ser Gln Gln
705                 710                 715                 720

Leu Thr Gly Leu Lys Ala Gly Ser Arg Tyr Ala Ala Ser Ala Trp Val
                725                 730                 735

Gln Val Ala Pro Gly Gly Val Arg Pro Thr Thr Val Ser Val Lys Gly
                740                 745                 750

Ser Gly Val Asp Val Ala Asn Ala Phe Asp Arg Ser Thr Val Thr Asn
            755                 760                 765

Ser Glu Ala Ser Asn Glu Leu His Gly Thr Ser Tyr Gln Arg Val Arg
770                 775                 780

Val Ile Phe Thr Ala Pro Ala Asp Gly Thr Val Thr Phe Ser Val Ala
785                 790                 795                 800

Ala Ala Ala Gly Ser Ala Pro Val Gly Ile Asp Asp Val Arg Val Val
                805                 810                 815

Ala Thr Thr Glu Ala Ala Pro Ala Gly Asp Val Ile Ala His Gln Asp
                820                 825                 830

Phe Glu Gly Val Asp Gln Gly Trp Met Pro Phe Val Ser Gly Pro Ala
            835                 840                 845

Gln Ser Gly Gly Asp Ala Arg Thr His Leu Ser Gln Arg Asn Ala Pro
850                 855                 860

Tyr Thr Gln Ala Gly Trp Asn Gly Lys Leu Val Asp Asp Ala Leu Asp
865                 870                 875                 880

Gly Thr Trp Ser Leu Lys Ala His Glu Glu Ala Asn Gly Leu Val Tyr
                885                 890                 895

Arg Thr Trp Ala Gly Thr Val Pro Phe Glu Gln Gly His Arg Tyr Lys
                900                 905                 910

Val Glu Phe Asp Tyr Gln Asn Ala Thr Ala Gly Ala Tyr Ser Phe Val
            915                 920                 925

Thr Gly Val Asp Gln Val Val Gly Gly Thr Ser Lys Thr Ala Glu Leu
            930                 935                 940

Ser Thr Thr Ala Phe Gly Gln Gln Arg Thr Thr Gln Ala Phe Ser Arg
945                 950                 955                 960

Glu Ile Thr Thr Gly Ser Cys Gly Thr Pro Phe Ile Gly Leu Arg Arg
                965                 970                 975

Asn Ala Val Gly Ser Ala Gln Ala Asp Phe Ile Leu Asp Asn Leu Lys
            980                 985                 990

Val Thr Asp Leu Gly Ala Thr Asp Glu Pro Gly Ala Cys Ser Arg Leu
            995                 1000                1005

Glu Val Thr Gly Pro Ala Ser Gly Leu Val Pro Gly Glu Ala Asn
    1010                1015                1020

Thr Phe Thr Thr Thr Phe Ser Ser Phe Glu Thr Ala Ala Thr
    1025                1030                1035

Asp Val Thr Val Ser Leu Lys Ala Pro Asp Gly Trp Thr Val Thr
    1040                1045                1050

Pro Thr Thr Thr Ala Thr Phe Ala Ser Val Ala Pro Gly Ala Ser
    1055                1060                1065

Val Lys Thr Thr Trp Arg Val Val Pro Ala Thr Thr Pro Ala
    1070                1075                1080

Gly Ser Tyr Ala Leu Thr Ser Ser Ala Ala Tyr Thr Val Asp Gly
    1085                1090                1095
```

-continued

```
Glu Ala Arg Ser Val Thr Ala Ser Gly Ser Phe Ala Thr Leu Pro
    1100                1105                1110

Ala Gly Lys Ile Pro Gln Ser Arg Leu Ser Ile Ala Gly Val Ser
    1115                1120                1125

Asp Ala Glu Pro Ala Ser Ala Gly Gly Gln Pro Ser Asn Ala Ile
    1130                1135                1140

Asp Gly Leu Thr Thr Thr Met Trp His Ser Ala Trp Ser Gln Val
    1145                1150                1155

Asp Pro Asp Ala Pro Phe Pro His Trp Ile Thr Val Asp Leu Gly
    1160                1165                1170

Asp Thr Tyr Asp Val Asn Gly Tyr Asp Tyr Gln Val Arg Ile Gly
    1175                1180                1185

Asn Gly Ser Ile Lys Gly Tyr Glu Ile Tyr Val Ser Ala Asp Asn
    1190                1195                1200

Val Thr Trp Gly Ala Pro Val Lys Thr Gly Ser Phe Ala Ser Thr
    1205                1210                1215

Thr Glu Val Gln His Leu Asp Phe Thr Ala Lys Pro Gly Arg Tyr
    1220                1225                1230

Val Lys Leu Val Gly Leu Ser Ser Ile Asn Gly Ala Val Phe Gly
    1235                1240                1245

Gly Ala Gly Glu Ile Asn Val Trp Gly Lys Arg Val Asn Glu Pro
    1250                1255                1260

Pro Val Ala Leu Ser Lys Ala Pro Met Ser Ile Gln Ser Val Asp
    1265                1270                1275

Ser Gln Glu Thr Glu Gly Glu Asp Gly Ala Ala Thr Asn Val Leu
    1280                1285                1290

Asp Asp Asn Pro Gly Thr Phe Trp His Thr Glu Trp Leu Asn Ala
    1295                1300                1305

Glu Thr Pro Tyr Pro His His Ile Ala Val Asp Leu Gly Ala Ser
    1310                1315                1320

His Thr Leu Ser Gly Ile Ser Val Gln Gly Arg Gln Asp Gly Asn
    1325                1330                1335

Val Asn Gly Pro Ile Lys Asp Tyr Glu Val Tyr Val Ser Ala Asp
    1340                1345                1350

Gly Thr Asn Trp Gly Thr Pro Val Ala Gln Gly Ser Phe Thr Ala
    1355                1360                1365

Thr Thr Ala Ala Gln Leu Val Asn Phe Ala Gln Pro Thr Thr Gly
    1370                1375                1380

Arg Phe Val Lys Val Val Ala Lys Asn Ser Ile Asn Gly Ala Ala
    1385                1390                1395

Phe Ala Ala Ile Ala Glu Leu Gln Phe Tyr Ala Pro Ala Thr Pro
    1400                1405                1410

<210> SEQ ID NO 8
<211> LENGTH: 1708
<212> TYPE: PRT
<213> ORGANISM: Ruminococcus torques

<400> SEQUENCE: 8

Met Val Val Asn Pro Asn Thr Phe Asp Phe Asn Lys Pro Gly Tyr Phe
1               5                   10                  15

Ser Phe Thr Leu Lys Ser Asn Asn Ala Asn Thr Gly Ile Ser Asp Ser
            20                  25                  30

Asp Arg Val Gly Val Tyr Leu Gly Tyr Asn Thr Asp Gln Asn Gly Met
        35                  40                  45
```

```
Tyr Ile Gly Tyr Asp Asn Gly Gly Trp Phe Trp Gln Lys Tyr Lys Gly
         50                  55                  60

Gly Asn Gly Asp Tyr Tyr Gln Gln Thr Arg Lys Pro Ala Pro Thr Lys
 65                  70                  75                  80

Asp Gln Glu Val Lys Val Arg Ile Asp Trp Thr Ala Asp His Lys Met
                 85                  90                  95

Thr Phe Thr Leu Asn Gly Glu Val Val Phe Asp Lys Glu Asp Phe Ser
                100                 105                 110

Gly Ile Ala Asp Ser Leu Gly Asn Lys Ile Ala Ile Lys Ala Gly Ser
            115                 120                 125

Trp Gly Gln Ile Gly Ser Asp Val Leu Leu Lys Asp Ile His Tyr Thr
            130                 135                 140

Gly Gln Glu Glu Ala Val Thr Tyr Thr Val Thr Gly Ser Val Thr Asp
145                 150                 155                 160

Glu Ser Gly Lys Ala Leu Glu Gly Ala Val Val Thr Thr Gly Asn Leu
                165                 170                 175

Thr Ala Glu Thr Asp Lys Asp Gly Lys Tyr Ser Leu Gln Leu Gly Ala
                180                 185                 190

Gly Lys His Glu Leu Thr Ile Thr Lys Ala Gly Tyr Gln Thr Ala Thr
            195                 200                 205

Thr Ser Val Thr Val Thr Glu Gly Asn Val Glu Ala Lys Ala Val Lys
210                 215                 220

Leu Glu Lys Thr Ala Glu Ile Glu Thr Glu Lys Leu Ser Thr Ala Asp
225                 230                 235                 240

Met Asp Val Tyr Val Ala Lys Asn Phe Pro Ser Val Val Lys Tyr Glu
                245                 250                 255

Met Lys Lys Gly Asp Leu Asn Gly Lys Thr Phe Tyr Gly Gln Thr Ser
                260                 265                 270

Ala Ile Asn Thr Val Arg Ile Asn Gly Thr Asp Val Lys Leu Ser Lys
            275                 280                 285

Gly Asp Val Lys Ala Thr Ile Lys Gly Asp Lys Ala Thr Tyr Glu Met
            290                 295                 300

Thr Val Lys Asn Glu Glu Lys His Ile Asp Ala Val Leu Thr Ala Glu
305                 310                 315                 320

Leu Thr Ala Lys Asp Asn Thr Val Ser Phe Glu Ile Thr Lys Val Glu
                325                 330                 335

Asn Lys Leu Thr Glu Gly Lys Pro Gly Thr Ala Leu Glu Ser Gly Lys
            340                 345                 350

Val Gly Asn Pro Ile Gln Thr Ile Glu Ile Pro Asn His Ser Leu Val
            355                 360                 365

Ser Val Asn Ser Thr Gln Lys Asn Ala Asn Leu Ile Gly Ala Ala Met
            370                 375                 380

Ser Thr Gln Thr Lys Val Ser Gly Asp Glu Tyr Val Glu Val Lys Ala
385                 390                 395                 400

Asn Thr Pro Ala Arg Glu Arg Asp Tyr Met Tyr Ala Phe Val Ser Asn
                405                 410                 415

Asn Glu Met Ser Ala Gly Leu Trp Ser Asn Ser Glu Tyr Glu Gly Arg
                420                 425                 430

Asn Ala Gly Ala Ser Ser Gly Gly Ser Asn Asn Thr Arg Val Met
            435                 440                 445

Ser Val Ser Glu Lys Lys Asp Gly Tyr Val Ser Met Gly Leu Gly Ser
450                 455                 460
```

-continued

```
Ser Ala Trp Tyr Trp His Arg Val Met Thr Asp Ser His Asn Arg Thr
465                 470                 475                 480

Trp Val Leu Glu Glu Thr Glu Asn Pro Lys Met Lys Val Val Ile Thr
                485                 490                 495

Gly Asn Cys Asn Gly Asp Lys Asn Val Asp Trp Gln Asp Gly Ala Val
            500                 505                 510

Ala Phe Arg Asp Ile Met Asn Asn Pro Phe Lys Ser Glu Glu Val Pro
        515                 520                 525

Glu Leu Val Ala Tyr Arg Ile Ala Met Asn Phe Gly Ser His Ala Gln
    530                 535                 540

Asn Pro Phe Leu Thr Thr Leu Asp Asn Val Lys Arg Val Ala Met His
545                 550                 555                 560

Thr Asp Gly Leu Gly Gln Ser Val Leu Leu Lys Gly Tyr Ala Asn Glu
                565                 570                 575

Gly His Asp Ser Ala His Pro Asp Tyr Ala Asp Ile Gly Lys Arg Ile
            580                 585                 590

Gly Gly Pro Glu Asp Met Lys Thr Leu Leu Glu Lys Gly Ala Asp Tyr
        595                 600                 605

Gly Ala Lys Phe Gly Ile His Val Asn Ala Gly Glu Met Tyr Pro Glu
    610                 615                 620

Ala Lys Ala Phe Lys Asp Asp Asn Val Arg Arg Asn Lys Asp Gly Ser
625                 630                 635                 640

Leu Arg Tyr Gly Trp Asn Trp Ile Asp Gln Gly Ile Gly Leu Asp Ser
                645                 650                 655

Ile Tyr Asp Leu Ala Thr Gly Glu Arg Glu Ala Arg Phe Asp Glu Leu
            660                 665                 670

His Glu Ile Leu Gly Gly Asp Gly Lys Asp Met Leu Asp Phe Ile Tyr
        675                 680                 685

Val Asp Ile Trp Gly Asn Asn Thr Gly Ser Asp Asn Asp Ser Gln
    690                 695                 700

Gln Thr Arg Lys Leu Ser Lys Glu Ile Asn Asp Asn Gly Trp Arg Met
705                 710                 715                 720

Ser Asn Glu Trp Gly Gly Ala Asn Glu Tyr Asp Ser Thr Phe Gln His
                725                 730                 735

Trp Ala Thr Asp Leu Thr Tyr Gly Gly Glu Gly Ala Lys Gly Glu Asn
            740                 745                 750

Ser Asp Val Met Arg Phe Leu Arg Asn His Gln Lys Asp Ser Trp Val
        755                 760                 765

Gly Asp Tyr Pro Thr Tyr Gly Gly Ala Ala Val Ala Pro Leu Leu Gly
    770                 775                 780

Gly Tyr Asn Met Lys Asp Phe Glu Gly Trp Gln Gly Arg Asn Asp Tyr
785                 790                 795                 800

Asp Ala Tyr Ile Thr Asn Leu Tyr Thr His Asp Leu Thr Thr Lys Phe
                805                 810                 815

Ile Gln His Tyr Gln Ile Val Asp Trp Glu Asp Gly Thr Pro Val Asn
            820                 825                 830

Val Gly Gly Ala Val Asn Trp Thr Pro Glu Met Lys Ile Thr Leu Lys
        835                 840                 845

Asp Glu Asp Gly Ser Thr Leu Val Leu Glu Arg Gly Ser Asn Asp Pro
    850                 855                 860

Ala Gln Ala Ala Tyr Arg Asp Arg Thr Met Thr Leu Asp Gly Lys Val
865                 870                 875                 880

Ile Ala Arg Gly Ala Val Ser Gln Gly Asp Arg Thr Asp Asp Ile
```

```
                885                 890                 895
Arg Asn Gly Asn Lys Lys Gly Thr Glu Ser Tyr Leu Leu Pro Trp Ile
                900                 905                 910

Trp Asp Ala Lys Thr Gly Glu Lys Val Lys Ser Glu Asp Glu Lys Leu
            915                 920                 925

Tyr His Trp Asn Thr Gln Gly Thr Thr Gln Trp Glu Leu Pro Asp
        930                 935                 940

Ser Trp Ala Asp Leu Lys Asp Val Lys Val Tyr Lys Leu Thr Asp Leu
945                 950                 955                 960

Gly Lys Thr Glu Glu Lys Thr Val Asn Val Val Asp Gly Lys Ile Thr
                965                 970                 975

Leu Glu Ala Glu Ser Glu Val Pro Tyr Val Val Cys Lys Gly Glu Lys
            980                 985                 990

Glu Asn Ile Lys Val Thr Trp Ser Glu Gly Met His Ile Val Asp Ala
            995                 1000                1005

Gly Phe Asn Ser Gly Ser Leu Asp Met Trp Thr Lys Ala Gly Glu
    1010                1015                1020

Gly Thr Ala Gln Ile Ala Lys Ser Gln His Ser Asn Pro Met Met
    1025                1030                1035

Lys Leu Asp Gly Lys Val Ser Met Thr Gln Lys Leu Thr Asp Leu
    1040                1045                1050

Glu Ala Gly Lys Gln Tyr Ala Val Leu Val Gly Val Asp Asn Arg
    1055                1060                1065

Ser Asp Ala Lys Ala Ser Val Glu Ile Lys Ser Gly Asp Lys Val
    1070                1075                1080

Leu Gly Ser Asn Tyr Thr Thr Arg Ser Ile Ala Lys Asn Tyr Val
    1085                1090                1095

Lys Ala Tyr Thr His Asn Thr Asn Ser Ser Thr Val Asp Gly Ser
    1100                1105                1110

Ser Tyr Phe Gln Asn Met Tyr Ile Phe Phe Thr Ala Pro Lys Ser
    1115                1120                1125

Gly Asp Val Thr Leu Thr Ile Ala Arg Glu Ala Gly Glu Gly Ser
    1130                1135                1140

Ser Tyr Phe Asp Asp Ile Arg Ile Val Gln Asn Asp Ser Lys Asn
    1145                1150                1155

Ile Thr Thr Asn Glu Lys Gly Glu Val Val Lys Phe Glu Gln Asn
    1160                1165                1170

Phe Glu Lys Ser Val Gln Gly Leu Tyr Pro Phe Val Val Gly Gly
    1175                1180                1185

Ile Glu Gly Val Glu Asp Asn Arg Ile His Leu Ser Glu Arg His
    1190                1195                1200

Asp Lys Tyr Thr Gln Ala Gly Trp Asp Val Lys Lys Met Asp Asp
    1205                1210                1215

Val Leu Asp Gly Asp Trp Ser Val Lys Ile Asn Gly Leu Thr Gln
    1220                1225                1230

Arg Ser Thr Leu Ala Tyr Gln Thr Ile Pro Gln Asn Phe Arg Phe
    1235                1240                1245

Glu Pro Gly Val Thr Tyr Asn Val Ser Phe Asp Tyr Gln Ala Gly
    1250                1255                1260

Ser Asp Gly Ile Tyr Ala Ala Val Gly Val Gly Glu Tyr Asn
    1265                1270                1275

Gly Asn Val Gln Leu Lys Glu Leu Pro Met Ser Met Gly Lys Glu
    1280                1285                1290
```

```
Lys Asp Gly His Phe Thr Met Gln Val Thr Gly Asp Ser Thr Gly
    1295                1300                1305

Gln Thr Trp Phe Gly Ile Tyr Ser Thr Glu Lys Ala Pro Asp Leu
    1310                1315                1320

Gln Gly Val Ser Pro Asp Ala Ala Glu Ala Asn Phe Gly Gly Tyr
    1325                1330                1335

Lys Glu Leu Val Leu Asp Asn Leu Val Ile Glu Lys Val Thr Glu
    1340                1345                1350

Glu Val Thr Lys Glu Lys Leu Ala Ala Leu Val Ala Glu Ala Glu
    1355                1360                1365

Glu Lys Tyr Lys Glu Ile Asp Tyr Arg Pro Glu Ile Trp Ser Ser
    1370                1375                1380

Phe Gln Asp Val Leu Lys Glu Ala Lys Ala Val Leu Asp Lys Glu
    1385                1390                1395

Gly Ala Ser Gln Asp Glu Ile Glu Lys Ala Tyr Tyr Glu Leu Lys
    1400                1405                1410

Ala Ala Met Val Thr Met Asp Asn Ser Ala Gly Ile Asp Ala Thr
    1415                1420                1425

Asp Asp Ser Lys Asp Leu Pro Lys Glu Gln Met Thr Ala Thr Ala
    1430                1435                1440

Gly Ser Glu Gln Ala Gln Glu Gly Gly Glu Gly Pro Ala Ser Asn
    1445                1450                1455

Val Leu Asp Gly Asn Ala Asp Thr Ile Trp His Thr Val Trp Ala
    1460                1465                1470

Gly Thr Pro Ile Glu Asn His Trp Leu Asn Leu Gln Leu Asp Lys
    1475                1480                1485

Pro Ala Thr Val Ser Gly Leu Arg Leu Gln Gln Arg Ser Gly Arg
    1490                1495                1500

Asn Gly Ile Ile Arg Glu Ala Glu Ile Trp Val Lys Lys Ala Gly
    1505                1510                1515

Ala Ala Asp Tyr Glu Lys Val Ala Asp Ala Ser Phe Gly Gly Thr
    1520                1525                1530

Gly Trp Gln Ala Val Ala Phe Glu Glu Val Lys Asp Val Thr Asp
    1535                1540                1545

Val Lys Leu Val Pro Thr Ala Thr Thr Gly Asp Glu Ala Asn Lys
    1550                1555                1560

Phe Ser Ala Ala Ala Glu Ile Arg Val Met Gly Arg Phe Gln Asp
    1565                1570                1575

Glu Glu Val Glu Val Asn Lys Ala Asp Leu Thr Ala Leu Val Glu
    1580                1585                1590

Lys Ala Glu Val Leu Lys Glu Lys Asp Tyr Thr Ser Glu Thr Trp
    1595                1600                1605

Lys Pro Phe Ala Glu Ala Leu Lys Glu Ala Gln Ala Val Leu Ala
    1610                1615                1620

Lys Glu Asp Ala Ser Gln Ala Glu Val Asp Ala Ala Gln Thr Ser
    1625                1630                1635

Leu Gln Thr Ala Met Asp Gly Leu Lys Lys Pro Gly Thr Thr Asp
    1640                1645                1650

Asn Lys Asn Pro Gly Thr Thr Asp Asn Lys Asn Pro Gly Ala Pro
    1655                1660                1665

Asn Lys Gly Gln Ala Val Gln Thr Gly Asp Ala Thr Ser Phe Phe
    1670                1675                1680
```

-continued

```
Gly Trp Gly Ala Ala Gly Ile Phe Gly Leu Phe Ala Ala Ala Ala
    1685                1690                1695

Ala Phe Phe Glu Arg Lys Arg Arg Arg Gln
    1700                1705

<210> SEQ ID NO 9
<211> LENGTH: 1361
<212> TYPE: PRT
<213> ORGANISM: Streptomyces coelicolor

<400> SEQUENCE: 9

Met Ala Ala Ile Thr Pro Lys Arg Ser Val Arg Val Asp Thr Ser Thr
1               5                   10                  15

Gly Ser Ser Ser Pro Pro Thr Gly Arg Ala Arg Val Arg Arg His Gly
            20                  25                  30

Ala Val Val Ala Ala Leu Gly Leu Thr Ala Gly Leu Leu Ser Ala Ala
        35                  40                  45

Ala Leu Pro Ala Gly Ala Ala Pro Pro Arg Pro Ala Ala Ala Ala
    50                  55                  60

Pro Ala Gly Ala Pro Thr Pro Val Glu Leu Ser Arg Gly Gly Leu Thr
65                  70                  75                  80

Val Thr Val Ala Lys Glu Phe Pro Gln Val Ile Ser Tyr Arg Leu Gly
                85                  90                  95

Arg Arg Gly Leu Asp Gly Arg Ala Thr Ala Leu Asp Gly Phe Thr Val
            100                 105                 110

Asn Gly Glu Ser His Arg Ala Thr Thr Thr Val Lys Ala Lys Gly Ser
        115                 120                 125

Arg Ala Val Tyr Thr Ser Thr Phe Glu Asp Leu Pro Gly Leu Thr Ile
    130                 135                 140

Thr Ser Ser Ile Thr Val Thr Lys Glu Thr Thr Val Val Phe Ala Val
145                 150                 155                 160

Glu Lys Ile Ser Gly Glu Ala Ala Pro Gly Val Arg Thr Leu Ala Ile
                165                 170                 175

Pro Gly Gln Ser Leu Val Ser Val Asp Ser Ala Glu Pro Gly Ala Asn
            180                 185                 190

Leu Ala Arg Thr Lys Ile Ser Thr Asp Ser Thr Thr Ala Asp Arg
        195                 200                 205

Phe Val Pro Val Thr Gly Asp Thr Ala Pro Asp Lys Gly Pro Val Gly
    210                 215                 220

Thr Pro Tyr Ala Phe Val Gly Asn Ala Gln Leu Ser Ala Gly Ile Ile
225                 230                 235                 240

Thr Asn Ala Thr Glu Asp Ser Pro Gln Asp Asp Asn Thr Asp Trp Asn
                245                 250                 255

Thr Arg Leu Gln Ser Arg Ile Val Asp Glu Gly Glu Gly Arg Arg Arg
            260                 265                 270

Ala Glu Leu Ser Ala Gly Thr Tyr Thr Tyr His Pro Glu Gly Ala Thr
        275                 280                 285

Asp Pro Arg Val Asp Thr Tyr Glu Leu Pro Arg Ala Thr Val Val Leu
    290                 295                 300

Ala Ala Asp Ala Asn Arg Asp Gly Thr Val Asp Trp Gln Asp Gly Ala
305                 310                 315                 320

Ile Ala His Arg Glu His Met Arg Arg Pro Leu Gly Ala Asp Arg Val
                325                 330                 335

Pro Glu Arg Val Val Gln Arg Ile Pro Phe Asn Phe Ala Ser Gln Ala
            340                 345                 350
```

```
Thr Asn Pro Phe Leu Lys Thr Leu Asp Asn Thr Lys Arg Ile Ser Met
        355                 360                 365

Ala Thr Asp Asp Leu Gly Gln Trp Val Leu Glu Lys Gly Tyr Ala Ser
370                 375                 380

Glu Gly His Asp Ser Ala His Pro Asp Tyr Gly Gly Asn Glu Asn Val
385                 390                 395                 400

Arg Ala Gly Gly Trp Lys Asp Leu Asn Arg Leu Thr Arg Thr Gly Ala
                405                 410                 415

Gly Tyr Asn Ala Asp Phe Ala Val His Val Asn Ala Thr Glu Ala Tyr
                420                 425                 430

Ala Gln Ala Arg Thr Phe Thr Glu Asp Met Val Ala Gly Gln Ala Asp
        435                 440                 445

Gly Trp Asp Trp Leu Asn Gln Ala Tyr His Ile Asp Gln Arg Lys Asp
    450                 455                 460

Leu Gly Thr Gly Ala Val Leu Asp Arg Phe Lys Gln Leu Arg Lys Glu
465                 470                 475                 480

Ala Pro Gly Ile Arg Thr Val Tyr Ile Asp Ala Tyr Tyr Ser Ser Gly
                485                 490                 495

Trp Leu Ala Asp Gly Leu Ala Ala Gly Leu Arg Glu Met Gly Phe Glu
            500                 505                 510

Val Ala Thr Glu Trp Ala Tyr Lys Phe Glu Gly Thr Ser Val Trp Ser
        515                 520                 525

His Trp Ala Ala Asp Lys Asn Tyr Gly Gly Ala Thr Asn Lys Gly Ile
    530                 535                 540

Asn Ser Asp Ile Val Arg Phe Ile Ala Asn Ala Asp Arg Asp Val Trp
545                 550                 555                 560

Asn Val Asp Pro Leu Leu Gly Gly Ala Ser Val Val Glu Phe Glu Gly
                565                 570                 575

Trp Thr Gly Gln Asp Asp Trp Asn Ala Phe Tyr Arg Asn Ile Trp Thr
            580                 585                 590

Asp Asn Leu Pro Thr Lys Phe Leu Gln His Phe Gln Val Leu Asp Trp
        595                 600                 605

Asp Arg Gly Arg Ser Ala Arg Leu Thr Gly Gly Val Asp Val Lys Ser
    610                 615                 620

Val Asp Gly Glu Arg Arg Ile Ser Met Asp Gly Thr Glu Val Leu Lys
625                 630                 635                 640

Gly Asp Thr Tyr Leu Leu Pro Trp Gln Asn Ala Gly Lys Asp Asp Gly
                645                 650                 655

Thr Ser Ser Pro Arg Asp Ala Asp Lys Met Tyr Phe Tyr Ser Ala Ser
            660                 665                 670

Gly Gly Glu His Thr Phe Glu Leu Thr Gly Gln Phe Ala Gly Thr Glu
        675                 680                 685

Asp Phe Thr Leu Tyr Glu Leu Thr Asp Gln Gly Arg Ala Glu Lys Ala
690                 695                 700

Arg Val Thr Ala His Glu Gly Arg Val Thr Leu Thr Ala Glu Lys Gly
705                 710                 715                 720

Gln Pro Tyr Val Leu Val Pro Asn Gly Gly Arg Ala Pro His Arg Asp
                725                 730                 735

Ala His Tyr Gly Glu Phe Thr Gly Leu Ser Asp Pro Gly Phe Asn Gly
            740                 745                 750

Gly Asp Leu Asp Ala Trp Asn Ala Ser Gly Gly Ala Glu Ile Val Arg
        755                 760                 765
```

Ala Gly Asn Gly Asp Asn Val Val Arg Leu Gly Glu Asp Ala Ser Gly
770             775                 780

Ile Ala Gln Arg Val Arg Gly Leu Thr Pro Gly Glu Arg Tyr Thr Leu
785             790                 795                 800

Gly Ala Asp Val Gly Ile Gly Pro Gly Glu Arg Glu Thr Thr Leu
            805                 810                 815

Arg Val Arg Gly Gly Lys Asp Ser Glu Ala Arg Thr Phe Asp Ile Thr
            820                 825                 830

Pro Ala Arg Asn Arg Met Ala Ser Asp Glu Lys Arg Asp Thr Tyr Ser
            835                 840                 845

Gln Arg Ala Ser Val Ser Phe Thr Ala Pro Arg Asp Gly Ser Val Thr
850                 855                 860

Val Glu Leu Gly Ala Val Ala Gly Gly Ala Pro Val Val Leu Asp Asp
865                 870                 875                 880

Val Arg Val Met Val Asp Thr Thr Ala Pro Leu Pro Arg Ser Gln Asp
                885                 890                 895

Gly Thr Val Val Ala His Asp Asp Phe Glu Gly Asn Arg Pro Gly Trp
                900                 905                 910

Gly Pro Phe Val Lys Gly Asp Ala Gly Gly Val Thr Asp Pro Arg Thr
                915                 920                 925

Ser Ile Ser Asp Leu His Ala Pro Tyr Ser Gln Lys Glu Trp Lys Asn
930                 935                 940

Thr Tyr Ser Pro Tyr Asp Thr Gly Ala Leu Lys Gly Arg Ala Val Asp
945                 950                 955                 960

Asp Val Leu Ala Gly Arg His Ser Leu Lys Ser His Ala Glu Asn Thr
                965                 970                 975

Gly Leu Val His Arg Thr Thr Pro Ala Thr Val Pro Phe Glu Glu Gly
                980                 985                 990

His Arg Tyr Arg Val Ser Phe Ser Tyr Gln Thr Asn Val Glu Gly Gln
                995                 1000                1005

Trp Ala Trp Val Thr Gly Ala Asp Arg Val Ala Asp Gly Thr Thr
    1010                1015                1020

Thr Ser Arg Asp Ile Thr Arg Asp Val Leu Ala Pro Ala Leu Asp
    1025                1030                1035

Thr Ala Ala Tyr Ser Arg Glu Phe Val Ala Gly Cys Gly Asp Thr
    1040                1045                1050

Trp Val Gly Leu Arg Arg Leu Gly Ser Ala Arg Gly Thr Asp Leu
    1055                1060                1065

Val Leu Asp Asp Phe Thr Val Thr Asp Leu Gly Glu Ala Asp Thr
    1070                1075                1080

Gly Ala Ala Cys Ala Ala Val Thr Ala Pro Ser Gly Ala Glu Leu
    1085                1090                1095

Ser Pro Gly Val Pro Gly Glu Tyr Val Thr Ala Phe Thr Asn His
    1100                1105                1110

Glu Ser Ala Gly Ala Glu Asn Val Gly Ile Ala Leu Gln Gly Leu
    1115                1120                1125

Pro Glu Gly Trp Lys Ala Glu Val Lys Glu Lys Asp Gly Asn Leu
    1130                1135                1140

Phe Glu Arg Val Gln Pro Gly Ala Thr Val Arg Thr Thr Trp Leu
    1145                1150                1155

Leu Thr Pro Pro Ala Gly Thr Ala Gly Thr Ser Ala Thr Trp Gln
    1160                1165                1170

Val Thr Ala Ala Tyr Ala His Glu Gly Ala Thr Arg Thr Val Ser

```
                1175                1180                1185
Thr Gly Ala Arg Ala Ala Val Thr Asp Glu Pro Val Leu Ala Pro
            1190                1195                1200

Ala Ser Thr Thr Ala Thr Ala Asp Ser Glu Asn Thr Ser Ser Gly
            1205                1210                1215

Ala Ser Glu Gly Pro Val Ser Asn Val Leu Asp Gly Asp Ala Gly
            1220                1225                1230

Thr Ile Trp His Thr Asp Tyr Thr Thr Ser Gln Ala Pro Tyr Pro
            1235                1240                1245

His Trp Val Thr Leu Lys Leu Gly Gly Ala Ala Asp Val Asp Gly
            1250                1255                1260

Phe Gly Tyr Leu Gly Arg Gln Ser Gly Gly Pro Asn Gly Arg Val
            1265                1270                1275

Ala Asp Tyr Glu Val Ala Val Ser Asp Asp Gly Glu Ala Trp Thr
            1280                1285                1290

Thr Val Ala Thr Gly Thr Leu Lys Asp Val Pro Arg Thr Gln Arg
            1295                1300                1305

Val Ser Phe Asp Arg Val Arg Ala Ser Tyr Val Arg Phe Thr Ala
            1310                1315                1320

Leu Asp Ala Leu Asn Gly Gln Pro Tyr Ala Ala Ala Ala Glu Met
            1325                1330                1335

Arg Val Tyr Gly Val Pro Val Asp Leu Pro Thr Gly Tyr Pro Pro
            1340                1345                1350

Gly Glu Arg Pro Ala Asp Ala Arg
            1355                1360

<210> SEQ ID NO 10
<211> LENGTH: 1767
<212> TYPE: PRT
<213> ORGANISM: Streptococcus pneumoniae

<400> SEQUENCE: 10

Met Asn Lys Gly Leu Phe Glu Lys Arg Cys Lys Tyr Ser Ile Arg Lys
1               5                   10                  15

Phe Ser Leu Gly Val Ala Ser Val Met Ile Gly Ala Ala Phe Phe Gly
                20                  25                  30

Thr Ser Pro Val Leu Ala Asp Ser Val Gln Ser Gly Ser Thr Ala Asn
        35                  40                  45

Leu Pro Ala Asp Leu Ala Thr Ala Leu Ala Thr Ala Lys Glu Asn Asp
    50                  55                  60

Gly Arg Asp Phe Glu Ala Pro Lys Val Gly Glu Asp Gln Gly Ser Pro
65                  70                  75                  80

Glu Val Thr Asp Gly Pro Lys Thr Glu Glu Glu Leu Leu Ala Leu Glu
                85                  90                  95

Lys Glu Lys Pro Ala Glu Glu Lys Pro Lys Glu Asp Lys Pro Ala Ala
            100                 105                 110

Ala Lys Pro Glu Thr Pro Lys Thr Val Thr Pro Glu Trp Gln Thr Val
        115                 120                 125

Ala Asn Lys Glu Gln Gln Gly Thr Val Thr Ile Arg Glu Glu Lys Gly
    130                 135                 140

Val Arg Tyr Asn Gln Leu Ser Ser Thr Ala Gln Asn Asp Asn Ala Gly
145                 150                 155                 160

Lys Pro Ala Leu Phe Glu Lys Lys Gly Leu Thr Val Asp Ala Asn Gly
                165                 170                 175
```

```
Asn Ala Thr Val Asp Leu Thr Phe Lys Asp Ser Glu Lys Gly Lys
                180                 185                 190

Ser Arg Phe Gly Val Phe Leu Lys Phe Lys Asp Thr Lys Asn Asn Val
    195                 200                 205

Phe Val Gly Tyr Asp Lys Asp Gly Trp Phe Trp Glu Tyr Lys Ser Pro
    210                 215                 220

Thr Thr Ser Thr Trp Tyr Arg Gly Ser Arg Val Ala Ala Pro Glu Thr
225                 230                 235                 240

Gly Ser Thr Asn Arg Leu Ser Ile Thr Leu Lys Ser Asp Gly Gln Leu
                245                 250                 255

Asn Ala Ser Asn Asn Asp Val Asn Leu Phe Asp Thr Val Thr Leu Pro
                260                 265                 270

Ala Ala Val Asn Asp His Leu Lys Asn Glu Lys Lys Ile Leu Leu Lys
                275                 280                 285

Ala Gly Ser Tyr Asp Asp Glu Arg Thr Val Val Ser Val Lys Thr Asp
                290                 295                 300

Asn Gln Glu Gly Val Lys Thr Glu Asp Thr Pro Ala Glu Lys Glu Thr
305                 310                 315                 320

Gly Pro Glu Val Asp Asp Ser Lys Val Thr Tyr Asp Thr Ile Gln Ser
                325                 330                 335

Lys Val Leu Lys Ala Val Ile Asp Gln Ala Phe Pro Arg Val Lys Glu
                340                 345                 350

Tyr Ser Leu Asn Gly His Thr Leu Pro Gly Gln Val Gln Gln Phe Asn
                355                 360                 365

Gln Val Phe Ile Asn Asn His Arg Ile Thr Pro Glu Val Thr Tyr Lys
                370                 375                 380

Lys Ile Asn Glu Thr Thr Ala Glu Tyr Leu Met Lys Leu Arg Asp Asp
385                 390                 395                 400

Ala His Leu Ile Asn Ala Glu Met Thr Val Arg Leu Gln Val Val Asp
                405                 410                 415

Asn Gln Leu His Phe Asp Val Thr Lys Ile Val Asn His Asn Gln Val
                420                 425                 430

Thr Pro Gly Gln Lys Ile Asp Asp Glu Ser Lys Leu Leu Ser Ser Ile
                435                 440                 445

Ser Phe Leu Gly Asn Ala Leu Val Ser Val Ser Ser Asn Gln Thr Gly
                450                 455                 460

Ala Lys Phe Asp Gly Ala Thr Met Ser Asn Asn Thr His Val Ser Gly
465                 470                 475                 480

Asp Asp His Ile Asp Val Thr Asn Pro Met Lys Asp Leu Ala Lys Gly
                485                 490                 495

Tyr Met Tyr Gly Phe Val Ser Thr Asp Lys Leu Ala Ala Gly Val Trp
                500                 505                 510

Ser Asn Ser Gln Asn Ser Tyr Gly Gly Ser Asn Asp Trp Thr Arg
    515                 520                 525

Leu Thr Ala Tyr Lys Glu Thr Val Gly Asn Ala Asn Tyr Val Gly Ile
                530                 535                 540

His Ser Ser Glu Trp Gln Trp Glu Lys Ala Tyr Lys Gly Ile Val Phe
545                 550                 555                 560

Pro Glu Tyr Thr Lys Glu Leu Pro Ser Ala Lys Val Val Ile Thr Glu
                565                 570                 575

Asp Ala Asn Ala Asp Lys Asn Val Asp Trp Gln Asp Gly Ala Ile Ala
                580                 585                 590

Tyr Arg Ser Ile Met Asn Asn Pro Gln Gly Trp Glu Lys Val Lys Asp
```

```
                    595                 600                 605
Ile Thr Ala Tyr Arg Ile Ala Met Asn Phe Gly Ser Gln Ala Gln Asn
610                 615                 620

Pro Phe Leu Met Thr Leu Asp Gly Ile Lys Lys Ile Asn Leu His Thr
625                 630                 635                 640

Asp Gly Leu Gly Gln Gly Val Leu Leu Lys Gly Tyr Gly Ser Glu Gly
                    645                 650                 655

His Asp Ser Gly His Leu Asn Tyr Ala Asp Ile Gly Lys Arg Ile Gly
                660                 665                 670

Gly Val Glu Asp Phe Lys Thr Leu Ile Glu Lys Ala Lys Lys Tyr Gly
                675                 680                 685

Ala His Leu Gly Ile His Val Asn Ala Ser Glu Thr Tyr Pro Glu Ser
690                 695                 700

Lys Tyr Phe Asn Glu Lys Ile Leu Arg Lys Asn Pro Asp Gly Ser Tyr
705                 710                 715                 720

Ser Tyr Gly Trp Asn Trp Leu Asp Gln Gly Ile Asn Ile Asp Ala Ala
                725                 730                 735

Tyr Asp Leu Ala His Gly Arg Leu Ala Arg Trp Glu Asp Leu Lys Lys
                740                 745                 750

Lys Leu Gly Asp Gly Leu Asp Phe Ile Tyr Val Asp Val Trp Gly Asn
                755                 760                 765

Gly Gln Ser Gly Asp Asn Gly Ala Trp Ala Thr His Val Leu Ala Lys
770                 775                 780

Glu Ile Asn Lys Gln Gly Trp Arg Phe Ala Ile Glu Trp Gly His Gly
785                 790                 795                 800

Gly Glu Tyr Asp Ser Thr Phe His His Trp Ala Ala Asp Leu Thr Tyr
                805                 810                 815

Gly Gly Tyr Thr Asn Lys Gly Ile Asn Ser Ala Ile Thr Arg Phe Ile
                820                 825                 830

Arg Asn His Gln Lys Asp Ala Trp Val Gly Asp Tyr Arg Ser Tyr Gly
                835                 840                 845

Gly Ala Ala Asn Tyr Pro Leu Leu Gly Gly Tyr Ser Met Lys Asp Phe
850                 855                 860

Glu Gly Trp Gln Gly Arg Ser Asp Tyr Asn Gly Tyr Val Thr Asn Leu
865                 870                 875                 880

Phe Ala His Asp Val Met Thr Lys Tyr Phe Gln His Phe Thr Val Ser
                885                 890                 895

Lys Trp Glu Asn Gly Thr Pro Val Thr Met Thr Asp Asn Gly Ser Thr
                900                 905                 910

Tyr Lys Trp Thr Pro Glu Met Arg Val Glu Leu Val Asp Ala Asp Asn
                915                 920                 925

Asn Lys Val Val Thr Arg Lys Ser Asn Asp Val Asn Ser Pro Gln
930                 935                 940

Tyr Arg Glu Arg Thr Val Thr Leu Asn Gly Arg Val Ile Gln Asp Gly
945                 950                 955                 960

Ser Ala Tyr Leu Thr Pro Trp Asn Trp Asp Ala Asn Gly Lys Lys Leu
                965                 970                 975

Ser Thr Asp Lys Glu Lys Met Tyr Phe Asn Thr Gln Ala Gly Ala
                980                 985                 990

Thr Thr Trp Thr Leu Pro Ser Asp Trp Ala Lys Ser Lys Val Tyr Leu
                995                 1000                1005

Tyr Lys Leu Thr Asp Gln Gly Lys Thr Glu Glu Gln Glu Leu Thr
                1010                1015                1020
```

```
Val Lys Asp Gly Lys Ile Thr Leu Asp Leu Leu Ala Asn Gln Pro
    1025            1030                1035

Tyr Val Leu Tyr Arg Ser Lys Gln Thr Asn Pro Glu Met Ser Trp
    1040            1045                1050

Ser Glu Gly Met His Ile Tyr Asp Gln Gly Phe Asn Ser Gly Thr
    1055            1060                1065

Leu Lys His Trp Thr Ile Ser Gly Asp Ala Ser Lys Ala Glu Ile
    1070            1075                1080

Val Lys Ser Gln Gly Ala Asn Asp Met Leu Arg Ile Gln Gly Asn
    1085            1090                1095

Lys Glu Lys Val Ser Leu Thr Gln Lys Leu Thr Gly Leu Lys Pro
    1100            1105                1110

Asn Thr Lys Tyr Ala Val Tyr Val Gly Val Asp Asn Arg Ser Asn
    1115            1120                1125

Ala Lys Ala Ser Ile Thr Val Asn Thr Gly Glu Lys Glu Val Thr
    1130            1135                1140

Thr Tyr Thr Asn Lys Ser Leu Ala Leu Asn Tyr Val Lys Ala Tyr
    1145            1150                1155

Ala His Asn Thr Arg Arg Asp Asn Ala Thr Val Asp Asp Thr Ser
    1160            1165                1170

Tyr Phe Gln Asn Met Tyr Ala Phe Phe Thr Thr Gly Ala Asp Val
    1175            1180                1185

Ser Asn Val Thr Leu Thr Leu Ser Arg Glu Ala Gly Asp Gln Ala
    1190            1195                1200

Thr Tyr Phe Asp Glu Ile Arg Thr Phe Glu Asn Asn Ser Ser Met
    1205            1210                1215

Tyr Gly Asp Lys His Asp Thr Gly Lys Gly Thr Phe Lys Gln Asp
    1220            1225                1230

Phe Glu Asn Val Ala Gln Gly Ile Phe Pro Phe Val Gly Gly
    1235            1240                1245

Val Glu Gly Val Glu Asp Asn Arg Thr His Leu Ser Glu Lys His
    1250            1255                1260

Asn Pro Tyr Thr Gln Arg Gly Trp Asn Gly Lys Lys Val Asp Asp
    1265            1270                1275

Val Ile Glu Gly Asn Trp Ser Leu Lys Thr Asn Gly Leu Val Ser
    1280            1285                1290

Arg Arg Asn Leu Val Tyr Gln Thr Ile Pro Gln Asn Phe Arg Phe
    1295            1300                1305

Glu Ala Gly Lys Thr Tyr Arg Val Thr Phe Glu Tyr Glu Ala Gly
    1310            1315                1320

Ser Asp Asn Thr Tyr Ala Phe Val Val Gly Lys Gly Glu Phe Gln
    1325            1330                1335

Ser Gly Arg Arg Gly Thr Gln Ala Ser Asn Leu Glu Met His Glu
    1340            1345                1350

Leu Pro Asn Thr Trp Thr Asp Ser Lys Lys Ala Lys Lys Ala Thr
    1355            1360                1365

Phe Leu Val Thr Gly Ala Glu Thr Gly Asp Thr Trp Val Gly Ile
    1370            1375                1380

Tyr Ser Thr Gly Asn Ala Ser Asn Thr Arg Gly Asp Ser Gly Gly
    1385            1390                1395

Asn Ala Asn Phe Arg Gly Tyr Asn Asp Phe Met Met Asp Asn Leu
    1400            1405                1410
```

Gln Ile Glu Glu Ile Thr Leu Thr Gly Lys Met Leu Thr Glu Asn
1415                1420                1425

Ala Leu Lys Asn Tyr Leu Pro Thr Val Ala Met Thr Asn Tyr Thr
1430                1435                1440

Lys Glu Ser Met Asp Ala Leu Lys Glu Ala Val Phe Asn Leu Ser
1445                1450                1455

Gln Ala Asp Asp Ile Ser Val Glu Glu Ala Arg Ala Glu Ile
1460                1465                1470

Ala Lys Ile Glu Ala Leu Lys Asn Ala Leu Val Gln Lys Lys Thr
1475                1480                1485

Ala Leu Val Ala Asp Asp Phe Ala Ser Leu Thr Ala Pro Ala Gln
1490                1495                1500

Ala Gln Glu Gly Leu Ala Asn Ala Phe Asp Gly Asn Val Ser Ser
1505                1510                1515

Leu Trp His Thr Ser Trp Asn Gly Gly Asp Val Gly Lys Pro Ala
1520                1525                1530

Thr Met Val Leu Lys Glu Pro Thr Glu Ile Thr Gly Leu Arg Tyr
1535                1540                1545

Val Pro Arg Gly Ser Gly Ser Asn Gly Asn Leu Arg Asp Val Lys
1550                1555                1560

Leu Val Val Thr Asp Glu Ser Gly Lys Glu His Thr Phe Thr Ala
1565                1570                1575

Thr Asp Trp Pro Asn Asn Asn Lys Pro Lys Asp Ile Asp Phe Gly
1580                1585                1590

Lys Thr Ile Lys Ala Lys Lys Ile Val Leu Thr Gly Thr Lys Thr
1595                1600                1605

Tyr Gly Asp Gly Gly Asp Lys Tyr Gln Ser Ala Ala Glu Leu Ile
1610                1615                1620

Phe Thr Arg Pro Gln Val Ala Glu Thr Pro Leu Asp Leu Ser Gly
1625                1630                1635

Tyr Glu Ala Ala Leu Val Lys Ala Gln Lys Leu Thr Asp Lys Asp
1640                1645                1650

Asn Gln Glu Glu Val Ala Ser Val Gln Ala Ser Met Lys Tyr Ala
1655                1660                1665

Thr Asp Asn His Leu Leu Thr Glu Arg Met Val Glu Tyr Phe Ala
1670                1675                1680

Asp Tyr Leu Asn Gln Leu Lys Asp Ser Ala Thr Lys Pro Asp Ala
1685                1690                1695

Pro Thr Val Glu Lys Pro Glu Phe Lys Leu Arg Ser Leu Ala Ser
1700                1705                1710

Glu Gln Gly Lys Thr Pro Asp Tyr Lys Gln Glu Ile Ala Arg Pro
1715                1720                1725

Glu Thr Pro Glu Gln Ile Leu Pro Ala Thr Gly Glu Ser Gln Ser
1730                1735                1740

Asp Thr Ala Leu Ile Leu Ala Ser Val Ser Leu Ala Leu Ser Ala
1745                1750                1755

Leu Phe Val Val Lys Thr Lys Lys Asp
1760                1765

<210> SEQ ID NO 11
<211> LENGTH: 37
<212> TYPE: DNA
<213> ORGANISM: artificial
<220> FEATURE:
<223> OTHER INFORMATION: primer

<400> SEQUENCE: 11
cccatatgaa acatggaaaa ataaaacgat ttagtac                    37

<210> SEQ ID NO 12
<211> LENGTH: 36
<212> TYPE: DNA
<213> ORGANISM: artificial
<220> FEATURE:
<223> OTHER INFORMATION: primer

<400> SEQUENCE: 12
ccctcgagtt tttttgattc cactgtgacc gtaaag                     36

<210> SEQ ID NO 13
<211> LENGTH: 36
<212> TYPE: DNA
<213> ORGANISM: artificial
<220> FEATURE:
<223> OTHER INFORMATION: primer

<400> SEQUENCE: 13
cccatatggg tagaaaatgc atgaataaga agattg                     36

<210> SEQ ID NO 14
<211> LENGTH: 40
<212> TYPE: DNA
<213> ORGANISM: artificial
<220> FEATURE:
<223> OTHER INFORMATION: primer

<400> SEQUENCE: 14
ccctcgagtc tagcagttct aacagttatt gattccttag                 40

<210> SEQ ID NO 15
<211> LENGTH: 25
<212> TYPE: DNA
<213> ORGANISM: artificial
<220> FEATURE:
<223> OTHER INFORMATION: primer

<400> SEQUENCE: 15
ggagacaucc atatgagtcg caccc                                 25

<210> SEQ ID NO 16
<211> LENGTH: 29
<212> TYPE: DNA
<213> ORGANISM: artificial
<220> FEATURE:
<223> OTHER INFORMATION: primer

<400> SEQUENCE: 16
gggaaagutt aacgaccttg acgtgaaac                             29

We claim:

1. A preparation in a reaction vessel, comprising a recombinant polypeptide and glycerol, the recombinant polypeptide comprising amino acids 1-1155 of SEQ ID NO: 4, wherein the recombinant polypeptide consists of less than 1400 amino acids, and lacks a carbohydrate-binding domain at the C-terminal end.

2. A synthetic vector comprising a nucleic acid that encodes a polypeptide according to claim 1.

3. A method, comprising:
a) combining in a reaction vessel a eukaryotic glycoprotein or glycopeptide with a purified prokaryotic glycosidase having an amino acid sequence comprising:
  i) an amino acid sequence at least 35.2% identical to SEQ ID NO: 2;
  ii) SEQ ID NO: 1; and
  iii) an FDY amino acid sequence in a central conserved domain wherein the number of amino acids between the FDY and a C-terminal end of the polypeptide is no more than 200 amino acids,
  wherein the glycosidase polypeptide consists of less than 1400 amino acids and lacks a carbohydrate-binding domain at the C-terminal end;
b) cleaving a Core 3 (GlcNAcβ1,3GalNAc) O-linked glycan in the glycoprotein or glycopeptide; and
c) separating the glycan products cleaved from the glycoprotein or glycopeptide.

4. The method according to claim 3, further comprising treating the glycoprotein or glycopeptide with a neuraminidase.

5. The method according to claim 4, further comprising sequentially or simultaneously treating the glycoprotein or glycopeptide with the neuraminidase and the glycosidase.

6. The method according to claim 3, wherein the glycosidase is active at 25° C.

7. The method according to claim 3, wherein the glycosidase is capable of cleaving 100% of the Core 3 O-linked glycans as determined by thin layer chromatography (TLC).

8. The method according to claim 3, further comprising cleaving the Core 3 O-linked glycans at pH 2.0 to 9.0.

9. The preparation according to claim 1 further comprising neuraminidase.

* * * * *